United States Patent
Ralph et al.

(10) Patent No.: US 11,807,876 B2
(45) Date of Patent: Nov. 7, 2023

(54) P-COUMAROYL-COA:MONOLIGNOL TRANSFERASES

(71) Applicant: WISCONSIN ALUMNI RESEARCH FOUNDATION, Madison, WI (US)

(72) Inventors: John Ralph, Madison, WI (US); Steven D. Karlen, Madison, WI (US); Rebecca Anne Smith, Madison, WI (US); Brian Fox, Madison, WI (US); Emily Beebe, Stoughton, WI (US); Craig Bingman, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 90 days.

(21) Appl. No.: 17/107,108

(22) Filed: Nov. 30, 2020

(65) Prior Publication Data

US 2021/0095263 A1    Apr. 1, 2021

Related U.S. Application Data

(62) Division of application No. 15/956,089, filed on Apr. 18, 2018, now Pat. No. 10,883,090.

(60) Provisional application No. 62/486,606, filed on Apr. 18, 2017.

(51) Int. Cl.
*C12N 15/82* (2006.01)
*C12N 9/10* (2006.01)

(52) U.S. Cl.
CPC ....... *C12N 9/1029* (2013.01); *C12N 15/8255* (2013.01)

(58) Field of Classification Search
None
See application file for complete search history.

(56) References Cited

U.S. PATENT DOCUMENTS

| | | | |
|---|---|---|---|
| 4,490,838 A | 12/1984 | Akira et al. | |
| 5,258,300 A | 11/1993 | Glassman et al. | |
| 5,384,253 A | 1/1995 | Krzyzek et al. | |
| 5,472,869 A | 12/1995 | Krzyzek et al. | |
| 5,489,520 A | 2/1996 | Adams et al. | |
| 5,538,877 A | 7/1996 | Lundquist et al. | |
| 5,538,880 A | 7/1996 | Lundquist et al. | |
| 5,550,318 A | 8/1996 | Adams et al. | |
| 5,641,673 A | 6/1997 | Brand et al. | |
| 5,985,557 A | 11/1999 | Brow et al. | |
| 6,001,567 A | 12/1999 | Brow et al. | |
| 7,705,215 B1 | 4/2010 | Adams et al. | |
| 8,481,593 B2 | 7/2013 | Okombi et al. | |
| 8,569,465 B2 | 10/2013 | Ralph et al. | |
| 9,089,499 B2 | 7/2015 | Okombi et al. | |
| 9,428,763 B2 | 8/2016 | Sanz Molinero | |
| 9,441,235 B2 | 9/2016 | Wilkerson et al. | |
| 9,487,794 B2 | 11/2016 | Wilkerson et al. | |
| 9,493,783 B2 | 11/2016 | Wilkerson et al. | |
| 2006/0159283 A1 | 7/2006 | Alexandrov et al. | |
| 2007/0183996 A1 | 8/2007 | Okombi et al. | |
| 2007/0283460 A9 | 12/2007 | Liu et al. | |
| 2008/0112245 A1 | 5/2008 | Ostermayr et al. | |
| 2011/0237551 A1 | 9/2011 | Okombi et al. | |
| 2013/0272983 A1 | 10/2013 | Okombi et al. | |
| 2015/0020234 A1 | 1/2015 | Wilkerson et al. | |
| 2015/0307892 A1* | 10/2015 | Bartley | C12N 9/1025 800/298 |
| 2015/0376640 A1* | 12/2015 | Shoresh | C12N 15/8271 800/278 |
| 2016/0046955 A1 | 2/2016 | Wilkerson et al. | |
| 2017/0218004 A1 | 8/2017 | Wilkerson et al. | |
| 2018/0298353 A1 | 10/2018 | Beebe et al. | |

FOREIGN PATENT DOCUMENTS

| | | |
|---|---|---|
| EP | 0 154 204 B1 | 2/1985 |
| EP | 0 218 571 A2 | 4/1987 |
| EP | 321 201 A2 | 6/1989 |
| EP | 0 604 662 A1 | 6/1994 |
| EP | 0 672 752 A1 | 9/1995 |
| WO | WO 1995/6128 A2 | 3/1995 |
| WO | WO 2012/012698 A1 | 1/2012 |
| WO | WO 2012/012741 A1 | 1/2012 |
| WO | WO 2013/052660 A1 | 4/2013 |
| WO | WO 2013/090814 A3 | 6/2013 |
| WO | WO 2014/100742 A2 | 6/2014 |

OTHER PUBLICATIONS

Guo et al.(PNAS,101:9205-9210,2004).*
Keskin et al.(ProteinScience,13:1043-1055,2004).*
Thornton et al.(NaturestructuralBiology,structuralgenomicssupplement,Nov. 2000,p. 992).*
McConnel l et al.(Nature,411:709-713,2001).*
Hanzawa et al.(PNAS,102:7748-7753,2005).*
Wishart et al.(JBC,270:26782-26785,1995).*
Nishimura et al.(PlantCellPhysiol.,41(5):583-590,2000).*
Yang et al.(PNAS,98:11438-11443,2001;abstract;pp. 11442-11443).*
Wells (Biochemistry29:8509-8517,1990).*
Ngo et al. (TheProteinFoldingProblemandTertiaryStructurePrediction,K.Merz.,andS.LeGrand(eds.)pp. 492-495,1994).*
Alexandrov et al. (NCBI, GenBank Sequence Accession No. EU970537.1, Published Dec. 10, 2008).
Alexandrov et al. Insights into corn genes derived from large-scale cDNA sequencing, *Plant Mol. Biol.*, (2009) 69 (1-2), 179-194.
Alexandrov et al. (GenBank Sequence Accession No. ACG42655; pp. 1-2; 2008).
Altschul S, Gish W, Miller W, Myers E, Lipman D., Basic local alignment search tool. (1990) J Mol Biol 215(3), 403-410.

(Continued)

*Primary Examiner* — Vinod Kumar
(74) *Attorney, Agent, or Firm* — Daniel A. Blasiole; DeWitt LLP

(57) ABSTRACT

The invention is directed to p-coumaroyl-CoA:monolignol transferase enzymes, nucleic acids encoding p-coumaroyl-CoA:monolignol transferase enzymes, and inhibitory nucleic acids adapted to inhibit the expression and/or translation of p-coumaroyl-CoA:monolignol transferase RNA; expression cassettes, plant cells, and plants that have or encode such nucleic acids and enzymes; and methods of making and using such nucleic acids, enzymes, expression cassettes, cells, and plants.

11 Claims, 12 Drawing Sheets

Specification includes a Sequence Listing.

(56) References Cited

OTHER PUBLICATIONS

An. S.M., et al., Binary ti vectors for plant transformation and promoter analysis, *Methods in Enzymology*. (1987) 153:292.

An. S.M., et al., p-Coumaric acid, a constituent of *Sasa quelpaertensis* Nakai, inhibits cellular melanogenesis stimulated by alpha-melanocyte stimulating hormone, *Brit J Dermatol.*, (2008) 159(2), 292-299.

Bell-Lelong et al., Cinnamate-4-hydroxylase expression in *Arabidopsis*: regulation in response to development and the environment, *Plant Physiol.* (1997) 113, 729-738.

Bevan et al., Structure and transcription of the nopaline synthase gene region of T-DNA, *Nucleic Acid Research*. (1983)11:369-385.

Beuerle and Pichersky, Anal. Biochem. 302(2): 305-12 (2001).

Bodini et al., Quorum sensing inhibition activity of garlic extract and p-coumaric acid, *Lett Appl Microbiol.* (2009) 49(5), 551-555.

Boerjan et al., Lignin biosynthesis, *Annual Reviews in Plant Biology* (2003) 54, 519-546.

Bork et al., Go hunting in sequence databases but watch out for the traps, *TIG*, (1996) 12:425-427.

Cabrita et al., Conversion of hydroxycinnamic acids into volatile phenols in a synthetic medium and red wine by Dekkera bruxellensis. *Ciencia e Tecnologia de Alimentos, Campinas*. (2012) 32(1):106-11.

Camacho et al., BLAST+: architecture and applications, *BMC Bioinformatics*. (2009) 10:421.

Cech Science, The chemistry of self-splicing RNA and RNA enzymes, 236:1532-1539 (1987).

Cech. Ann. Rev. Biochem., Self-splicing of group I introns, 59:543-568 (1990).

Cech, Thomas R. Ribozyme engineering. Curr. Opin. Struct. Biol. 2:605-609 (1992) (No Copy Available).

Chandler et al., Two regulatory genes of the maize anthocyanin pathway are homologous: Isolation of B utilizing R genomic sequences, *The Plant Cell*. (1989) 1:1175-1183.

Christou et al., Stable transformation of soybean by electroporation and root formation from transformed callus, *PNAS*. (1987) 84:3962-3966.

Claverie and States, Information Enhancement Methods for Large Scale Sequence Analysis, *Comput. Chem.* (1993) 17:191-201.

Clough et al., Floral dip: A simplified method for *Agrobacterium*-mediated transformation of *Arabidopsis thaliana*, *Plant Journal* (1998) 16, 735-743.

Coe et al., in *Corn and Corn Improvement*, eds. Sprague, G.F. & Dudley, J.W. (Am. Soc. Agron., Madison, WI), pp. 81-258 (1988) (Book—Copy Not Provided).

Corpet, Multiple sequence alignment with hierarchial clustering, *Nucleic Acids Res.* (1988) 16:10881-90.

Coruzzi et al., Tissue-specific and light-regulated expression of a pea nuclear gene encoding the small subunit of ribulose-1,5-bisphosphate carboxylas, *EMBO J.* (1984) (8):1671-1679).

Couture and Stinchcomb, Anti-gene therapy: the use of ribozymes to inhibit gene function, Trends Genet. 12:510-515 (1996).

Current Protocols in Molecular Biology, Chapters 2 and 19, Ausubel, et al., eds, Greene Publishing and Wiley-Interscience, New York (1995) (Book—Copy Not Provided).

Da Costa Sousa et al., Next-Generation ammonia pretreatment enhances cellulosic biofuel production,. *Energy Environ. Sci.* (2016), 9, 1215-1223.

Dekeyser et al., Transient gene expression in intact and organized rice tissues, *The Plant Cell.* (1990) 2:591-602.

Dellaporta et al., In: *Chromosome Structure and Function: Impact of New Concepts*, 18th Stadler Genetics Symposium, J.P. Gustafson and R. Appels, eds. (New York: Plenum Press) (1988) pp. 263-282.

Doerks et al., Protein annotation: detective work for function prediction, *TIG*, (1998) 14:248-250.

Ebert et al., Identification of an essential upstream element in the nopaline synthase promoter by stable and transient assays, *Proc. Natl. Acad. Sci. USA*. (1987) 84:5745-5749.

Elbashir et al. Duplexes of 21-nucleotide RNAs mediate RNA interference in cultured mammalian cells, (2001) Nature 411:494-498.

Eudes et al., Exploiting members of the BAHD acyltransferase family to synthesize multiple hydroxycinnamate and benzoate conjugates in yeast, *Microb Cell Fact* (2016) 15:198.

Feng and Doolittle, Progressive Sequence Alignment as a Prerequisite to Correct Phylogenetic Trees, *J. Mol. Evol.*, (1987) 25:351-60.

Ferguson et al., Bacterial antimutagenesis by hydroxycinnamic acids from plant cell walls, *Mutation Research-Genetic Toxicology and Environmental Mutagenesis* (2003) 542(1-2), 49-58.

Ferguson et al., Antioxidant and antigenotoxic effects of plant cell wall hydroxycinnamic acids in cultured HT-29 cells. *Molecular Nutrition & Food Research* (2005) 49(6), 585-593.

Fire et al. Potent and specific genetic interference by double-stranded RNA in Caenorhabditis elegans, (1998) Nature 391:806-811.

Gordon Kamm et al., Transformation of maize cells and regeneration of fertile transgenic plants, *The Plant Cell*. (1990) 2:603 618.

Grefen et al., A ubiquitin-10 promoter-based vector set for fluorescent protein tagging facilitates temporal stability and native protein distribution in transient and stable expression studies, *The Plant Journal* (2010) 64, 355-365.

Guo et al. Protein tolerance to random amino acid change, *PNAS* (2004) 101: 9205-9210, 2004.

Grishok et al., Genetic requirements for inheritance of RNAi in C. elegans, Science 287(5462):2494-7 (2000).

Grishok et al. Genes and mechanisms related to RNA interference regulate expression of the small temporal RNAs that control C. elegans developmental timing, (2001) Cell 106:23-34.

Hamilton & Baulcombe, A species of small antisense RNA in posttranscriptional gene silencing in plants, Science 286(5441):950-952 (1999).

Haseloff et al., Simple RNA enzymes with new and highly specific endoribonuclease activities, Nature 334:585-591 (1988).

Hatfield et al., Composition of cell walls isolated from cell types of grain sorghum stems, *J. Sci. Food Agric.* (1999) 79: 891-899.

Hayashimoto et al., A polyethylene glycol-mediated protoplast transformation system for production of fertile transgenic rice plants, *Plant Physiol.* (1990) 93:857-863.

Helm, R. F., Ralph, J., and Hatfield, R.D., Synthesis of feruloylated and p-coumaroylated methyl glycosides. (1992) Carbohydr. Res. 229(1), 183.194.

Henikoff and Henikoff, Amino acid substitution matrices from protein blocks, *Proc. Natl. Acad. Sci. USA* (1989) 89:10915.

Higgins and Sharp, Clustal: a package for performing multiple sequence alignment on a microcomputer, *Gene* (1988) 73:237-44.

Higgins and Sharp, Fast and sensitive multiple sequence alignments on a microcomputer, *Cabios Communications* (1989) 5:151-3.

Hinchee et al., Production of transgenic soybean plants using *Agrobacterium*-mediated DNA transfer, *Bio/Technology*. (1988) 6:915-922.

Holmberg et al., Syringyl methacrylate, a hardwood lignin-based monomer for high-Tg polymeric materials, *ACS Macro Letters* (2016) 5(5), 574-578.

Horsch et al., Somatic embryogenesis from cultured leaf segments of *Zea mays, Science* (1985) 227:1229-1231.

Hsiao & Chiang, Lignins from the Wood of *Aralia Bipinnata, Phytochemistry*, (1995) 39: 899-902.

Huang et al., Parallelization of a local similarity algorithm, *Computer Applications in the Biosciences* (1992) 8:155-65.

Hudspeth et al., Structure and expression of the maize gene encoding the phosphoenolpyruvate carboxylase isozyme involved in C4 photosynthesis, *Plant Molecular Biology*. (1989) 12:579-589.

Ikuta et al., The a-Amylase gene as a marker for gene cloning: Direct screening of recombinant clones, *Bio/Technology* (1990) 8:241-242.

Jefferson, Assaying Chimeric genes in Plants: The GUS Gene Fusion System, *Plant Molecular Biology Reporter* (1987) 5:387-405.

(56) References Cited

OTHER PUBLICATIONS

Kaneko et al., Thermotropic liquid-crystalline polymer derived from natural cinnamoyl biomonomers. (2004) *Macromol Rapid Comm* 25(5), 673-677.
Karimi M, Inze D 5 Depicker A. (2002) Gateway vectors for Agrobacterium-mediated plant transformation. Trends in Plant Science 7(5):193-195).
Karlen, S. D. et al., Monolignol ferulate conjugates are naturally incorporated into plant lignins. *Science Advances* (2016) 2 (10), e1600393:1600391-1600399.
Karlen, S.D., Smith, R.A., Kim, H , Padmakshan, D., Bartuce, A., Mobley, J.K., Free, H.C.A., Smith, B.G., Harris, P.J. and Ralph, J. (2017) Highly decorated lignins occur in leaf base cell walls of the Canary Island date palm Phoenix canadensis. Plant Physiology, 175:1058-1067.
Katz et al., Cloning and expression of the tyrosinase gene from *StreptomyKellces antibioticus* in *Streptomyces lividans, J. Gen. Microbiol.* (1983) 129:2703 2714.
Keller et al., Vascular expression of a bean cell wall glycine-rich protein—glucuronidase gene fusion in transgenic tobacco, *EMBO J.* (1989) 8:1309-1314.
Keskin et al. A new, structurally nonredundant, diverse data set of protein-protein interfaces and its implications, *Protein Science*, (2004) 13:1043-1055.
Ketting et al. Mut-7 of C. elegans, required for transposon silencing and RNA interference, is a homolog of Werner syndrome helicase and RNaseD , (1999) Cell 99:133-141.
Kim et al., Solution-state 2D Nmr of ball-milled plant cell wall gels in DMSO-$d_6$/pyridine-$d_5$, *Org. Biomol. Chem.* (2010) 8(3), 576-591.
Kim et al., Impact of lignin polymer backbone esters on ionic liquid pretreatment of poplar, *Biotechnology for Biofuels* (2017) 10(1):101.
Kim, H., Ralph, J., and Akiyama, T. (2008) Solution-state 2D NMR of Ball-milled Plant Cell Wall Gels in DMSO-d6. BioEnergy Research 1(1 ):56-66.
Kumar, P.; Barrett, D. M.; Delwiche, M. J.; Stroeve, P. (2009) Methods for Pretreatment of Lignocellulosic Biomass for Efficient Hydrolysis and Biofuel Production . Industrial A Engineering Chemistry Research 48(8):3713-3729.
Lawton et al., Expression of a soybean β-conclycinin gene under the control of the Cauliflower Mosaic Virus 35S and 19S promoters in transformed petunia tissues, *Plant Molecular Biology*. (1987) 9:315-324.
Li et al., Time-course accumulation of main bioactive components in the rhizome of Ligusticum chuanxiong, *Planta medica* (2006) 72.03: 278-280.
Li and Zhang, Reverse genetics by fast neutron mutagenesis in higher plants, 2002, Fund Integr Genomics 2:254-258.
Lin and Avery, RNA interference. Policing rogue genes, (1999) Nature 402:128-129.
Liu et al., Application of CRISPR/Cas9 in plant biology, *Acta pharm. Sinica B*, (2017) 7(3): 292-302.
Lu, F., and Ralph, J. Facile synthesis of 4-hydroxycinnamyl p-coumarates. (1998) J. Agr. Food Chem. 46(8), 2911-2913.
Lu et al., Derivatization followed by reductive cleavage (DFRC Method), A new method for lignin analysis: protocol for analysis of DFRC monomers, *Journal of Agricultural and Food Chemistry* (1997) 45, 2590-2592.
Lu et al., Detection and determination of p-coumaroylated units in lignins, *Journal of Agricultural and Food Chemistry* (1999) 47, 1988-1992.
Lu et al., Non-degradative dissolution and acetylation of ball-milled plant cell walls; high-resolution solution-state NMR, *Plant J.* (2003) 35(4), 535-544).
Lu, F., Karlen, S.D., Regner, M., Kim, H., Ralph, S.A., Sun, R.C., Kuroda, K.I., Augustin, M.A., Mawson, R., Sabarez, H., Singh, T., Jimenez-Monteon, G., Hill, S., Harris, PL, Boeijan, W., Mansfield, S.D. and Ralph, J. (2015) Naturally p-hydroxybenzoylated lignins in palms. Bioenerg Res. 8:934-952.
Luterbacher et al., Nonenzymatic sugar production from biomass using biomass-derived γ-valerolactone, *Science* (2014) 343.6168:277-280.
Luterbacher et al., Solvent-enabled nonenyzmatic sugar production from biomass for chemical and biological upgrading, *ChemSusChem* (2015) 8.8:1317-1322.
Luterbacher et al., Lignin monomer production integrated into the γ-valerolactone sugar platform, *Energy and Environmental Science* (2015) 8(9), 2657-2663.
Makino et al., Cell-free protein synthesis for functional and structural studies, *Methods in Molecular Biology* (2014) 1091, 161-178.
Mansfield, S.D., Kim, H., Lu, F. and Ralph, J. (2012) Whole plant cell wall characterization using solution-state 2D-NMR. Nature Protocols, 7:1579-1589.
Martinez et al. Single-stranded antisense siRNAs guide target RNA cleavage in RNAi, Cell 110(5):563 (2002).
Marita et al., Identification and suppression of the p-coumaroyl CoA:hydroxycinnamyl alcohol transferase in *Zea mays* L. *Plant J.* (2014) 78 (5), 850-864.
McCabe et al., Stable transformation of soybean (glycine max) by particle acceleration, *Bio/Technology* (1988) 6:923-926.
McCallum et al. Targeted screening for induced mutations, (2000) Nat Biotech 18:455.
McCallum et al. Targeting induced local lesions IN genomes (TILLING) for plant functional genomics, (2000) Plant Physiol. 123:439-442.
McConnell et al., Role of Phabulosa and Phavoluta in determining radial patterning in shoots, *Nature* (2001) 411:709-713.
McElroy et al., Isolation of an Efficient Actin Promoter for Use in Rice Transformation, *The Plant Cell* (1990) 2:163-171.
Meinkoth and Wahl, Hybridization of Nucleic Acids immobilized on Solid Supports, *Anal. Biochem.* (1984) 138:267-84.
Mellmer et al. Effects of γ-valerolactone in hydrolysis of lignocellulosic biomass to monosaccharides, *Green Chemistry* (2014) 16.11:4659-4662.
Meyer et al., Lignin monomer composition is determined by the expression of a cytochrome P450-dependent monooxygenase in *Arabidopsis, Proc. Natl. Acad. Sci. USA* (1998) 95(12), 6619-6623.
Montgomery et al. RNA as a target of double-stranded RNA-mediated genetic interference in Caenorhabditis elegans, (1998) Proc. Natl. Acad. Sci. USA. 95:15502-15507.
Murakami et al., The bialaphos biosynthetic genes of Streptomyces hygroscopicus: Molecular cloning and characterization of the gene cluster, *Mol. Gen. Genet.* (1986) 205:42 50.
Nagata et al., Synthesis and characterization of photocrosslinkable biodegradable Polymers derived from 4-hydroxycinnamic acid, *Macromol Biosci* (2003) 3(8), 412-419.
Nambudiri et al., Conversion of p-coumarate into caffeate by Streptomyces nigrifaciens. Purification and properties of the hydroxylating enzyme,. *Biochem J.* (1972)130(2):425-33.
Needleman and Wunsch, A General Method Applicable to the Search for Similarities in the Amino Acid Sequence of Two Proteins, *J. Mol. Biol.* (1970) 48:443-53.
Ngo et al., The Protein Folding Problem and Tertiary Structure Prediction, K. Merz., and S. Le Grand (eds.) (1994) pp. 492-495.
Niedz et al., Green fluorescent protein: an in vivo reporter of plant gene expression, *Plant Cell Reports* (1995) 14:403.
Nishimura et al., Over-Expression of Tobacco knotted1-Type Class1 Homeobox Genes Alters Various Leaf Morphology, *Plant Cell Physiol.*, (2000) 41(5):583-590.
Odell et al., Identification of DNA sequences required for activity of the cauliflower mosaic virus 35S promoter, *Nature* (1985) 313:810-812.
Ow et al., Transient and stable expression of the firefly luciferase gene in plant cells and transgenic plants, *Science* (1986) 234:856-859.
Patterson et al., Hypothetical protein SORBIDRAFT_09g002910 [Sorghum bicolor] (NCBI, Gen Bank Sequence Accession No. XP_002439238.1 Published Jul. 13, 2009).
Paula et al., Lignans from *Ochroma lagopus* Swartz, *Tetrahedron* (1995) 51.45:12453-12462.
PCT International Search Report and Written Opinion, dated Mar. 25, 2020, PCT/US19/60554.

(56) References Cited

OTHER PUBLICATIONS

Pearson and Lipman, Improved tools for biological sequence comparison, *Proc. Natl. Acad. Sci. USA* (1988) 85:2444.
Pearson, Using the FASTA Program to Search Protein and DNA Sequence Databases, *Meth. Mol. Biol.* (1994) 24:307-31.
Petrik et al., p-Coumaroyl-CoA:Monolignol Transferase (PMT) acts specifically in the lignin biosynthetic pathway in Brachypodium distachyon, *The Plant Journal* (2014) 77 (5), 713-726.
Petrik et al. BdCESA7, BdCESA8, and BdPMT utility promoter Reconstructs for targeted expression to secondary cell-wall-forming cells of grasses, (2016) *Frontiers in Plant Science* (2016) 7, 1-14.
Potrykus et al., Direct gene transfer to cells of a graminaceous monocot, *Mol. Gen. Genet.* 199:183-188 (1985).
Potrykus I., Gene transfer to cereals: an assessment, *Trends Biotech.* (1989) 7:269-273.
Prasher et al., Cloning and expression of the cDNA Coding for Aequorin, a Bioluminescent Calcium-Binding Protein, *Biochem. Biophys. Res. Comm.* (1985) 126:1259-1268.
Ralph et al., Pathway of p-coumaric acid incorporation into maize lignin as revealed by NMR, *J. Am. Chem. Soc.* (1994) 116: 9448-9456.
Ralph et al., Lignins: natural polymers from oxidative coupling of 4-hydroxyphenylpropanoids, *Phytochem. Revs.* (2004) 3(1), 29-60.
Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK (Book—Copy Not Provided).
Razzaghi-Asl et al., Antioxidant properties of hydroxycinnamic acids: A review of structure-activity relationships, *Current Medicinal Chemistry* (2013) 20(36), 4436-4450.
Regner, M., Bartuce, A., Padmakshan, D., Ralph, J. and Karlen, S.D. (2018) Reductive cleavage method for quantitation of monolignols and low-abundance monolignol conjugates. ChemSusChem 11:1600-1605.
Rinaldi et al. (2016) Paving the way for lignin valorisation: Recent Advances in Bioengineering, Biorefining and Catalysis. Angew Chem Int Ed Engl. 55(29):8164-8215).
Sambrook et al. (Molecular Cloning: A Laboratory Manual. Second Edition (Cold Spring Harbor, NY: Cold Spring Harbor Press (1989) (Book—Copy Not Provided).
Sambrook et al.,Molecular Cloning: A Laboratory Manual. Third Edition (Cold Spring Harbor, NY: Cold Spring Harbor Press (2000) (Book—Copy Not Provided).
Santoro et al., A high-throughput platform for screening milligram quantities of plant biomass for lignocellulose digestibility, *Bioenergy Research* (2010) 3(1), 93-102.
Sawasaki et al., "Construction of an efficient expression vector for coupled transcription/translation in a wheat germ cell-free system." *Nucleic acids Symposium Series*. (2000) vol. 44. No. 1. Oxford University Press.
Seca et al., Phenolic constituents from the core of kenaf (Hibiscus cannabinus), *Phytochemistry* (2001) 56.7:759-767.
Sengupta-Gopalan, C., Developmentally regulated expression of the bean β-phaseolin gene in tobacco seed, *Proc. Natl. Acad. Sci. USA.* (1985) 83:3320-3324.
Shuai et al., Formaldehyde stabilization facilitates lignin monomer production during biomass depolymerization, *Science* (2016) 354(6310), 329-333.
Sibout et al., Structural redesigning *Arabidopsis* lignins into alkali-soluble lignins through the expression of p-coumaroyl-CoA:monolignol transferase PMT. *Plant Physiol.* (2016) 170 (3), 1358-66.
Sharp, RNAi and double-strand RNA, (1999) Genes Dev. 13:139-141.
Sharp and Zamore, Molecular biology. RNA interference, (2000) Science 287:2431-2433.
Smith, D.C.C. (1955a) Ester groups in lignin. Nature 176:267-268.
Smith, D.C.C. (1955b) p-Hydroxybenzoates groups in the lignin of Aspen (*Populus tremula*) Journal of the Chemical Society 2347).
Sievers et al., Fast, scalable generation of high-quality protein multiple sequence alignments using Clustal Omega. *Mol Syst Biol.* (2011) 7:539.
Smith and Waterman, Comparison of Biosequences, (1981) *Adv. Appl. Math* 2:482.
Smith et al., The challenges of genome sequence annotation or "The devil is in the details", *Nature Biotechnology* (1997) 15:1222-1223.
Smith et al., Engineering monolignol p-coumarate conjugates into poplar and arabidopsis lignins, *Plant Physiology* (2015) 169, 2992-3001.
Smith et al., Defining the diverse cell populations contributing to lignification in *Arabidopsis thaliana* 13 stems, *Plant Physiology* (2017) 174, 1028-1036.
Stalker et al., Herbicide resistance in transgenic plants expressing a bacterial detoxification gene, *Science* (1988) 242:419-423.
Stewart et al., The effects on lignin structure of overexpression of ferulate 5-hydroxylase in hybrid poplar, *Plant Physiol.* (2009) 150(2), 621-635.
Stiefel et al., Expression of a maize cell wall hydroxyproline-rich glycoprotein gene in early leaf and root vascular differentiation, *The Plant Cell.* (1990) 2:785-793.
Sullivan et al., Isolation and characterization of a maize chlorophyll a/b binding protein gene that produces high levels of mRNA in the dark, *Mol. Gen. Genet.* (1989) 215:431.
Sutcliffe, J. G., Complete nucleotide sequence of the *Escherichia coli* plasmid pBR322, *Proc. Natl. Acad. Sci. USA.* (1978) 75:3737-3741.
Tabara et al. The rde-1 gene, RNA interference, and transposon silencing in C. elegans (1999) Cell 99:123-132.
Thillet et al., Site-directed mutagenesis of mouse dihydrofolate reductase. Mutants with increased resistance to methotrexate and trimethoprim, *J. Biol. Chem.* (1988) 263:12500-12508.
Thornton et al., From structure to function: Approaches and limitations, *Nature structural Biology, structural genomics supplement,* (Nov. 2000).
Tijssen, Laboratory Techniques in Biochemistry and Molecular Biology—Hybridization With Nucleic Acid Probes, part 1, chapter 2, "Overview of principles of hybridization and the strategy of nucleic acid probe assays," Elsevier, N.Y. (1993) (Book—Copy Not Provided).
Tuominen et al., Differential phylogenetic expansions in BAHD acyltransferases across five angiosperm taxa and evidence of divergent expression among Polulus paralogues, *BMC Genomics*, (2011) 12-236.
Twell et al., Transient Expression of Chimeric Genes Delivered into Pollen by Microprojectile Bombardment, *Plant Physiol.* (1989) 91:1270 1274.
UNIPROTKB—A0A2K2CDA7 (A0A2K2CDA7_POPTR), Mar. 28, 2018 [online]. [Retrieved on Jan. 24, 2020]. Retrieved from the internet ,https://www.uniprot.org/uniprot/A0A2K2CDA7>.
Upton et al., Strategies for the conversion of lignin to high-value polymeric materials: Review and perspective, *Chemical Reviews* (2016) 116(4), 2275-2306.
Vanholme et al., Lignin engineering, *Curr. Opin. Plant Biol.* (2008) 11(3), 278-285.
Vanholme et al., Lignin biosynthesis and structure, *Plant Physiol.* (2010) 153(3), 895-905.
Vanholme et al., Metabolic engineering of novel lignin in biomass crops, *New Phytol.* (2012) 196(4), 978-1000.
Walker et al., DNA sequences required for anaerobic expression of the maize alcohol dehydrogenase 1 gene, *Proc. Natl. Acad. Sci. USA.* (1987) 84:6624-6628.
Wang et al., Characterization of cis-acting elements regulating transcription from the promoter of a constitutively active rice actin gene, *Mol. Cell. Biol.* (1992) 12:3399.
Ware NCBI, GenBank Sequence Accession No. AQK78565.1; Published (Feb. 7, 2017).
Wells, Additivity of Mutational Effects in Proteins, *Biochemistry* (1990) 29:8509-8517.
Wilkerson et al., (GenBank Sequence Accession No. AHL24755; pp. 1-2; 2014).

(56) References Cited

OTHER PUBLICATIONS

Wilkerson et al., Monolignol ferulate transferase introduces chemically labile linkages into the lignin backbone, *Science* (2014) 344:91.

Wishart et al., A single Mutation Converts a Novel Phosphotyrosine Binding Domain into a Dual-specificity Phosphatase, *JBC*, (1995) 270:26782-26785.

Withers et al., Identification of a grass-specific enzyme that acylates monolignols with p-coumarate, *Journal of Biological Chemistry* (2012) 287, 8347-8355.

Wooten and Federhen, Statistics of Local Complexity in Amino Acid Sequences and Sequence Databases, *Comput. Chem.* (1993) 17:149-63.

Yang et al., Maize sucrose synthase-1 promoter directs phloem cell-specific expression of Gus gene in transgenic tobacco plants, *Proc. Natl. Acad. Sci. USA.* (1990) 87:4144-4148.

Yang et al., Expression of the REB transcriptional activator in rice grains improves the yield of recombinant proteins whose genes are controlled by a Reb- responsive promoter, *PNAS*, (2001) 98:11438-11443.

Yelle et al., Characterization of non-derivatized plant cell walls using high-resolution solution-state NMR spectroscopy, *Magn. Reson. Chem.* (2008) 46(6), 508-517.

Zukowski et al., Chromogenic identification of genetic regulatory signals in *Bacillus subtilis* based on expression of a cloned Pseudomonas gene, *Proc. Natl. Acad. Sci. USA.* (1983) 80:1101.

Hanzawa, et al. "A single amino acid converts a repressor to an activator of flowering," PNAS, 102, 2005, 7748-7753.

Paterson et al. NCBI, GenBank Sequence Accession No. XP_002441966.1, Published Jul. 13, 2009.

U.S. Appl. No. 15/956,089, John Ralph, filed Apr. 18, 2018.

* cited by examiner

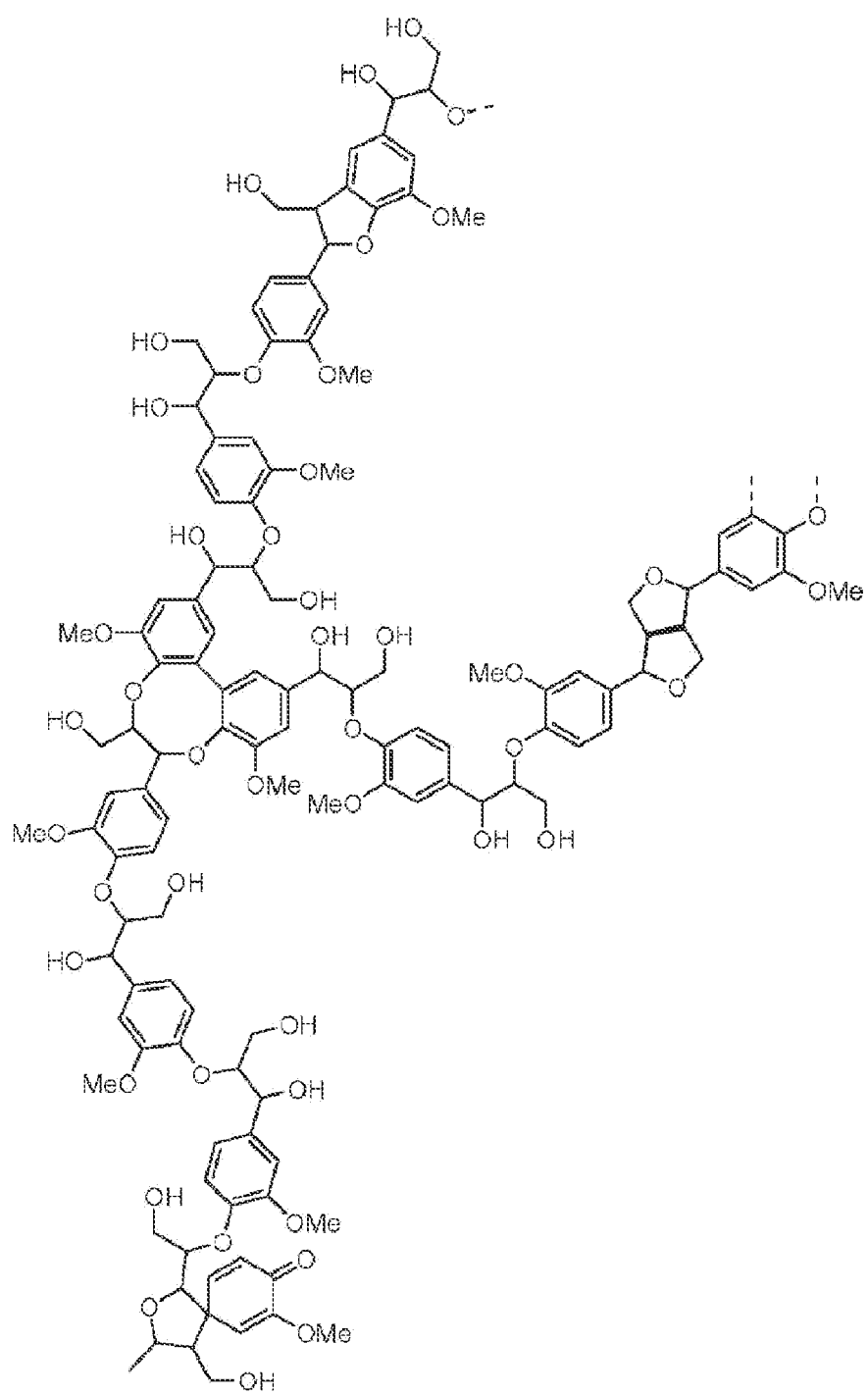
*FIG. 1A1*

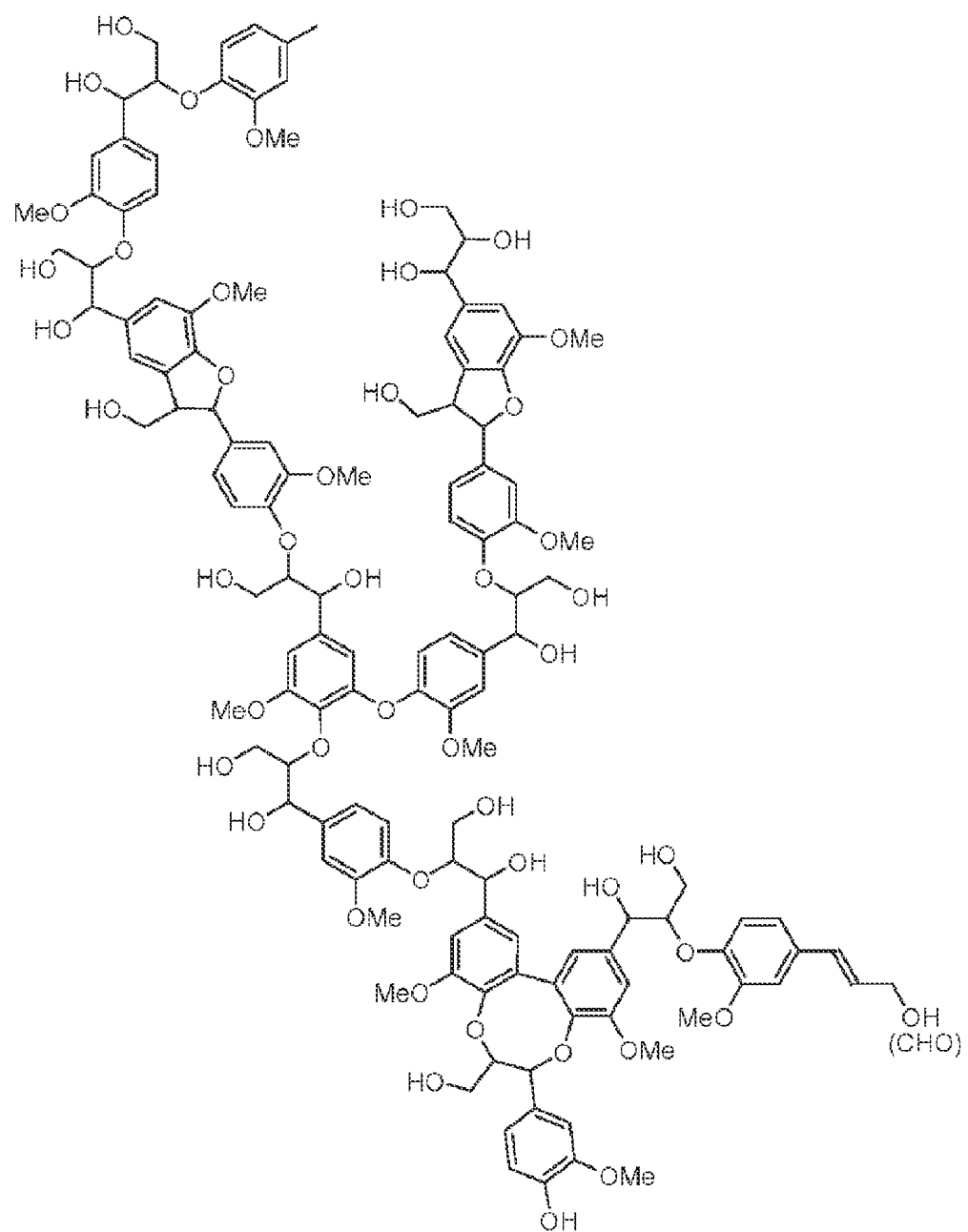
*FIG. 1A2*

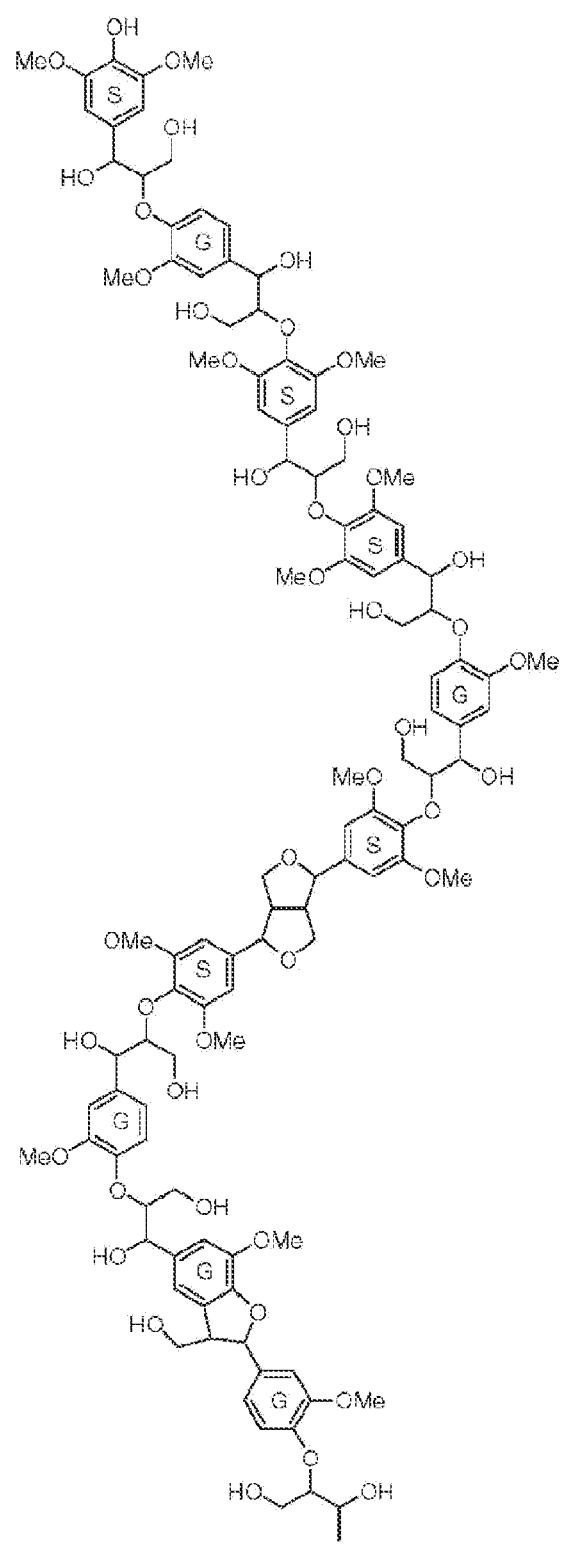
*FIG. 1B1*

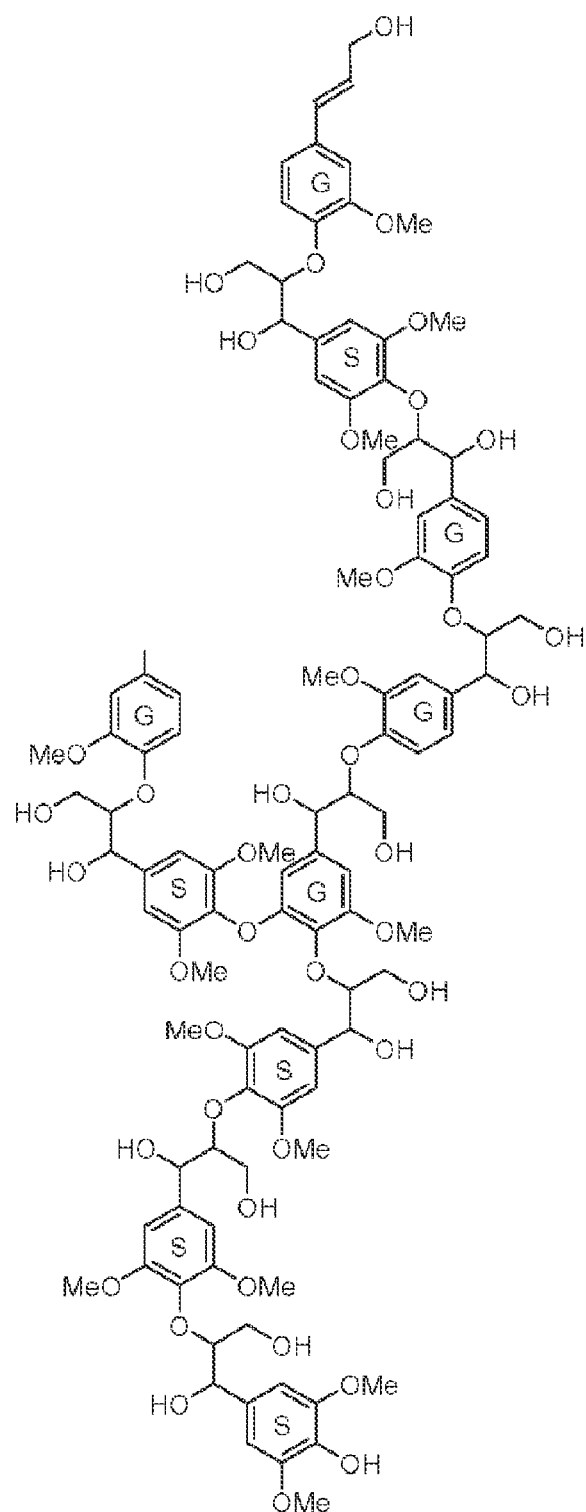
FIG. 1B2 monolignols
(ML)

*p*-coumaroyl-CoA
(*p*CA-CoA)

feruloyl-CoA
(FA-CoA)

monolignol *p*-coumarate
(ML-*p*CA)

monolignol ferulate
(ML-FA)

P-COUMAROYL-CoA:MONOLIGNOL TRANSFERASES

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The invention is directed to p-coumaroyl-CoA:monolignol transferase enzymes, nucleic acids encoding p-coumaroyl-CoA:monolignol transferase enzymes, and inhibitory nucleic acids adapted to inhibit the expression and/or translation of p-coumaroyl-CoA:monolignol transferase RNA; expression cassettes, plant cells, and plants that have or encode such nucleic acids and enzymes; and methods of making and using such nucleic acids, enzymes, expression cassettes, cells, and plants.

BACKGROUND

Lignin is an important cell wall component that provides structural support to plants and is needed for plant vascular tissue function. Lignin is also a source of organic material for the synthesis of chemicals. Lignin is one of the most abundant organic polymers on Earth, constituting about 30% of non-fossil organic carbon and from a quarter to a third of the dry mass of wood. Because the chemical structure of lignin is difficult to degrade by chemical and enzymatic means, lignin makes the task of producing paper and biofuels from plant cell walls difficult. Modifying lignin to make it more amenable to degradation or suitable for the production of certain chemicals is desirable.

SUMMARY OF THE INVENTION

The invention relates to the identification and isolation of new acyltransferase nucleic acids and polypeptides. The acyltransferases are p-coumaroyl-CoA:monolignol transferases (also called PMTs, or monolignol coumarate transferases) that produce monolignol coumarates. The p-coumaroyl-CoA:monolignol transferases can be used for making plants that contain modified lignin. The modified lignin is amenable to degradation and production of commodity chemicals.

One aspect of the invention is an isolated nucleic acid encoding a p-coumaroyl-CoA:monolignol transferase polypeptide with a SEQ ID NO:2 or SEQ ID NO:4 sequence.

Such p-coumaroyl-CoA:monolignol transferases can catalyze the synthesis of monolignol coumarate(s) from monolignol(s) and coumaroyl-CoA. For example, the monolignol can be coniferyl alcohol, p-coumaryl alcohol, sinapyl alcohol, or a combination thereof, and the p-coumaroyl-CoA:monolignol transferase can, for example, synthesize coniferyl coumarate, p-coumaryl coumarate, sinapyl coumarate or a combination thereof. p-Coumaroyl-CoA:monolignol transferases with SEQ ID NO:2 or SEQ ID NO:4 sequences are unique in that they are selective for generating monolignol coumarates and have no relevant activity in generating monolignol ferulates. This is important as these transferases can be used to generate modified lignin containing a higher proportion of monolignol coumarates without conducting other extraneous activity.

In some embodiments, the p-coumaroyl-CoA:monolignol transferase nucleic acid encodes a p-coumaroyl-CoA:monolignol transferase polypeptide with a SEQ ID NO:2 or SEQ ID NO:4 sequence. In other embodiments, the nucleic acids can, for example, encode a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO. 4 amino acid sequence.

Another aspect of the invention is a transgenic plant cell comprising an isolated nucleic acid encoding a p-coumaroyl-CoA:monolignol transferase. The nucleic acid can include any of the p-coumaroyl-CoA:monolignol transferase nucleic acids described herein. For example, the nucleic acid can include a nucleic acid segment that can selectively hybridize to a DNA with a SEQ ID NO:1 or SEQ ID NO:3 sequence, or a nucleic acid that encodes a SEQ ID NO:2 or SEQ ID NO. 4 amino acid sequence, or a nucleic acid that encodes a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO. 4 amino acid sequence.

Another aspect of the invention is an expression cassette comprising one of the p-coumaroyl-CoA:monolignol transferase nucleic acids described herein that is operably linked to a promoter functional in a host cell. Such a nucleic acid can include a nucleic acid segment that can selectively hybridize to a DNA with a SEQ ID NO:1 or SEQ ID NO:3 sequence, or a nucleic acid that encodes a SEQ ID NO:2 or SEQ ID NO:4 amino acid sequence, or a nucleic acid that encodes a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO:4 amino acid sequence. The expression cassette can further comprise a selectable marker gene. In some embodiments, the expression cassette further comprises plasmid DNA. For example, the expression cassette can be within an expression vector. Promoters that can be used within such expression cassettes include promoters functional during plant development or growth.

Another aspect of the invention is a plant cell that includes an expression cassette comprising one of the p-coumaroyl-CoA:monolignol transferase nucleic acids described herein that is operably linked to a promoter functional in a host cell. Such a nucleic acid can include a nucleic acid segment that can selectively hybridize to a DNA with a SEQ ID NO:1 or SEQ ID NO:3 sequence, or a nucleic acid that encodes a SEQ ID NO:2 or SEQ ID NO:4 amino acid sequence, or a nucleic acid that encodes a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO:4 amino acid sequence. The plant cell can be a monocot cell. The plant cell can also be a gymnosperm cell. For example, the plant cell can be a maize, grass or softwood cell. In some embodiments, the plant cell is a dicot cell. For example, the plant cell can be a hardwood cell.

Another aspect of the invention is a plant that includes an expression cassette comprising one of the p-coumaroyl-CoA:monolignol transferase nucleic acids described herein that is operably linked to a promoter functional in a host cell.

Such a plant can be a monocot. Such a nucleic acid can include a nucleic acid segment that can selectively hybridize to a DNA with a SEQ ID NO:1 or SEQ ID NO:3 sequence, or a nucleic acid that encodes a SEQ ID NO:2 or SEQ ID NO. 4 amino acid sequence, or a nucleic acid that encodes a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO:4 amino acid sequence. The plant can also be a gymnosperm. For example, the plant can be a maize, grass or softwood plant. In some embodiments, the plant is a dicot plant. For example, the plant can be a hardwood plant.

Another aspect of the invention is a method for incorporating monolignol coumarates into lignin of a plant that includes:

a) stably transforming plant cells with the expression cassette comprising one of the p-coumaroyl-CoA: monolignol transferase nucleic acids described herein to generate transformed plant cells;

b) regenerating the transformed plant cells into at least one transgenic plant, wherein p-coumaroyl-CoA: monolignol transferase is expressed in at least one transgenic plant in an amount sufficient to incorporate monolignol coumarates into the lignin of the transgenic plant.

For example, such a nucleic acid can be a nucleic acid that can selectively hybridize to a DNA with a SEQ ID NO:1 or SEQ ID NO:3 sequence, or a nucleic acid that encodes a SEQ ID NO:2 or SEQ ID NO:4 amino acid sequence, or a nucleic acid that encodes a p-coumaroyl-CoA:monolignol transferase that can catalyze the synthesis of monolignol coumarate(s) from a monolignol(s) and coumaroyl-CoA with at least about 50%, of the activity of a p-coumaroyl-CoA:monolignol transferase with the SEQ ID NO:2 or SEQ ID NO. 4 amino acid sequence. The method can be used to generate a transgenic plant that is fertile. The method can further include recovering transgenic seeds from the transgenic plant, wherein the transgenic seeds include the nucleic acid encoding a p-coumaroyl-CoA:monolignol transferase. The plant containing monolignol coumarates within its lignin can be a monocot. The plant can also be a gymnosperm. For example, the plant can be a maize, grass or softwood plant. In some embodiments, the plant is a dicot plant. For example, the plant can also be a hardwood plant. Such a method can further include stably transforming the plant cell(s) or the plant with at least one selectable marker gene. The selectable marker can be linked or associated with the expression cassette.

In some embodiments, the lignin in the plant that has the nucleic acid encoding a p-coumaroyl-CoA:monolignol transferase can include at least 1% (wt %) monolignol coumarate. In other embodiments, the lignin in the plant can include at least 5% (wt %) monolignol coumarate, or at least 10% (wt %) monolignol coumarate, or at least 20% (wt %) monolignol coumarate, or at least 30% (wt %) monolignol coumarate, or at least 40% (wt %) monolignol coumarate, or at least 50% (wt %) monolignol coumarate, or at least 60% (wt %) monolignol coumarate, or at least 70% (wt %) monolignol coumarate, or at least 80% (wt %) monolignol coumarate, or at least 90% (wt %) monolignol coumarate, or about 100% (wt %) monolignol coumarate. In further embodiments, the lignin in the plant includes about 1-50% monolignol coumarate, or about 2-55% monolignol coumarate.

In some embodiments, the lignin in the plant that has the nucleic acid encoding a p-coumaroyl-CoA:monolignol transferase can be derived from about or at least 1% (mole %) monolignol coumarate. In other embodiments, the lignin in the plant can include about or at least 5% (mole %) monolignol coumarate, or about or at least 10% (mole %) monolignol coumarate, or about or at least 20% (wt %) monolignol coumarate, or about or at least 30% (mole %) monolignol coumarate, or about or at least 40% (mole %) monolignol coumarate, or about or at least 50% (mole %) monolignol coumarate, or about or at least 60% (mole %) monolignol coumarate, or about or at least 70% (mole %) monolignol coumarate, or about or at least 80% (mole %) monolignol coumarate, or about or at least 90% (mole %) monolignol coumarate, or about 100% (mole %) monolignol coumarate.

The method for incorporating monolignol coumarates into lignin of a plant can also include breeding the fertile transgenic plant to yield a progeny plant, where the progeny plant has an increase in the percentage of monolignol coumarates in the lignin of the progeny plant relative to the corresponding untransformed plant.

Another aspect of the invention is a lignin isolated from the transgenic plant comprising any of the p-coumaroyl-CoA:monolignol transferase nucleic acids described herein. Another aspect of the invention is a woody material isolated from the transgenic plant comprising any of the p-coumaroyl-CoA:monolignol transferase nucleic acids described herein. The lignin or woody tissue can include any of the nucleic acids described herein that encode a p-coumaroyl-CoA:monolignol transferase. In other embodiments, the lignin or woody tissue can include any of the p-coumaroyl-CoA:monolignol transferase amino acid or polypeptide sequences described herein.

Another aspect of the invention is a method of making a product from a transgenic plant comprising: (a) providing a transgenic plant that includes one of the isolated nucleic acids described herein that encodes a p-coumaroyl-CoA: monolignol transferase; and (b) processing the transgenic plant's tissues under conditions sufficient to digest the lignin; to thereby generate the product from the transgenic plant, wherein the transgenic plant's tissues comprise lignin having an increased percent of monolignol coumarates relative to a corresponding untransformed plant. Such a corresponding untransformed plant is typically a plant of the same species, strain and/or accession as the transformed plant. The conditions sufficient to digest the lignin can include conditions sufficient to cleave ester bonds within monolignol coumarate-containing lignin. In some embodiments, the conditions sufficient to digest the lignin include mildly alkaline conditions. In some embodiments, the conditions sufficient to digest the lignin include contacting the transgenic plant's tissues with ammonia for a time and a temperature sufficient to cleave ester bonds within monolignol coumarate-containing lignin. In some embodiments, the conditions sufficient to digest the lignin include acidic conditions.

Another aspect of the invention is an isolated nucleic acid encoding a p-coumaroyl-CoA:monolignol transferase, wherein the nucleic acid can selectively hybridize to a DNA with a SEQ ID NO:1 or SEQ ID NO:3 sequence. For example, the nucleic acid can selectively hybridize to a DNA with a SEQ ID NO:1 or SEQ ID NO:3 sequence under stringent hybridization conditions. In some embodiments, the stringent hybridization conditions comprise a wash in 0.1×SSC, 0.1% SDS at 65° C. Such an isolated nucleic acid can have at least about 79%, at least about 80%, at least about 90%, or at least 95% sequence identity with SEQ ID NO:1 or SEQ ID NO:3. In some embodiments, the isolated nucleic acid with the SEQ ID NO:1 or SEQ ID NO:3 sequence encodes a p-coumaroyl-CoA:monolignol transferase.

Other aspects of the invention include inhibitory nucleic acids adapted to inhibit expression and/or translation of a p-coumaroyl-CoA:monolignol transferase mRNA; expression cassettes, plant cells, and plants comprising the inhibitory nucleic acids; methods pertaining to the use of the inhibitory nucleic acids; transgenic plants comprising a knockdown or knockout of the plant's endogenous p-coumaroyl-CoA:monolignol transferase; and other aspects as described in the following statements of the invention and elsewhere herein. These aspects of the invention can be carried out by adapting the descriptions provided in U.S. Pub. No. 2016/0046955, which is attached hereto and is incorporated herein by reference, to the sequences described herein.

Therefore, the invention embraces p-coumaroyl-CoA: monolignol transferase enzymes, nucleic acids encoding or inhibiting expression of p-coumaroyl-CoA:monolignol transferase enzymes, as well as expression cassettes, plant cells, and plants that have or encode such nucleic acids and enzymes, and methods of making and using such nucleic acids, polypeptides, expression cassettes, cells, and plants.

BRIEF DESCRIPTION OF THE DRAWINGS

FIGS. 1A1, 1A2, 1B1 and 1B2 illustrate structural models for some types of lignin polymers. FIGS. 1A1 and 1A2 show examples of lignin structures that may be found in a softwood (spruce). FIGS. 1B1 and 1B2 show examples of lignin structures that may be present in a hardwood (poplar). [Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK]. The softwood lignin is generally more branched and contains a lower proportion of β-ether units. Note that each of these structures represents only one of billions of possible isomers [Ralph, J., Lundquist, K., Brunow, G., Lu, F., Kim, H., Schatz, P. F., Marita, J. M., Hatfield, R. D., Ralph, S. A., Christensen, J. H., and Boerjan, W. Lignins: natural polymers from oxidative coupling of 4-hydroxyphenylpropanoids. (2004) *Phytochem. Revs.* 3(1), 29-60]. Thus, these structures are merely illustrative of some of the linkage types that may be present different lignins. An "S" within a ring indicates a syringyl unit while a "G" within a unit indicates a guaiacyl unit.

FIG. 2A shows the structure of sinapyl alcohol as a possible reactant. Coniferyl alcohol, another possible reactant, lacks one of the two methoxy groups present on sinapyl alcohol. p-Hydroxycinnamyl alcohol (p-coumaryl alcohol), another possible reactant, lacks both of the two methoxy groups present on sinapyl alcohol. FIG. 2B shows the structure of p-coumaroyl-CoA, another possible reactant. FIG. 2C shows the structure of feruloyl-CoA, another possible reactant. FIG. 2D shows the structure of sinapyl p-coumarate as a possible product resulting from the conjugation of sinapyl alcohol with p-coumaryl-CoA. Coniferyl p-coumarate, a possible product resulting from the conjugation of coniferyl alcohol with p-coumaryl-CoA, lacks one of the two methoxy groups present on sinapyl p-coumarate. p-Hydroxycinnamyl coumarate (p-coumaryl coumarate), a possible product resulting from the conjugation of p-hydroxycinnamyl alcohol and p-coumaryl-CoA, lacks both of the two methoxy groups present on sinapyl p-coumarate. FIG. 2E shows the structure of sinapyl ferulate as a possible product resulting from the conjugation of sinapyl alcohol with feruloyl-CoA. Coniferyl ferulate, a possible product resulting from the conjugation of coniferyl alcohol with feruloyl-CoA, lacks one of the two methoxy groups present on sinapyl ferulate. p-Hydroxycinnamyl ferulate (p-coumaryl ferulate), a possible product resulting from the conjugation of p-hydroxycinnamyl alcohol and feruloyl-CoA, lacks both of the two methoxy groups present on sinapyl ferulate.

Figure 2A:
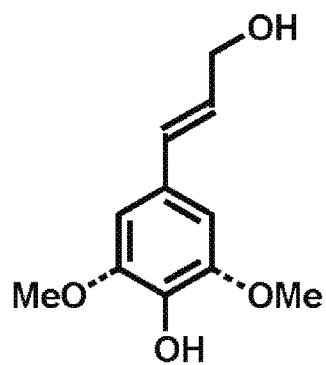
FIGS. 2A-2E show the structures of possible reactants and products of the activity of certain PMT enzymes.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and does not limit the scope of the invention.

DETAILED DESCRIPTION OF THE INVENTION

The invention provides nucleic acids and methods useful for altering lignin structure and/or the lignin content in plants. Plants with such altered lignin structure/content are more easily or economically processed into useful products such as biofuels, paper, or commodity chemicals.

Acyl-CoA Dependent Acyltransferases

Plant acyl-CoA dependent acyltransferases constitute a large but specific protein superfamily, named BAHD. Members of this family take an activated carboxylic acid (i.e., a CoA thioester form of the acid) as an acyl donor and either an alcohol or, more rarely, a primary amine, as an acyl acceptor and catalyze the formation of an ester or an amide bond, respectively. The acyl donors and acyl acceptors that act as substrates by BAHD acyltransferases are quite diverse, and different BAHD family members exhibit a range of substrate specificities.

The invention relates to new BAHD acyltransferase nucleic acids and enzymes that enable the production of transgenic plants with altered lignin. The BAHD nucleic acids can be used in the expression cassettes, expression vectors, transgenic plant cells, transgenic plants, and transgenic seeds as described herein. The BAHD nucleic acids and encoded proteins are isolated or heterologous nucleic acids or proteins. The term "isolated" when used in conjunction with a nucleic acid or polypeptide, refers to a nucleic acid segment or polypeptide that is present in a form or setting that is different from that in which it is found in nature. For example, an isolated nucleic acid or an isolated polypeptide is identified and separated from at least one contaminant nucleic acid or polypeptide with which it is ordinarily associated in its natural state. In contrast, native nucleic acids, such as DNA, RNA and polypeptides are found in the state they exist in nature. The term "heterologous" when used in reference to a nucleic acid refers to a nucleic acid segment that has been manipulated in some way. For example, a heterologous nucleic acid includes a nucleic acid segment from one species that has been introduced into another species. A heterologous nucleic acid also includes a nucleic acid segment that is native to an organism that has been altered in some way (e.g., mutated, multiple copies are added, the heterologous nucleic acid is linked to a non-native promoter or enhancer sequence, etc.). A heterologous nucleic acid also includes a nucleic acid comprising a combination of genetic elements not occurring in nature. Non-limiting examples of such genetic elements include coding sequences, promoters, enhancers, ribosome binding sites (e.g., Shine Dalgarno sequences, Kozak sequences), etc. The term "heterologous" can also refer to any such individual genetic element when included in such a non-naturally occurring combination. Heterologous nucleic acids can include plant nucleic acid segments such as cDNA forms of a plant gene where the cDNA sequences are expressed in a sense direction to produce mRNA. In some embodiments, heterologous nucleic acids can be distinguished from endogenous plant genes in that the heterologous nucleic acid segments are joined to nucleotide sequences comprising regulatory elements such as promoters that are not found naturally associated with the endogenous gene in its natural chromosome. In some embodiments, heterologous nucleic acid can be distinguished from endogenous plant genes in that the heterologous nucleic acid segments express the encoded protein (or portion of a protein) in parts of the plant where the protein (or portion thereof) is not normally expressed. The term "cDNA" refers to any DNA that includes a coding sequence for a polypeptide and lacks one or more introns present in naturally occurring genomic DNA also comprising that coding sequence, regardless of whether or not the cDNA is directly generated from mRNA.

Feruloyl-CoA:monolignol transferases constitute one type of BAHD acyltransferases. These acyltransferases synthesize monolignol ferulates from any of three monolignols (p-coumaryl, coniferyl, and sinapyl alcohols). For example, feruloyl-CoA:monolignol transferases can synthesize coniferyl ferulate from coniferyl alcohol and feruloyl-CoA, as shown below.

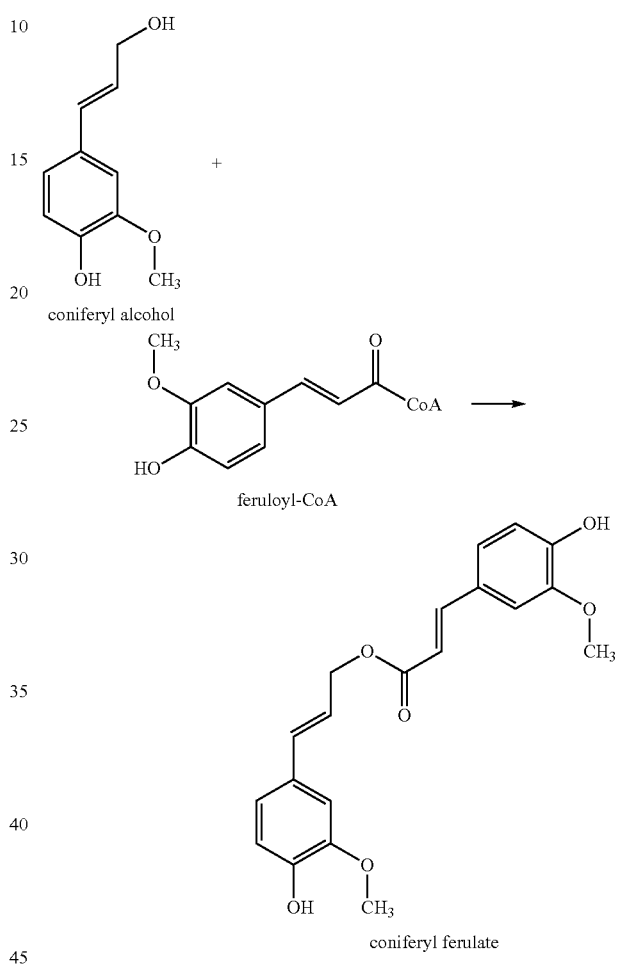

The feruloyl-CoA:monolignol transferases enable production of plants with lignin that is readily cleaved and/or removed, for example, because the lignin in these plants contains monolignol ferulates such as coniferyl ferulate (CAFA). See Karlen, S. D.; Zhang, C.; Peck, M. L.; Smith, R. A.; Padmakshan, D.; Helmich, K. E.; Free, H. C. A.; Lee, S.; Smith, B. G.; Lu, F.; Sedbrook, J. C.; Sibout, R.; Grabber, J. H.; Runge, T. M.; Mysore, K. S.; Harris, P. J.; Bartley, L. E.; Ralph, J., Monolignol ferulate conjugates are naturally incorporated into plant lignins. *Science Advances* 2016, 2 (10), e1600393.

The terms "feruloyl-CoA:monolignol transferase(s)" and "monolignol ferulate transferase(s)" are used interchangeably herein.

Exemplary feruloyl-CoA:monolignol transferases are described in U.S. Appl. 62/481,281, U.S. Pat. Nos. 9,441,235, 9,487,794, 9,493,783, U.S. Pub. 2015/0020234A1, U.S. Pub. 2015/0307892A1, WO 2012/012698A1, WO 2012/012741A1, and WO 2013/052660A1.

p-Coumaroyl-CoA:monolignol transferases (PMT, also called monolignol coumarate transferases) constitute another type of BAHD acyltransferases. These acyltransferases catalyze the acylation of monolignols (e.g., p-coumaryl alcohol, coniferyl alcohol and/or sinapyl alcohol) with p-coumarate, for example, as illustrated below.

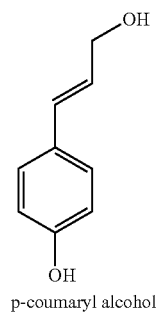  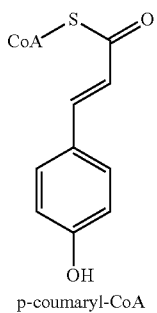

p-coumaryl alcohol        p-coumaryl-CoA

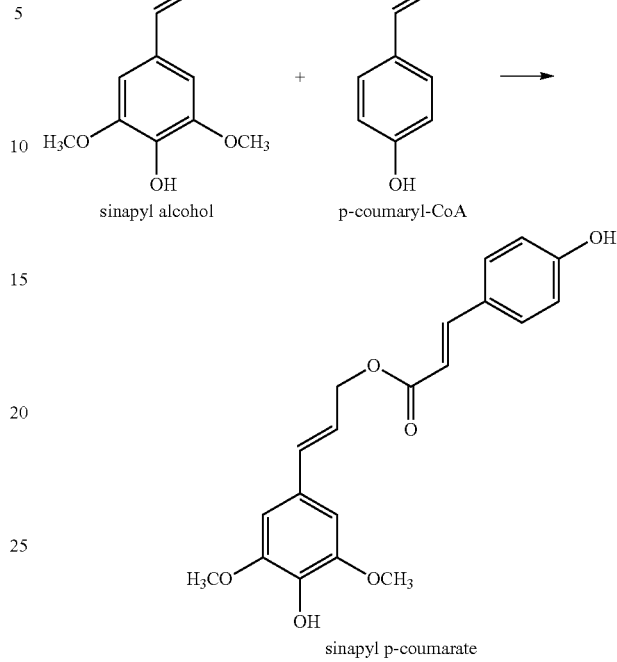

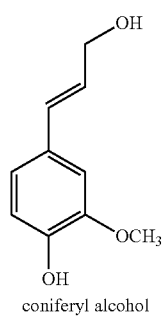  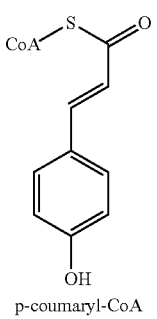

coniferyl alcohol        p-coumaryl-CoA

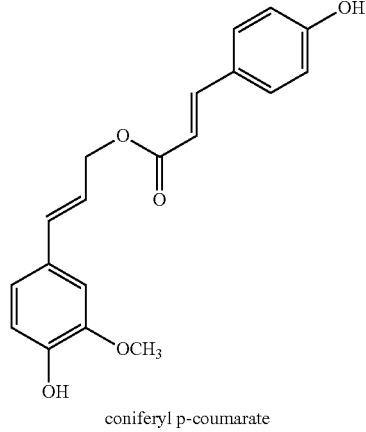

coniferyl p-coumarate

Nucleic acids encoding p-coumaroyl-CoA:monolignol transferases of the invention include nucleic acids encoding a *Panicum virgatum* (switchgrass) p-coumaroyl-CoA:monolignol transferase (PvPMT). An exemplary nucleic acid encoding PvPMT has the following nucleic acid sequence (SEQ ID NO:1).

```
ATGGGTACCATCGGGTTCCCGGTGACGAGGACGAGCAGGTCGCTGGTGGC
GCCGTCGTCGGCGACGCCGCAGGAGACGCTGCACCTGTCGGTGATCGACC
GCGTGGCGGGGCTGCGGCACCTGGTGCGGTCGCTGCACGTGTTCGACGGC
CGCCGCGGCGAGGCGGCGGTGAGGACGCCGGCGGAGACGCTGCGGGCGGC
GCTGGGGAAGGCGCTGGTGGACTATTACCCGCTGGCGGGGCGGTTCGTGG
AGGAGGACGGGGAGGTGCGGGTGGCGTGCACGGCGGGGGGCGCCTGGTTC
GTGGAGGCGGCGGCGGCGTGCACCCTGGAGGAGGTGAAGCACCTGGACCA
CCCCATGGTCATCCCCAAGGAGGACCTGCTGCCGGAGCCGGCGCCGGACG
TCAACCCCCTCGACATGCCGCTCATGATGCAGGTGACGGAGTTCGCGTGC
GGCGGCTTCGTGGTGGGCCTCATCTCCGTGCACACCATCGCCGACGGCCT
GGGCGCCGGGCAGTTCATCAACGCGGTGGCGGACTACGCGCGTGGCCTCC
CGAGGCCCCGCGTGCTCCCCGTCTGGGCGCGCGACGTCATCCCGGCGCCG
TCCAGGATCGTGTCCCCGCCGCCGCGGTTCGACCTCCTGGACCTCCGCTA
CTTCACCGTGGACCTCAGCCCGGAGCACATCGCCAAGGTCAAGTCCAGCT
TCTTCGAGGCGACGGGGCAGCGCTGCTCGGCGTTCGACGTGTGCGTCGCC
AAGACCTGGCAGTCCCGCGTCCGCGCGCTCCGGCTGGACGGCGACGACCC
GGCGCGGCCCATCCACGTGTGCTTCTTCGCCAACACGCGGCACCTCCTGC
```

```
CGCAGCTGGCGCCCGGGTTCTACGGCAACTGCTTCTACACCGTGAGGGCG
ACGCGGCCCTGCGGCGAGGTGGCGGCGGCCGGCGTGGTGGAGGTGGTGCG
CGCCATCCGGGACGCCAAGGCGCGGCTGGGCGCGGACTTCGCGCGGTGGG
CGGCGGGCGGGTTCGAGCGCGACCCCTACGAGCTCACCTTCAGCTACGAC
TCGCTCTTCGTCTCCGACTGGACGCGGCTGGGGTTCCTGGAGGCGGACTA
CGGGTGGGGCGCGCCGGCGCACGTCGTGCCCTTCTCCTACCACCCCTTCA
TGGCCGTCGCCGTCATCGGCGCGCCGCCGGCGCCCAAGCCCGGCGCGCGC
GTCATGACCATGTGCGTCACGGAGAAGCACCTGCCCGAGTTCCAGGAGCA
GATGAACGCCTTCGCCGCCGGGAACCACCAGTGA
```

SEQ ID NO:1 encodes the following PvPMT amino acid sequence (SEQ ID NO:2).

```
MGTIGFPVTRTSRSLVAPSSATPQETLHLSVIDRVAGLRHLVRSLHVFDG
RRGEAAVRTPAETLRAALGKALVDYYPLAGRFVEEDGEVRVACTAGGAWF
VEAAAACTLEEVKHLDHPMVIPKEDLLPEPAPDVNPLDMPLMMQVTEFAC
GGFVVGLISVHTIADGLGAGQFINAVADYARGLPRPRVLPVWARDVIPAP
SRIVSPPPRFDLLDLRYFTVDLSPEHIAKVKSSFFEATGQRCSAFDVCVA
KTWQSRVRALRLDGDDPARPIHVCFFANTRHLLPQLAPGFYGNCFYTVRA
TRPCGEVAAAGVVEVVRAIRDAKARLGADFARWAAGGFERDPYELTFSYD
SLFVSDWTRLGFLEADYGWGAPAHVVPFSYHPFMAVAVIGAPPAPKPGAR
VMTMCVTEKHLPEFQEQMNAFAAGNHQ*
```

Other nucleic acids encoding p-coumaroyl-CoA:monolignol transferases of the invention include nucleic acids encoding a *Sorghum bicolor* (Sorghum) p-coumaroyl-CoA:monolignol transferase (SbPMT). An exemplary nucleic acid encoding SbPMT has the following nucleic acid sequence (SEQ ID NO:3).

```
ATGGGCACAATCGATGATACCGCCGGGTTATTCCCGGTGACGAGGACGAA
CAGGTCGCTGGTGCCGCCGTCGTCGGCGACGCCGCAGGAGACGCTGCGCC
TGTCGGTGATCGACCGCGTGGCGGGGCTGCGCCACCTGGTGCGGTCGCTG
CACGTGTTCGCCGGCGGCGAGAACAAGAAGCAGGCGGCGCCGCCGGCGAA
GTCCCTGCGGGAGGCGCTGGGAAAGGCGCTGGTGGACTACTACCCGTTCG
CGGGGCGGTTCGTGGAGGAAGACGGGGAGGTCCGGGTGGCGTGCACCGGC
GAGGGCGCCTGGTTCGTGGAGGCCGCCGCCGCGTGCTCCCTGGAGGAGGT
CCGGCACCTGGACCACCCCATGCTCATCCCCAAGGAGGAGCTGCTGCCGG
AGCCGGCGCCCGGCGTCAACCCGCTCGACATGCCGCTCATGATGCAGGTG
ACGGAGTTCACGTGCGGCGGCTTCGTGGTGGGTCTAATCTCCGTCCACAC
CATCGCCGACGGTCTAGGCGCCGGGCAGTTCATCAACGCGGTGGCGGACT
ACGCCCGTGGCGGCGCCACCGCCGGCGCCGTCACCAGACCCCGCATCACC
CCGATCTGGGCGCGCGACGTGATCCCGGACCCGCCCAAGATGCCGGCGCC
GCCGCCGCGCCTCGACCTGCTGGACCTGGTCTACTTCACGACGGACCTGA
GCCCGGACCACATCGCCAAGGTCAAGTCCAGCTACCTCGAGTCCACGGGG
CAGCGCTGCTCGGCGTTCGACGTGTGCGTGGCGCGCACCTGGCAGGCCCG
CGTCCGCGCGCTCCGCCTCCCGGACGCCGCCGCGCCCGTCCACGTCTGCT
TCTTCGCCAACACCCGCCACCTGCTCCCGGCGACGGCGGCGGCGCCGGCG
AGTGGGTTCTACGGCAACTGCTTCTACACCGTCAAGGCGACGCGGCCCAG
CGGCGAGGTGGCGGCGGCCGACATCGTCGACGTCGTGCGCGCCATCCGGG
ACGCCAAGGCGAGGCTCGCCGCCGACTTCGCGAGGTGGGCGGCGGGCGGG
TTTGATCGGGACCCCTACGAGCTCACCTTCACCTACGACTCCCTCTTCGT
CTCCGACTGGACGAGGCTAGGGTTCCTCGAGGCTGACTATGGCTGGGGCA
CGCCGACGCACGTCGTGCCGTTCTCGTACCACCCGTTCATGGCCGTCGCC
GTCATCGGGCGCCGCCGGCGCCTAAGCCCGGCGCACGCATCATGACCAT
GTGCGTCCAGGAGCAGCACCTGCCTGAGTTCCAGGAGCAGATGAACCAGC
CCTGCTCATGA
```

SEQ ID NO:3 encodes the following SbPMT amino acid sequence (SEQ ID NO:4).

```
MGTIDDTAGLFPVTRTNRSLVPPSSATPQETLRLSVIDRVAGLRHLVRSL
HVFAGGENKKQAAPPAKSLREALGKALVDYYPFAGRFVEEDGEVRVACTG
EGAWFVEAAAACSLEEVRHLDHPMLIPKEELLPEPAPGVNPLDMPLMMQV
TEFTCGGFVVGLISVHTIADGLGAGQFINAVADYARGGATAGAVTRPRIT
PIWARDVIPDPPKMPAPPPRLDLLDLVYFTTDLSPDHIAKVKSSYLESTG
QRCSAFDVCVARTWQARVRALRLPDAAAPVHVCFFANTRHLLPATAAAPA
SGFYGNCFYTVKATRPSGEVAAADIVDVVRAIRDAKARLAADFARWAAGG
FDRDPYELTFTYDSLFVSDWTRLGFLEADYGWGTPTHVVPFSYHPFMAVA
VIGAPPAPKPGARIMTMCVQEQHLPEFQEQMNQPCS*
```

The terms "p-coumaroyl-CoA:monolignol transferase(s)" and "monolignol coumarate transferase(s)" are used interchangeably herein.

Nucleic acids encoding the aforementioned BAHD acyltransferases allow identification and isolation of related nucleic acids and their encoded enzymes that provide a means for production of altered lignins in plants.

For example, related nucleic acids can be isolated and identified by mutation of the SEQ ID NO:1 or SEQ ID NO:3 sequence and/or by hybridization to DNA and/or RNA isolated from other plant species using SEQ ID NO:1 or SEQ ID NO:3 nucleic acids as probes. The sequence of the p-coumaroyl-CoA:monolignol transferase enzyme (e.g., SEQ ID NO:2 or SEQ ID NO:4) can also be examined and used a basis for designing alternative p-coumaroyl-CoA:monolignol transferase nucleic acids that encode related p-coumaroyl-CoA:monolignol transferase polypeptides.

In one embodiment, the BAHD acyltransferase nucleic acids of the invention include any nucleic acid that can selectively hybridize to SEQ ID NO:1 or SEQ ID NO:3.

The term "selectively hybridize" includes hybridization, under stringent hybridization conditions, of a nucleic acid sequence to a specified nucleic acid target sequence (e.g., SEQ ID NO:1 or SEQ ID NO:3) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has at least about 70% or at least about 80% sequence identity or complementarity with SEQ ID NO:1 or SEQ ID NO:3.

Thus, the nucleic acids of the invention include those with about 500 of the same nucleotides as SEQ ID NO:1 or SEQ ID NO:3, or about 600 of the same nucleotides as SEQ ID NO:1 or SEQ ID NO:3, or about 700 of the same nucleotides as SEQ ID NO:1 or SEQ ID NO:3, or about 800 of the same nucleotides as SEQ ID NO:1 or SEQ ID NO:3, or about 900 of the same nucleotides as SEQ ID NO:1 or SEQ ID NO:3, or about 1000 of the same nucleotides as SEQ ID NO:1 or SEQ ID NO:3, or about 1100 of the same nucleotides as SEQ ID NO:1 or SEQ ID NO:3, or about 1200 of the same nucleotides as SEQ ID NO:1 or SEQ ID NO:3, or about 1300 of the same nucleotides as SEQ ID NO:1 or SEQ ID NO:3, or about 500-1325 of the same nucleotides as SEQ ID NO:1 or SEQ ID NO:3. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5° C. + 16.6(\log M) + 0.41(\% \; GC) - 0.61(\% \; \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to SEQ ID NO:1 or SEQ ID NO:3.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 mL of water), 0.1 mg/mL boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., SEQ ID NO:1 or SEQ ID NO:3) or an amino acid sequence (e.g., SEQ ID NO:2 or SEQ ID NO:4). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 10 amino acids, and can optionally be 15, 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995). An updated version of the BLAST family of programs includes the BLAST+ suite. (Camacho, C., Coulouris, G., Avagyan, V., Ma, N, Papadopoulos J, Bealer K, Madden T L. BLAST+: architecture and applications. *BMC Bioinformatics*. 2009 Dec. 15; 10:421).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Sequence identity/similarity values provided herein can refer to the value obtained using the BLAST+2.5.0 suite of programs using default settings (blast.ncbi.nlm.nih.gov) (Camacho, C., Coulouris, G., Avagyan, V., Ma, N, Papadopoulos J, Bealer K, Madden T L. BLAST+: architecture and applications. *BMC Bioinformatics*. 2009 Dec. 15; 10:421).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, or at least 60%, or at least 70%, or at least 80%, or at least 90% or at least 95% sequence identity or any percentage of value within the range of 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have p-coumaroyl-CoA:monolignol transferase activity, meaning that both polypeptides can synthesize monolignol coumarates from a monolignol and coumaroyl-CoA. The polypeptide that is substantially identical to a p-coumaroyl-CoA:monolignol transferase with a SEQ ID NO:2 or SEQ ID NO:4 sequence may not have exactly the same level of activity as the p-coumaroyl-CoA:monolignol transferase with a SEQ ID NO:2 or SEQ ID NO:4. Instead, the substantially identical polypeptide may exhibit greater or lesser levels of p-coumaroyl-CoA:monolignol transferase activity than the p-coumaroyl-CoA:monolignol transferase with SEQ ID NO:2 or SEQ ID NO:4, as measured by assays available in the art or described herein. For example, the substantially identical polypeptide can have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the p-coumaroyl-CoA:monolignol transferase with the SEQ ID NO:2 or SEQ ID NO:4 sequence when measured by similar assay procedures.

Alternatively, substantial identity is present when second polypeptide is immunologically reactive with antibodies raised against the first polypeptide (e.g., a polypeptide with SEQ ID NO:2 or SEQ ID NO:4). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The p-coumaroyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of the SEQ ID NO:2 or SEQ ID NO:4 sequence. Alternatively, the p-coumaroyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:2 or SEQ ID NO:4 sequence.

Lignin

Lignin broadly refers to a biopolymer that is typically part of secondary cell walls in plants. Lignin is a complex moderately cross-linked aromatic polymer (see, e.g., FIG. 1). Lignin may also be covalently linked to hemicelluloses. Hemicellulose broadly refers to a class of branched sugar polymers composed of pentoses and hexoses. Hemicelluloses typically have an amorphous structure with up to hundreds or thousands of pentose units and they are generally at least partially soluble in dilute alkali. Cellulose broadly refers to an organic compound with the formula $(C_6H_{10}O_5)_z$ where z is an integer. Cellulose is a linear polysaccharide that can include linear chains of beta-1-4-linked glucose residues of several hundred to over ten thousand units.

Lignocellulosic biomass represents an abundant, inexpensive, and locally available feedstock for conversion to carbonaceous fuel (e.g., ethanol, biodiesel, biofuel and the like). However, the complex structure of lignin, which includes ether and carbon-carbon bonds that bind together the various subunits of lignin, and the crosslinking of lignin to other plant cell wall polymers, make it the most recalcitrant of plant polymers. Thus, significant quantities of lignin in a biomass can inhibit the efficient usage of plants as a source of fuels and other commercial products. Gaining access to the carbohydrate and polysaccharide polymers of plant cells for use as carbon and energy sources therefore requires significant energy input and often harsh chemical treatments, especially when significant amounts of lignin are present. For example, papermaking procedures in which lignin is removed from plant fibers by delignification reactions are typically expensive, can be polluting and generally require use of high temperatures and harsh chemicals largely because the structure of lignin is impervious to mild conditions. Plants with altered lignin structures that could be more readily cleaved under milder conditions would reduce the costs of papermaking and make the production of biofuels more competitive with currently existing procedures for producing oil and gas fuels.

Plants make lignin from a variety of subunits or monomers that are generally termed monolignols. Such primary monolignols include p-coumaryl alcohol, coniferyl alcohol, and sinapyl alcohol.

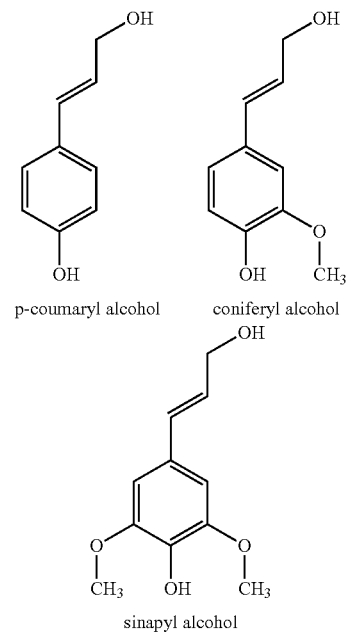

Monolignols destined for lignin polymerization in normal plants can be preacylated with acetate, p-hydroxybenzoate, or p-coumarate (Ralph et al., *Phytochem. Rev.* 3:29-60 (2004)). p-Coumarates can acylate the γ-position of phenylpropanoid side chains mainly found in the syringyl units of lignin. Studies indicate that monolignols, primarily sinapyl alcohol, are enzymatically preacylated with p-coumarate prior to their incorporation into lignin, indicating that the monolignol p-coumarate conjugates, coniferyl p-coumarate and sinapyl p-coumarate, can also be 'monomer' precursors of lignin.

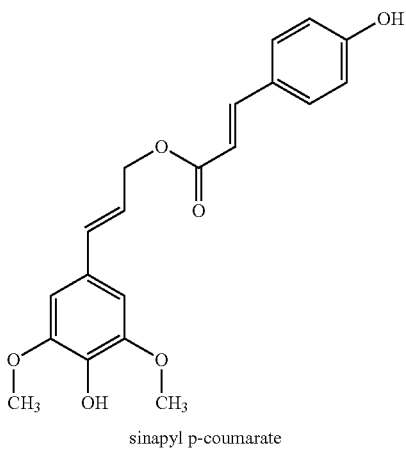 [SMILES: COc1cc(/C=C/COC(=O)/C=C/c2ccc(O)cc2)cc(OC)c1O]

sinapyl p-coumarate

Although monolignol p-coumarate-derived units may comprise up to 40% of the lignin in some grass tissues, the p-coumarate moiety from such conjugates does not enter into the radical coupling (polymerization) reactions occurring during lignification. Instead, the p-coumarate moieties substantially remain as terminal units with an unsaturated side chain and a free phenolic group (Ralph et al., *J. Am. Chem. Soc.* 116: 9448-9456 (1994); Hatfield et al., *J. Sci. Food Agric.* 79: 891-899 (1999)). Thus, the presence of sinapyl p-coumarate conjugates produces a lignin 'core' with terminal p-coumarate groups and no new bonds in the backbone of the lignin polymer.

Regardless, lignocellulosic biomass with lignin comprising a higher proportion of p-coumarate content is more amenable to pretreatment and saccharification (hydrolysis). Pretreatment of biomass removes a large proportion of the lignin and other materials from the cellulose and hemicellulose and enhances the porosity of the biomass for optional downstream hydrolysis. A variety of biomass pretreatments are well known in the art. Exemplary pretreatments include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, extractive ammonia (EA) pretreatment, and pulsed electrical field treatment, among others. See, e.g., Kumar et al. 2009 (Kumar, P.; Barrett, D. M.; Delwiche, M. J.; Stroeve, P., Methods for Pretreatment of Lignocellulosic Biomass for Efficient Hydrolysis and Biofuel Production. *Industrial & Engineering Chemistry Research* 2009, 48, (8), 3713-3729) and da Costa Sousa et al. 2016 (da Costa Sousa, L.; Leonardo, Jin, M.; Chundawat, S. P. S.; Bokade, V.; Tang, X.; Azarpira, A.; Lu, F.; Avci, F.; Humpula, J.; Uppugundla, N.; Gunawan, C.; Pattathil, S.; Cheh, A. M.; Kothari, N.; Kumar, N.; Ralph, J.; Hahn, M. G.; Wyman, C. E.; Singh, S.; Simmons, B. A.; Dale, B. E.; Balan, V. Next-Generation Ammonia Pretreatment Enhances Cellulosic Biofuel Production. Energy Environ. Sci., 2016, 9, 1215-1223). Hydrolysis converts biomass polymers to fermentable sugars, such as glucose and xylose, and other monomeric or oligomeric components. Methods for hydrolyzing biomass, also known as saccharification, are well known in the art. Exemplary hydrolysis methods include enzymatic hydrolysis (e.g., with cellulases or other enzymes) and acid hydrolysis (e.g., with sulfurous, sulfuric, hydrochloric, hydrofluoric, phosphoric, nitric, and/or formic acids), among other methods. Thus, plants and biomass with lignin comprising a higher proportion of p-coumarate content are more suitable to processing for downstream applications.

Figure 11:
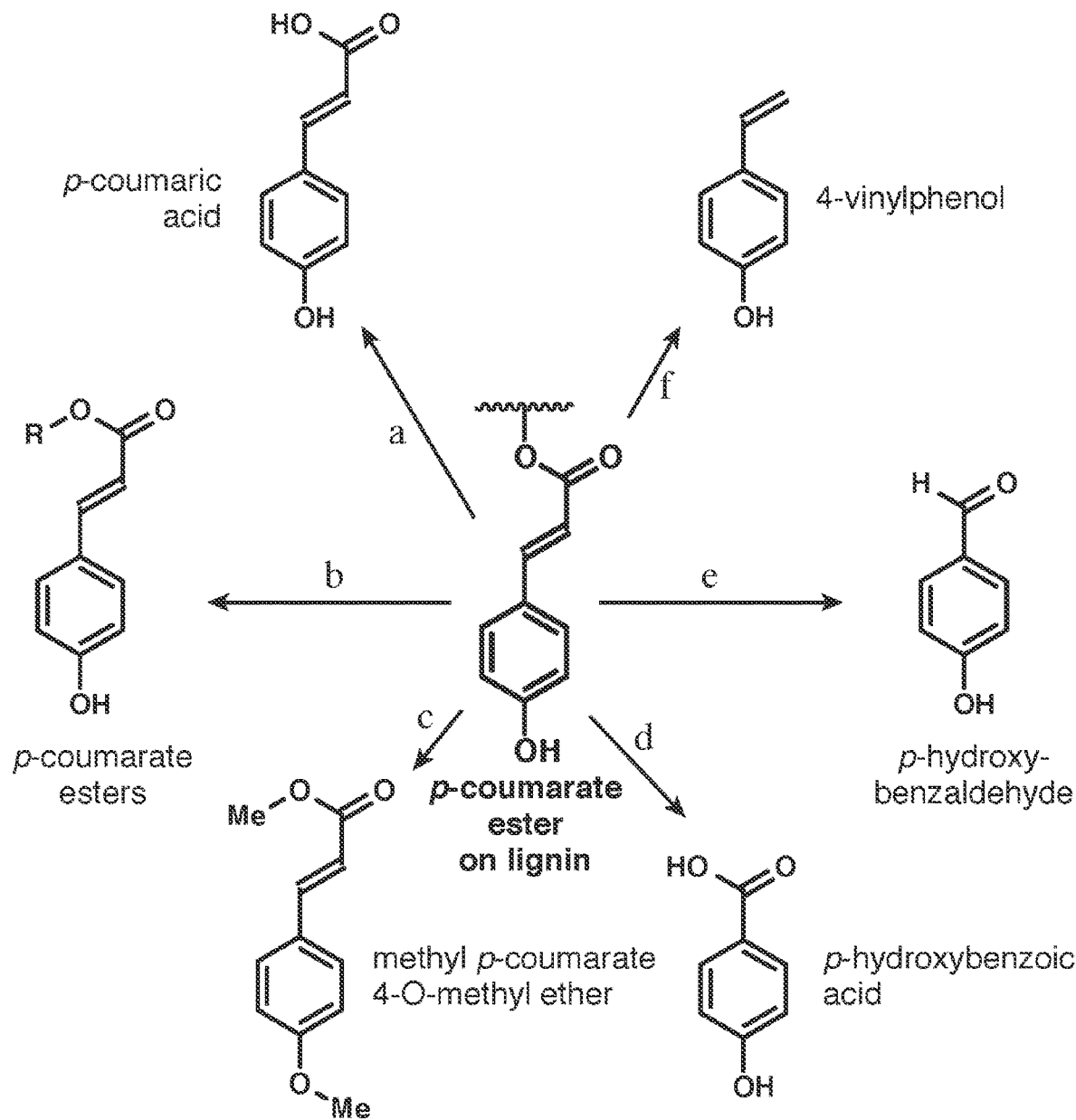
FIG. 11 is a schema showing a variety of compounds that can be made from p-coumarate.

Lignin comprising a higher proportion of p-coumarate content also has a higher proportion of pendant p-coumarate units, which can be cleaved from the lignin using conditions typically employed for cleaving ester bonds, described in further detail below. The cleaved p-coumarate units can be recovered for downstream uses.

p-Coumarate (or p-coumaric acid), currently valued at ~$20/kg, has some significant applications, but, because has not been previously available in bulk quantities, its applications have been limited. This could readily change with the p-coumarate-enriched lignin provided with the present invention. p-Coumarate has a number of medical/cosmetic uses. See, e.g., U.S. Pub. No. 2007/0183996 A1, U.S. Pub. No. 2007/0183996 A1, U.S. Pat. Nos. 8,481,593, 9,089,499, U.S. Pub. No. 2007/0183996, U.S. Pub. No. 2011/0237551, and U.S. Pub. No. 2013/0272983). p-Coumarate also has a large number of applications in health, food, pharmaceutical, and cosmetic industries due to its physiological functions in antioxidant, anti-mutagenesis, anti-genotoxicity, antimicrobial, anti-inflammatory, anti-melanogenesis, and anti-thrombosis activities. See Ferguson et al. 2003 (Ferguson, L. R., Lim, I. F., Pearson, A. E., Ralph, J., and Harris, P. J. Bacterial antimutagenesis by hydroxycinnamic acids from plant cell walls. (2003) *Mutation Research-Genetic Toxicology and Environmental Mutagenesis* 542(1-2), 49-58), Ferguson et al. 2005 (Ferguson, L. R., Zhu, S. T., and Harris, P. J. Antioxidant and antigenotoxic effects of plant cell wall hydroxycinnamic acids in cultured HT-29 cells. (2005) *Molecular Nutrition & Food Research* 49(6), 585-593), Bodini et al. (Bodini, S. F., Manfredini, S., Epp, M., Valentini, S., and Santori, F. Quorum sensing inhibition activity of garlic extract and p-coumaric acid. (2009) *Lett Appl Microbiol* 49(5), 551-555), An et al. 2008 (An, S. M., Lee, S. I., Choi, S. W., Moon, S. W., and Boo, Y. C. p-Coumaric acid, a constituent of Sasa quelpaertensis Nakai, inhibits cellular melanogenesis stimulated by alpha-melanocyte stimulating hormone. (2008) *Brit J Dermatol* 159(2), 292-299), and Razzaghi-Asl et al. 2013 (Razzaghi-Asl, N., Garrido, J., Khazraei, H., Borges, F., and Firuzi, O. Antioxidant properties of hydroxycinnamic acids: A review of structure-activity relationships. (2013) *Current Medicinal Chemistry* 20(36), 4436-4450). p-Coumarate is also used as a precursor for natural aromatic organic compounds, including p-hydroxybenzoic acid and 4-vinylphenol, or a variety of commodity chemicals, including caffeate (Nambudiri A M, Bhat J V. Conversion of p-coumarate into caffeate by *Streptomyces nigrifaciens*. Purification and properties of the hydroxylating enzyme. *Biochem J.* 1972 November; 130(2): 425-33), volatile phenols (Cabrita M J P V, Patao R, Freitas A M C. Conversion of hydroxycinnamic acids into volatile phenols in a synthetic medium and red wine by Dekkera bruxellensis. *Ciencia e Tecnologia de Alimentos, Campinas.* 2012; 32(1):106-11), and others. FIG. 11 shows a variety of derivatives that are readily produced from p-coumarate.

p-Coumarate is also a versatile and attractive building block for the generation of novel, sustainable polymeric materials. The phenolic functional groups allow these building blocks to be used as monomers in step- and chain-polymerization reactions (Upton, B. M., and Kasko, A. M. Strategies for the conversion of lignin to high-value polymeric materials: Review and perspective. (2016) *Chemical Reviews* 116(4), 2275-2306). Derivatives have been used for the synthesis of polyesters, where they replace petroleumbased diols (Kaneko, T., Matsusaki, M., Hang, T. T., and Akashi, M. Thermotropic liquid-crystalline polymer derived from natural cinnamoyl biomonomers. (2004) *Macromol Rapid Comm* 25(5), 673-677) (Nagata, M., and Hizakae, S. Synthesis and characterization of photocrosslinkable biodegradable polymers derived from 4-hydroxycinnamic acid. (2003) *Macromol Biosci* 3(8), 412-419). Thermal polymerization of p-coumaric acid, for example, affords a liquid-crystalline polymer that adopts a nematic liquid-crystalline structure at temperatures between 215-280° C. (Kaneko, T., Matsusaki, M., Hang, T. T., and Akashi, M. Thermotropic liquid-crystalline polymer derived from natural cinnamoyl biomonomers. (2004) *Macromol Rapid Comm* 25(5), 673-677). Methacrylation of certain lignin-derived monomers has provided access to monomers that can be polymerized using conventional free-radical polymerization methods as well as via various controlled radical polymerization techniques, including atom transfer radical polymerization (ATRP) and reversible addition fragmentation chain transfer (RAFT) polymerization (Holmberg, A. L., Reno, K. H., Nguyen, N. A., Wool, R. P., and Epps, T. H., 3rd. Syringyl methacrylate, a hardwood lignin-based monomer for high-Tg polymeric materials. (2016) *ACS Macro Letters* 5(5), 574-578).

In contrast to p-coumarate, ferulate esters do undergo radical coupling reactions under lignification conditions. Model ferulates, such as the ferulate shown below (where R is $CH_3$—, $CH_3$—$CH_2$—, a sugar, a polysaccharide, pectin, cell-wall (arabino)xylan or other plant component), readily undergo radical coupling reactions with each other and with lignin monomers and oligomers to form cross-linked networks.

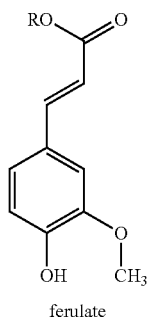
ferulate

If present during lignification, ferulates can become inextricably bound into the lignin by ether and C—C bonds. Although such ferulate moieties are no more extractable or cleavable from the lignin structure than other lignin units under most conditions, the ester itself can be readily cleaved using conditions generally employed for ester cleavage. Upon cleavage of such ester bonds, other plant cell wall components can be released. For example, an arabinoxylan (hemicellulose) chain can be released from a ferulate-mediated lignin attachment by cleaving the ester.

Ferulate-monolignol ester conjugates, such as coniferyl ferulate or sinapyl ferulate, are made by plants as secondary metabolites during, among other things, lignin biosynthesis. [Paula et al, *Tetrahedron* 51: 12453-12462 (1994); Seca et al., *Phytochemistry* 56: 759-767 (2001); Hsiao & Chiang, *Phytochemistry* 39: 899-902 (1995); Li et al., *Planta Med.* 72: 278-280 (2005)]. The structures of coniferyl ferulate and sinapyl ferulate are shown below.

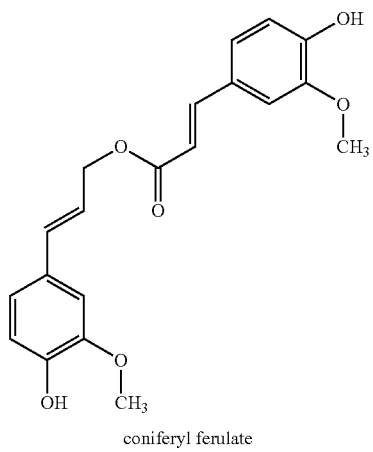
coniferyl ferulate

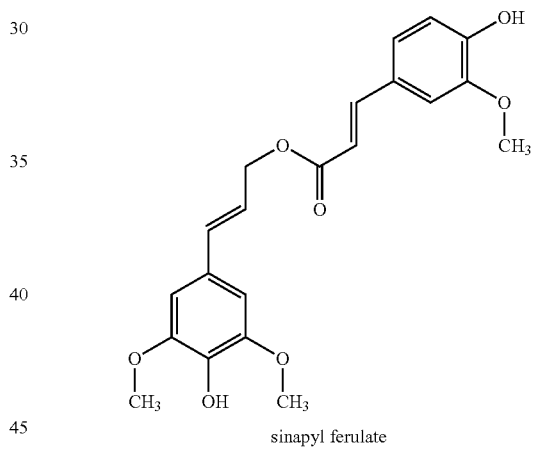
sinapyl ferulate

Feruloyl-CoA:monolignol transferases biosynthesize coniferyl ferulate from coniferyl alcohol and feruloyl-CoA as shown below.

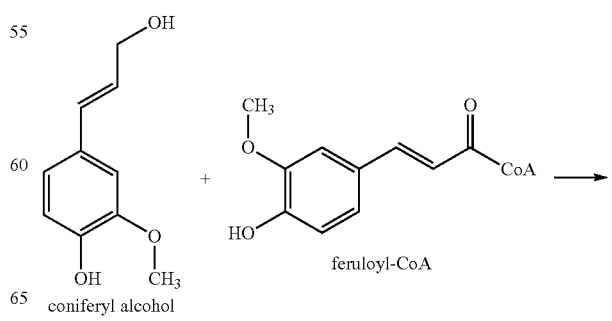
coniferyl alcohol + feruloyl-CoA →

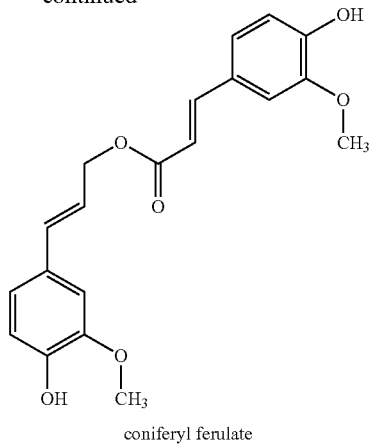

coniferyl ferulate

The incorporation of monolignol ferulates into the lignin of plants allows the cell wall materials and lignin to be readily cleaved or processed into useful products. See also, U.S. Pat. Nos. 9,441,235, 9,487,794, and 9,493,783, the contents of all of which are specifically incorporated herein by reference in their entireties.

Monolignol ferulates made by feruloyl-CoA:monolignol transferases can be incorporated by radical coupling into plant lignins. Both the monolignol and the ferulate moieties can undergo such coupling, resulting in a lignin that can be complex. However, such 'double-ended-incorporation' still yields readily cleavable ester linkages that have been engineered into the backbone of the lignin polymer network. Esters are readily cleaved under much less stringent conditions by the same chemical processes used to cleave lignin, but the lignin resulting from the methods described herein is significantly easier to cleave, and provides more facile and less costly access to the plant cell wall polysaccharides. See also, U.S. Pat. Nos. 9,441,235, 9,487,794, and 9,493,783, the contents of all of which are specifically incorporated herein by reference in their entireties.

Lignins can be degraded by chemical or enzymatic means to yield a variety of smaller monomers and oligomers. While enzymatic processes are generally preferred because they do not require high temperatures and harsh chemicals, such enzymatic processes have previously not been as effective at solubilizing lignin moieties away from valuable plant cell constituents (e.g., polysaccharides and carbohydrates).

Plants with the feruloyl-CoA:monolignol transferase nucleic acids and/or enzymes supply monolignol ferulates for facile lignification in plants, thereby yielding plants with lignins that are more readily cleaved or processed to release cellulose, hemicelluloses and lignin breakdown products.

Conditions for releasing the cellulose, hemicelluloses and lignin breakdown products from plants containing the feruloyl-CoA:monolignol transferase nucleic acids and/or enzymes include conditions typically employed for cleaving ester bonds. Thus, the ester bonds within monolignol ferulate-rich lignins can be cleaved by milder alkaline and/or acidic conditions than the conditions typically used to break down the lignin of plants that are not rich in monolignol ferulates. For example, mildly alkaline conditions involving use of ammonia may be used to cleave the ester bonds within monolignol ferulate-rich lignins, whereas such conditions would not cleave substantially any of the ether and carbon-carbon bonds in normal lignins. See also, U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

For acid digestion, exemplary methods include but are not limited to acid γ-valerolactone acid digestion (Luterbacher, J. S., Azarpira, A., Motagamwala, A. H., Lu, F., Ralph, J., and Dumesic, J. A. Aromatic monomer production integrated into the γ-valerolactone sugar platform. (2015) *Energy and Environmental Science* 8(9), 2657-2663), digestion as described in Santoro et al. (Santoro, N., Cantu, S. L., Tornqvist, C. E., Falbel, T. G., Bolivar, J. L., Patterson, S. E., Pauly, M., and Walton, J. D. A high-throughput platform for screening milligram quantities of plant biomass for lignocellulose digestibility. (2010) *Bioenergy Research* 3(1), 93-102), and ionic digestion (Kim, K. H., Dutta, T., Ralph, J., Mansfield, S. D., Simmons, B. A., and Singh, S. Impact of lignin polymer backbone esters on ionic liquid pretreatment of poplar. (2017) *Biotechnology for Biofuels*).

Plants Modified to Contain a p-Coumaroyl-CoA:Monolignol Transferase

In order to engineer plants with lignins that contain significant levels of monolignol coumarates, one of skill in the art can introduce p-coumaroyl-CoA:monolignol transferases or nucleic acids encoding such p-coumaroyl-CoA:monolignol transferases into the plants. For example, one of skill in the art can inject p-coumaroyl-CoA:monolignol transferase enzymes into young plants.

Alternatively, one of skill in the art can generate genetically-modified plants that contain nucleic acids encoding p-coumaroyl-CoA:monolignol transferases within their somatic and/or germ cells. Such genetic modification can be accomplished by procedures available in the art. For example, one of skill in the art can prepare an expression cassette or expression vector that can express one or more encoded p-coumaroyl-CoA:monolignol transferase enzymes. Plant cells can be transformed by the expression cassette or expression vector, and whole plants (and their seeds) can be generated from the plant cells that were successfully transformed with the p-coumaroyl-CoA:monolignol transferase nucleic acids. Some procedures for making such genetically modified plants and their seeds are described below.

Promoters: The p-coumaroyl-CoA:monolignol transferase nucleic acids of the invention can be operably linked to a promoter, which provides for expression of mRNA from the p-coumaroyl-CoA:monolignol transferase nucleic acids. The promoter is typically a promoter functional in plants and/or seeds, and can be a promoter functional during plant growth and development. A p-coumaroyl-CoA:monolignol transferase nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the P$_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Suitable promoters for use in the present invention include native or heterologous promoters.

Expression cassettes generally include, but are not limited to, a plant promoter such as the CaMV 35S promoter (Odell et al., Nature. 313:810-812 (1985)), or others such as CaMV 19S (Lawton et al., Plant Molecular Biology. 9:315-324 (1987)), nos (Ebert et al., Proc. Natl. Acad. Sci. USA. 84:5745-5749 (1987)), Adh1 (Walker et al., Proc. Natl. Acad. Sci. USA. 84:6624-6628 (1987)), sucrose synthase (Yang et al., Proc. Natl. Acad. Sci. USA. 87:4144-4148 (1990)), α-tubulin, ubiquitin, actin (Wang et al., Mol. Cell. Biol. 12:3399 (1992)), cab (Sullivan et al., Mol. Gen. Genet. 215:431 (1989)), PEPCase (Hudspeth et al., Plant Molecular Biology. 12:579-589 (1989)) or those associated with the R gene complex (Chandler et al., The Plant Cell. 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., EMBO J. 3:1671 (1971)) and the actin promoter from rice (McElroy et al., The Plant Cell. 2:163-171 (1990)). Seed specific promoters, such as the phaseolin promoter from beans, may also be used (Sengupta-Gopalan, Proc. Natl. Acad. Sci. USA. 83:3320-3324 (1985). Further suitable promoters include any of the promoters on the various genes of the conventional lignin monomer (monolignol) biosynthetic pathway. See, e.g., Vanholme et al. 2012 (Vanholme, R., Morreel, K., Darrah, C., Oyarce, P., Grabber, J. H., Ralph, J., and Boerjan, W. Metabolic engineering of novel lignin in biomass crops. (2012) New Phytol. 196(4), 978-1000); Vanholme et al. 2010 (Vanholme, R., Demedts, B., Morreel, K., Ralph, J., and Boerjan, W. Lignin biosynthesis and structure. (2010) Plant Physiol. 153(3), 895-905), Vanholme et al. 2008 (Vanholme, R., Morreel, K., Ralph, J., and Boerjan, W. Lignin engineering. (2008) Curr. Opin. Plant Biol. 11(3), 278-285), Boerjan et al. 2003 (Boerjan, W., Ralph, J., and Baucher, M. Lignin biosynthesis. (2003) Annual Reviews in Plant Biology 54, 519-546). An exemplary promoter from this pathway is the cinnamate-4-hydroxylase (C4H) promoter (Bell-Lelong, D. A., Cusumano, J. C., Meyer, K., and Chapple, C. Cinnamate-4-hydroxylase expression in Arabidopsis: regulation in response to development and the environment. (1997) Plant Physiol. 113, 729-738), the sequence of which is SEQ ID NO:5:

aagcttagaggagaaactgagaaaatcagcgtaatgagagacgagagcaa tgtgctaagagaagagattgggaagagagaagagacgataaaggaaacgg aaaagcatatggaggagcttcatatggagcaagtgaggctgagaagacgg tcgagtgagcttacggaagaagtggaaaggacgagagtgtctgcatcgga aatggctgagcagaaaagagaagctataagacagctttgtatgtctcttg accattacagagatgggtacgacaggctttggagagttgttgccggccat aagagtaagagagtagtggttttaacaacttgaagtgtaagaacaatgag tcaatgactacgtgcaggacattggacataccgtgtgttcttttggattg aaatgttgtttcgaagggctgttagttgatgttgaaaataggttgaagtt gaataatgcatgttgatatagtaaatatcaatggtaatattttctcattt cccaaaactcaaatgatatcatttaattataaactaacgtaaactgttga caatacacttatggttaaaaatttggagtcttgttttagtatacgtatca ccaccgcacggtttcaaaaccacataattgtaaatgttattggaaaaaag aacccgcaatacgtattgtattttggtaaacatagctctaagcctctaat atataagctctcaacaattctggctaatggtcccaagtaagaaaagccca tgtattgtaaggtcatgatctcaaaaacgagggtgaggtggaatactaac atgaggagaaagtaaggtgacaaattttttggggcaatagtggtggatatg gtggggaggtaggtagcatcatttctccaagtcgctgtctttcgtggtaa tggtaggtgtgtctctctttatattatttattactactcattgttaattt cttttttctacaatttgtttcttactccaaaatacgtcacaaatataat actaggcaaataattatttaattgtaagtcaatagagtggttgttgtaaa attgattttgatattgaaagagttcatggacggatgtgtatgcgccaaa tgctaagcccttgtagtcttgtactgtgccgcgcgtatattttaaccacc actagttgtttctcttttcaaaaacacacaaaaaataatttgttttcgt aacggcgtcaaatctgacggcgtctcaatacgttcaatttttcttttctt tcacatggtttctcatagctttgcattgaccataggtaaagggataagga taaaggtttttttctcttgtttgttttatccttattattcaaaatggataa aaaaacagtcttattttgatttctttgattaaaaaagtcattgaaattca tatttgattttttgctaaatgtcaactcagagacacaaacgtaatgcact gtcgccaatattcatggatcatgaccatgaatatcactagaataattgaa aatcagtaaaatgcaaacaaagcattttctaattaaaacagtcttctaca ttcacttaattggaatttcctttatcaaacccaaagtccaaaacaatcgg caatgttttgcaaaatgttcaaaactattggcgggttggtctatccgaat tgaagatcttttctccatatgatagaccaacgaaattcggcatacgtgtt ttttttttgttttgaaaaccctttaaacaaccttaattcaaaatactaa tgtaactttattgaacgtgcatctaaaaattttgaactttgcttttgaga aataatcaatgtaccaataaagaagatgtagtacatacattataattaaa tacaaaaaaggaatcaccatatagtacatggtagacaatgaaaaacttta aaacatatacaatcaataatactctttgtgcataactttttttgtcgtct cgagtttatatttgagtacttatacaaactattagattacaaactgtgct cagatacattaagttaatcttatatacaagagcactcgagtgttgtcctt aagttaatcttaagatatcttgaggtaaatagaaatagttaactcgtttt

```
tatttctttttttaccatgagcaaaaaaagatgaagtaagttcaaaac gtgacgaatctacatgttactacttagtatgtgtcaatcattaaatcggg aaaacttcatcatttcaggagtactacaaaactcctaagagtgagaacga ctacatagtacatattttgataaaagacttgaaaacttgctaaaacgaat ttgcgaaaatataatcatacaagtagaaccactgatttgatcgaattatt catagctttgtaggatgaacttaactaaataatatctcacaaaagtattg acagtaacctagtactatactatctatgttagaatatgattatgataa tttatcccctcacttattcatatgatttttgaagcaactactttcgtttt tttaacattttctttttggtttttgttaatgaacatatttagtcgtttc ttaattccactcaaatagaaaatacaaagagaactttatttaatagatat gaacataatctcacatcctcctcctaccttcaccaaacactttttacatac actttgtggtctttctttacctaccaccatcaacaacaacaccaagcccc actcacacacacgcaatcacgttaaatctaacgccgtttattatctcatc attcaccaactcccacgtacctaacgccgtttaccttttgccgttggtcc tcatttctcaaaccaaccaaacctctccctcttataaaatcctctctccc ttctttatttcttcctcagcagcttcttctgctttcaattactctcgccg acgattttctcaccggaaaaaaacaatatcattgcggatacacaaactat a
```

Other promoters useful in the practice of the invention are known to those of skill in the art.

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated not present in a high copy number, but is relatively abundant in specific tissues. The promoter and control elements of corresponding genomic clones can then be localized using techniques well known to those of skill in the art.

A p-coumaroyl-CoA:monolignol transferase nucleic acid can be combined with the promoter by standard methods to yield an expression cassette, for example, as described in Sambrook et al. (MOLECULAR CLONING: A LABORATORY MANUAL. Second Edition (Cold Spring Harbor, NY: Cold Spring Harbor Press (1989); MOLECULAR CLONING: A LABORATORY MANUAL. Third Edition (Cold Spring Harbor, NY: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter. The p-coumaroyl-CoA:monolignol transferase nucleic acids can be subcloned downstream from the promoter using restriction enzymes and positioned to ensure that the DNA is inserted in proper orientation with respect to the promoter so that the DNA can be expressed as sense RNA. Once the p-coumaroyl-CoA:monolignol transferase nucleic acid is operably linked to a promoter, the expression cassette so formed can be subcloned into a plasmid or other vector (e.g., an expression vector).

In some embodiments, a cDNA clone encoding a p-coumaroyl-CoA:monolignol transferase protein is isolated from a selected plant tissue, or a nucleic acid encoding a mutant or modified p-coumaroyl-CoA:monolignol transferase protein is prepared by available methods or as described herein. For example, the nucleic acid encoding a mutant or modified p-coumaroyl-CoA:monolignol transferase protein can be any nucleic acid with a coding region that hybridizes to SEQ ID NO:1 or SEQ ID NO:3 and that has p-coumaroyl-CoA:monolignol transferase activity. Using restriction endonucleases, the entire coding sequence for the p-coumaroyl-CoA:monolignol transferase is subcloned downstream of the promoter in a 5' to 3' sense orientation.

Targeting Sequences: Additionally, expression cassettes can be constructed and employed to target the p-coumaroyl-CoA:monolignol transferase nucleic acids to an intracellular compartment within plant cells or to direct an encoded protein to the extracellular environment. This can generally be achieved by joining a DNA sequence encoding a transit or signal peptide sequence to the coding sequence of the p-coumaroyl-CoA:monolignol transferase nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences: When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, California. The 3' nontranslated regulatory sequences can be operably linked to the 3' terminus of the p-coumaroyl-CoA:monolignol transferase nucleic acids by standard methods.

Selectable and Screenable Marker Sequences: In order to improve identification of transformants, a selectable or screenable marker gene can be employed with the expressible p-coumaroyl-CoA:monolignol transferase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Example of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to the one set forth herein below. Therefore, it will be understood that the discussion herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a (3-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (*Am. Soc. Agron.*, Madison, WI), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bo13). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology*. 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to substantially inhibit the translation of an mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells: The present invention generally includes steps directed to introducing p-coumaroyl-CoA:monolignol transferase nucleic acids, such as a preselected cDNA encoding the selected p-coumaroyl-CoA:monolignol transferase enzyme, into a recipient cell to create a transformed cell. In some instances the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant with lignin containing monolignol coumarates (e.g., coniferyl coumarate), wherein the plant has an introduced p-coumaroyl-CoA:monolignol transferase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include grasses (switchgrass, Sorghum, etc.), softwoods, hardwoods, wheat, rice, *Arabidopsis*, tobacco, maize, soybean, Sorghum, and the like. In some embodiments, the plant or cell is a monocotyledon plant or cell. For example, the plant or cell can be a softwood plant or cell, or a maize plant or cell. In some embodiments, the plant or cell is a dicotyledon plant or cell. For example, the plant or cell can be a hardwood plant or cell. The cell(s) may be in a suspension cell culture or may be in an intact plant part, such as an immature embryo, or in a specialized plant tissue, such as callus, such as Type I or Type II callus.

Transformation of the plant cells can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell*. 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspensions, culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Similar tissues can be transformed for softwood or hardwood species. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the p-coumaroyl-CoA:monolignol transferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucuronidase or bar gene engineered for expression in maize. Bacteria were inactivated by ethanol dehydration prior to bombardment. A low level of transient expression of the β-glucuronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS*. 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell*. 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Trans genic Maize: After effecting delivery of a p-coumaroyl-CoA:monolignol transferase nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible p-coumaroyl-CoA:monolignol transferase nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the p-coumaroyl-CoA:monolignol transferase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced p-coumaroyl-CoA:monolignol transferase nucleic acids, the plant is self-pollinated at least once in order to produce a homozygous backcross converted inbred containing the p-coumaroyl-CoA:monolignol transferase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the p-coumaroyl-CoA:monolignol transferase nucleic acids (or the p-coumaroyl-CoA:monolignol transferase enzyme). Transgenic plant and/or seed tissue can be analyzed for p-coumaroyl-CoA:monolignol transferase expression using standard methods such as SDS polyacrylamide gel electrophoresis, liquid chromatography (e.g., HPLC) or other means of detecting a product of p-coumaroyl-CoA:monolignol transferase activity (e.g., coniferyl coumarate).

Once a transgenic seed expressing the p-coumaroyl-CoA:monolignol transferase sequence and having an increase in monolignol coumarates in the lignin of the plant is identified, the seed can be used to develop true breeding plants. The true breeding plants are used to develop a line of plants with an increase in the percent of monolignol coumarates in the lignin of the plant while still maintaining other desirable functional agronomic traits. Adding the trait of increased monolignol coumarate production in the lignin of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of monolignol coumarates in the lignin of the plant. The resulting progeny are then crossed back to the parent that expresses the increased monolignol coumarate trait. The progeny from this cross will also segregate so that some of the progeny carry the trait and some do not. This back-crossing is repeated until an inbred line with the desirable functional agronomic traits, and with expression of the trait involving an increase in monolignol coumarates (e.g., coniferyl coumarate) within the lignin of the plant. Such expression of the increased percentage of monolignol coumarates in plant lignin can be expressed in a dominant fashion.

Subsequent to back-crossing, the new transgenic plants can be evaluated for an increase in the weight percent of monolignol coumarates incorporated into the lignin of the plant. This can be done, for example, by NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama, T. Solution-state 2D NMR of Ball-milled Plant Cell Wall Gels in DMSO-$d_6$. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to oil and/or starch plants (canola, potatoes, lupins, sunflower and cottonseed), forage plants (alfalfa, clover and fescue), grains (maize, wheat, barley, oats, rice, Sorghum, millet and rye), grasses (switchgrass, prairie grass, wheat grass, sudangrass, Sorghum, straw-producing plants), softwood, hardwood and other woody plants (e.g., those used for paper production such as poplar species, pine species, and *eucalyptus*). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *Miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues: To confirm the presence of the p-coumaroyl-CoA:monolignol transferase nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced p-coumaroyl-CoA:monolignol transferase nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the p-coumaroyl-CoA:monolignol transferase nucleic acid in question, they do not provide information as to whether the preselected DNA segment is being expressed. Expression may be evaluated by specifically identifying the protein products of the introduced p-coumaroyl-CoA:monolignol transferase nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the p-coumaroyl-CoA:monolignol transferase such as evaluation by amino acid sequencing following purification. The Examples of this application also provide assay procedures for detecting and quantifying p-coumaroyl-CoA:monolignol transferase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Definitions

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, and/or amplified.

EXAMPLES

Example 1: Identification and Testing of *Panicum virgatum* and *Sorghum bicolor* PMTs This Example illustrates isolation and expression of enzymatically active PMTs from *Panicum virgatum* and *Sorghum bicolor*.

INTRODUCTION

Recent work in plant biomass valorization has focused on the development of co-products to the production of cellulosic biofuels. One method of valorization is to increase the amount of easily clipped-off compounds for up-conversion to commodity chemicals. One such compound is p-coumaric acid (pCA), which can be found on the lignins of many monocot plants, including all grasses. Lignin is comprised predominantly of monolignols (ML) with three primary subunits: p-hydroxyphenyl (H), guaiacyl (G), and syringyl (S). The monolignols are known to form monolignol p-coumarate conjugates (ML-pCA). These units are formed by a specific subclass of BAHD acyl transferases known as p-coumaryl-coenzyme A monolignol transferases (PMTs). Introducing ML-pCAs into plants that don't originally have them has been shown also to improve lignin pretreatment and saccharification.

Methods
Selection of Gene Sequences

Gene sequences from Sorghum, switchgrass, Brachypodium, maize, and rice were identified from NCBI GenBank and Joint Genome Institute Phytozome by their PFAM and BAHD transferase domain identity. Protein sequence comparisons were made with NCBI BLASTP (blast.ncbi.nlm.nih.gov) using default settings. The sequence identity is reported both as a percentage, as well as a fraction, where the numerator is the number of identical residues, and the denominator is the length of the matched region. See Table 1. The nucleic acid coding sequences and amino acid sequences encoded thereby for each of the *Panicum virgatum* (switchgrass) PMT (PvPMT) and the *Sorghum bicolor* (Sorghum) PMT (SbPMT) are provided elsewhere herein. Each of the native genes for the PvPMT, and SbPMT proteins include introns, which are excluded from the sequences provided herein.

Cloning Vector

Coding sequences were synthesized by GenScript Corporation (Piscataway, NJ) and cloned into the wheat germ cell-free expression vector, pEU (Sawasaki, T., Hasegawa, Y., Tsuchimochi, M., Kasahara, Y. and Endo, Y. (2000) Construction of an efficient expression vector for coupled transcription/translation in a wheat germ cell-free system. *Nucleic Acids Symp Ser*, 9-10), which contains an SP6 promoter and omega enhancer sequence from tobacco mosaic virus. Plasmid DNA was purified from *E. coli* using a commercial purification kit, then treated with proteinase K and re-purified to remove residual RNAse activity and to determine concentration of the DNA.

Transcription

Messenger RNA was prepared by adding 1.6 U of SP6 RNA polymerase and 1 U of RNasin RNase inhibitor (Promega Corporation, Madison, WI) to plasmid DNA (0.2 mg/mL or higher) in the presence of 2.5 mM each of UTP, CTP, ATP, and GTP and 20 mM magnesium acetate, 2 mM spermidine HCl, 10 mM DTT, and 80 mM HEPES-KOH, pH 7.8. Transcription reactions were incubated at 37° C. for 4 h and visually monitored for the appearance of insoluble pyrophosphate byproducts, which are indicative of successful transcription.

Cell Free Translation

The active enzymes were produced using a wheat germ cell-free translation bilayer method previously reported (Makino, S., Beebe, E. T., Markley, J. L. and Fox, B. G. (2014) Cell-free protein synthesis for functional and structural studies. *Methods in Molecular Biology*, 1091, 161-178). Briefly, a translation reaction mixture consisting of 60 OD wheat germ extract (CellFree Sciences, Matsuyama, Japan), 0.04 mg/mL creatine kinase, 0.3 mM each amino acid, 12.6 mM HEPES-KOH, pH 7.8, 52.6 mM potassium acetate, 1.3 mM magnesium acetate, 0.2 mM spermidine HCl, 2.1 mM DTT, 0.6 mM ATP, 0.13 mM GTP, 8.4 mM creatine phosphate, and 0.003% sodium azide was prepared and combined with non-purified, fresh transcription at a ratio of 4 parts reaction mix to 1 part transcription. A feeding layer was prepared consisting of 0.3 mM each amino acid, 24 mM HEPES-KOH, pH 7.8, 100 mM potassium acetate, 2.5 mM magnesium acetate, 0.4 mM spermidine HCl, 4 mM DTT, 1.2 mM ATP, 0.25 mM GTP, 16 mM creatine phosphate, and 0.005% sodium azide, of which 125 µL was added to wells of a U-bottom 96-well plate. 25 µL of the denser translation reaction mixture was carefully underlayed below the feeding layer, forming a bilayer. The plate was sealed and incubated at 22° C. for 18 h. The fully-diffused 150-µL bilayer reaction was then harvested and used for expression analysis by SDS-PAGE, and activity screening.

Activity Screening

Figure 2B:
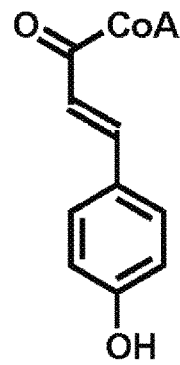
Figure 2C:
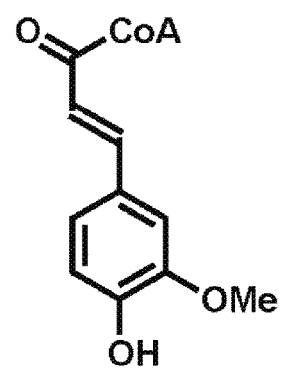
Figure 2D:
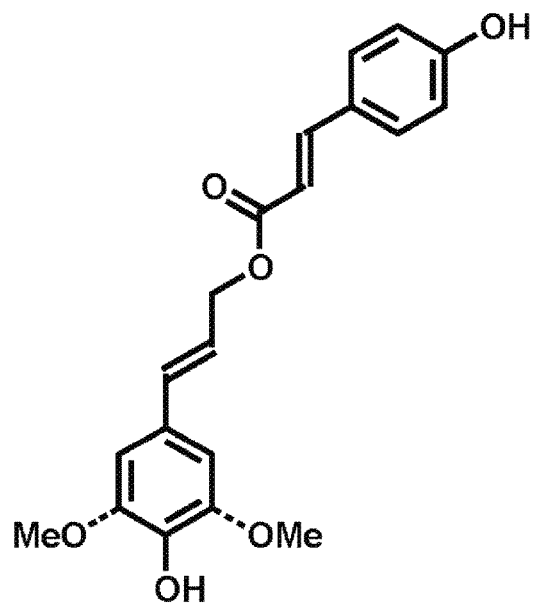
Figure 2E:
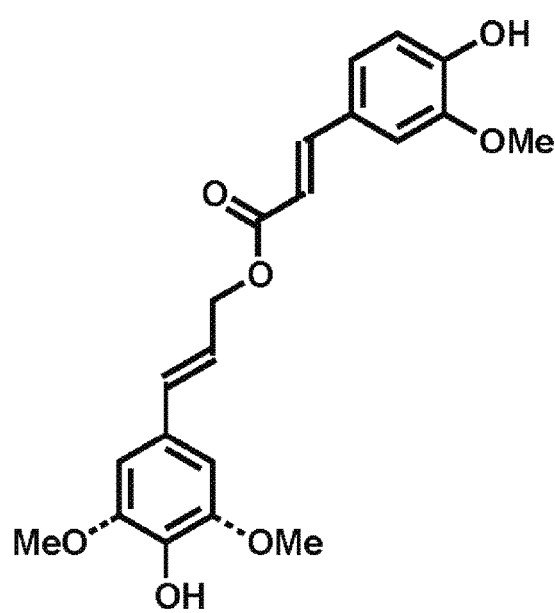

The enzyme mixture was screened for activity with p-coumaroyl-CoA (FIG. 2B) and feruloyl-CoA (FIG. 2C) and all three monolignols (FIG. 2A) (p-coumaryl, coniferyl, and sinapyl alcohol). Each enzyme was tested individually alongside positive and negative controls following the procedure previously reported (Withers, S., Lu, F., Kim, H., Zhu, Y., Ralph, J. and Wilkerson, C. G. (2012) Identification of a grass-specific enzyme that acylates monolignols with p-coumarate. *Journal of Biological Chemistry,* 287, 8347-8355). Briefly, the assay was initiated by adding 10 µL of wheat germ cell-free translation containing one of the PMT enzymes at a concentration of 1.5-2 µM to a reaction containing 50 mM sodium phosphate buffer, pH 6, 1 mM dithiothreitol (DTT), 1 mM CoA thioester, 1 mM monolignol mixture (each monolignol at 1 mM concentration), and deionized water in a final volume of 50 µL. After a 30-min incubation, the reaction was stopped by the addition of an equal volume 100 mM hydrochloric acid. Reaction products were solubilized by adjusting the solution to 50% methanol. An identical assay with no enzyme added was performed for every reaction. Samples were filtered through 0.2 µm filters prior to analysis by liquid chromatography-mass spectrometry (LC-MS).

Results

Figure 3A:
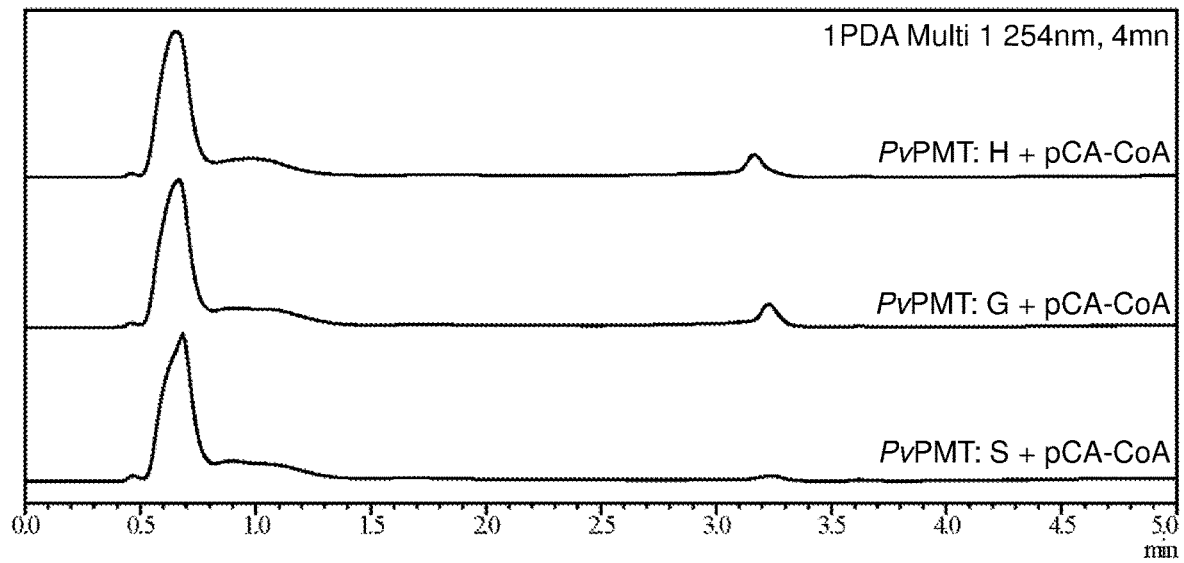
FIGS. 3A and 3B show liquid chromatography-mass spectrometry (LC-MS) traces of chemical species present after incubating a *Panicum virgatum* (switchgrass) PMT (PvPMT) with each of p-hydroxycinnamyl alcohol (H), coniferyl alcohol (G), and sinapyl alcohol (S) and either p-coumaryl-CoA (pCA-CoA) (FIG. 3A) or feruloyl-CoA (FA-CoA) (FIG. 3B).
Figure 4A:
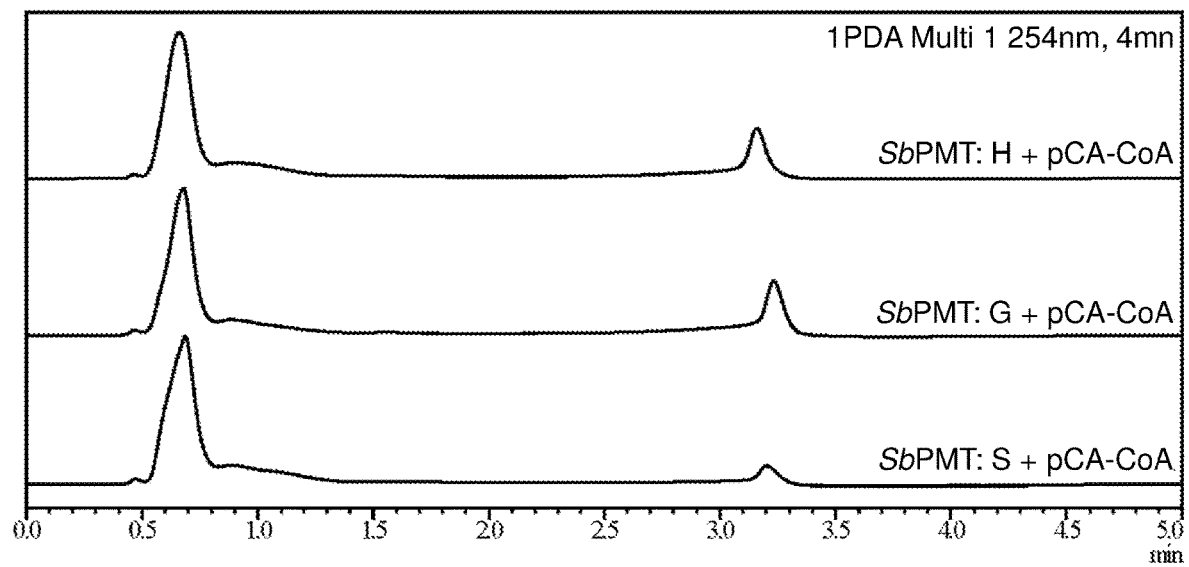
FIGS. 4A and 4B show LC-MS traces of chemical species present after incubating a *Sorghum bicolor* (Sorghum) PMT (SbPMT) with each of p-hydroxycinnamyl alcohol (H), coniferyl alcohol (G), and sinapyl alcohol (S) and either p-coumaryl-CoA (pCA-CoA) (FIG. 4A) or feruloyl-CoA (FA-CoA) (FIG. 4B).
Figure 5:
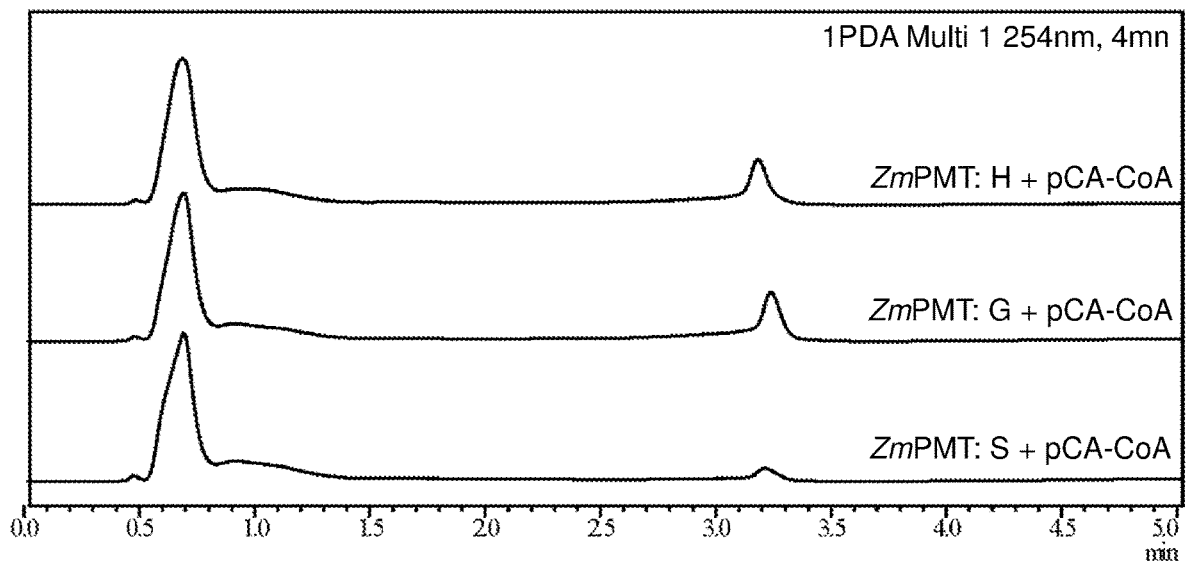
FIG. 5 shows LC-MS traces of chemical species present after incubating a *Zea mays* (maize) PMT (ZmPMT) with each of p-hydroxycinnamyl alcohol (H), coniferyl alcohol (G), and sinapyl alcohol (S) and p-coumaryl-CoA (pCA-CoA).
Figure 6:
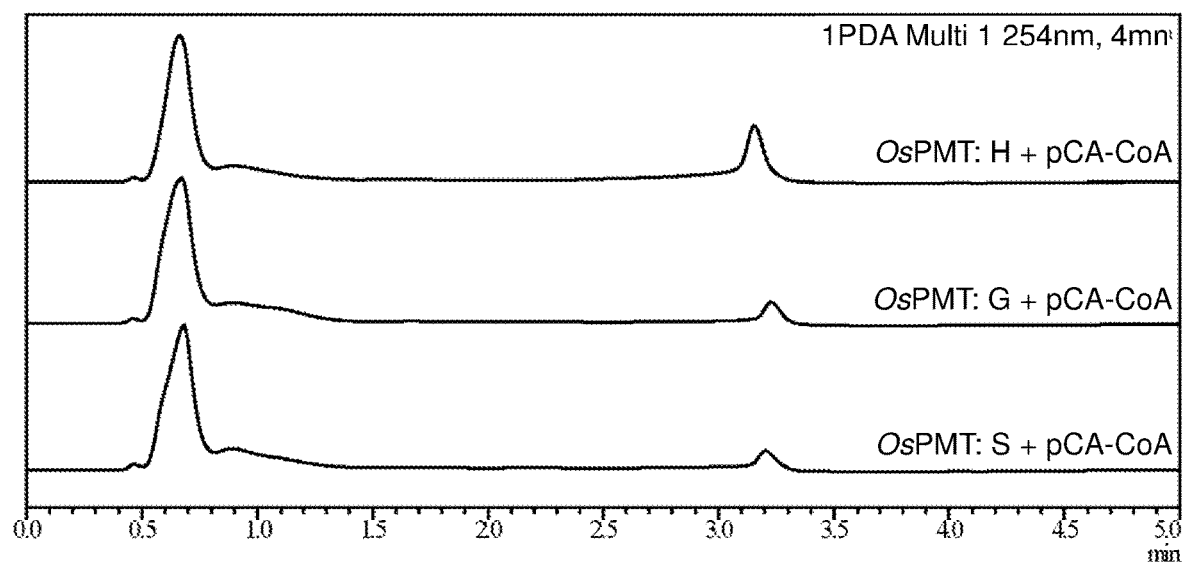
FIG. 6 shows LC-MS traces of chemical species present after incubating an *Oryza sativa* PMT (OsPMT) with each of p-hydroxycinnamyl alcohol (H), coniferyl alcohol (G), and sinapyl alcohol (S) and p-coumaryl-CoA (pCA-CoA).
Figure 7:
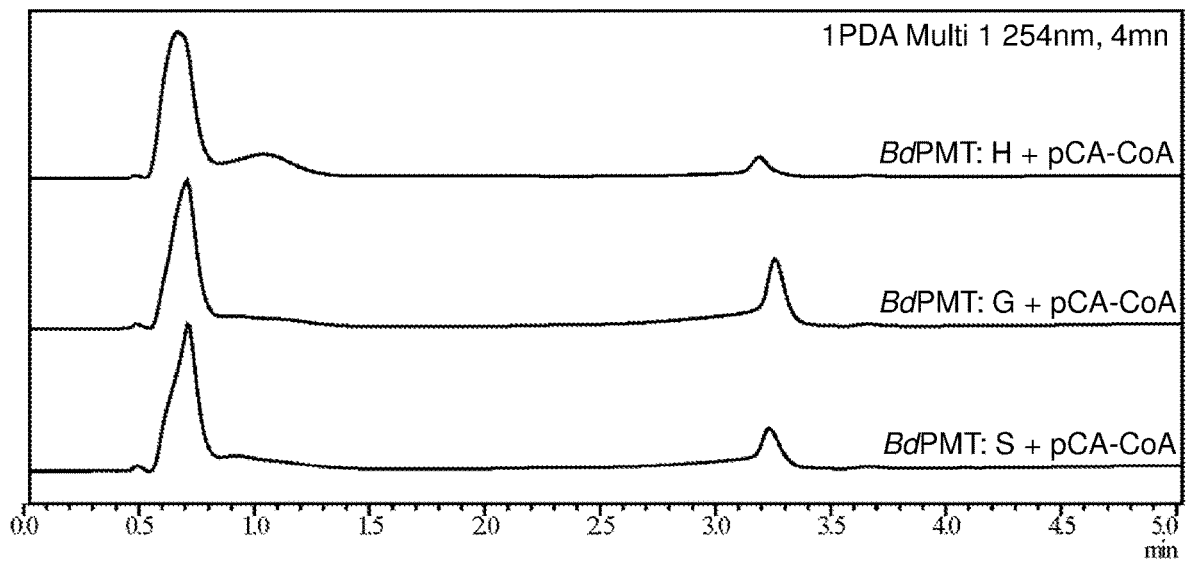
FIG. 7 shows LC-MS traces of chemical species present after incubating a Brachypodium distachyon PMT (BdPMT1) with each of p-hydroxycinnamyl alcohol (H), coniferyl alcohol (G), and sinapyl alcohol (S) and p-coumaryl-CoA (pCA-CoA).
Figure 8:
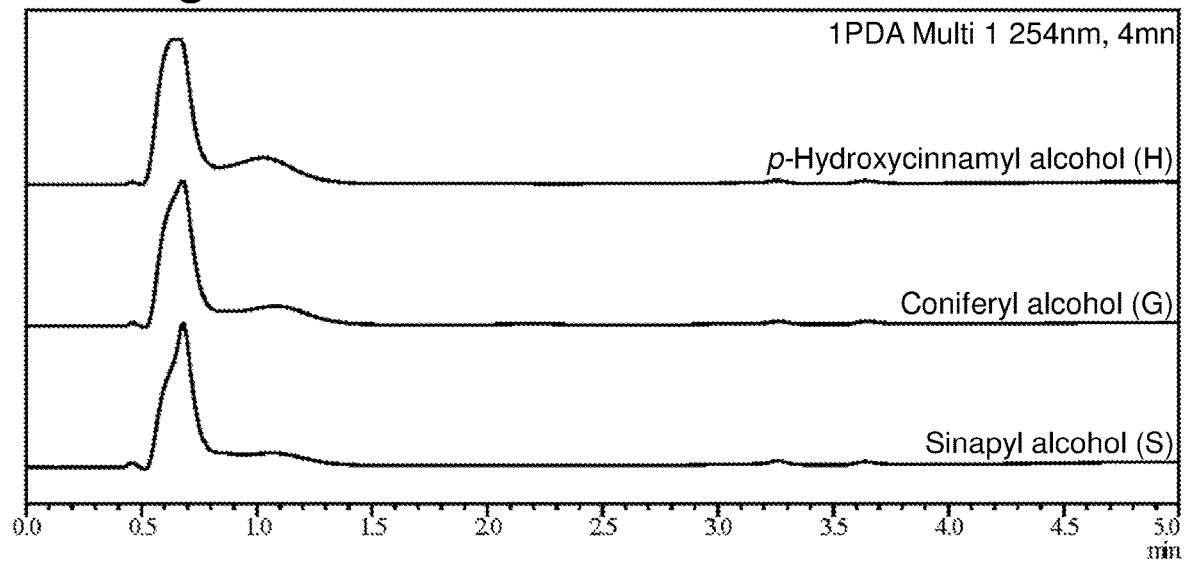
FIG. 8 shows LC-MS traces of p-hydroxycinnamyl alcohol (H), coniferyl alcohol (G), and sinapyl alcohol (S).

As shown in Table 1 and FIGS. 3A and 4A, both PvPMT and SbPMT are active PMTs, coupling monolignols to p-coumaroyl-CoA. These two enzymes increase the known collection of PMTs to six, adding to ZmPMT/pCAT (GRMZM2G028104_P01) from maize (Table 1, FIG. 5), OsPMT (LOC_Os01g18744) from rice (Table 1, FIG. 6), and BdPMT1 (Bradi2g36910.1) and BdPMT2 (Bradi1g36980.1) from Brachypodium (Table 1, FIG. 7). For a description of OsPMT, BdPMT1, BdPMT2, and ZmPMT, see Withers et al. 2012 (Withers, S.; Lu, F.; Kim, H.; Zhu, Y.; Ralph, J.; Wilkerson, C. G., Identification of a grass-specific enzyme that acylates monolignols with p-coumarate. *J. Biol. Chem.* 2012, 287 (11), 8347-8355), Petrik et al. 2014 (Petrik, D. L.; Karlen, S. D.; Cass, C. L.; Padmakshan, D.; Lu, F.; Liu, S.; Le Bris, P.; Antelme, S.; Santoro, N.; Wilkerson, C. G.; Sibout, R.; Lapierre, C.; Ralph, J.; Sedbrook, J. C., p-Coumaroyl-CoA:Monolignol Transferase (PMT) acts specifically in the lignin biosynthetic pathway in Brachypodium distachyon. *The Plant Journal* 2014, 77 (5), 713-726), Petrik et al. 2016 (Petrik, D. L.; Cass, C. L.; Padmakshan, D.; Foster, C. E.; Vogel, J. P.; Karlen, S. D.; Ralph, J.; Sedbrook, J. C., BdCESA7, BdCESA8, and BdPMT utility promoter constructs for targeted expression to secondary cell-wall-forming cells of grasses. Frontiers in *Plant Science* 2016, 7, 1-14), Sibout et al. 2016 (Sibout, R.; Le Bris, P.; Legee, F.; Cezard, L.; Renault, H.; Lapierre, C., Structural redesigning *Arabidopsis* lignins into alkali-soluble lignins through the expression of p-coumaroyl-CoA: monolignol transferase PMT. *Plant Physiol.* 2016, 170 (3), 1358-66), and Marita et al. 2014 (Marita, J. M.; Hatfield, R. D.; Rancour, D. M.; Frost, K. E., Identification and suppression of the p-coumaroyl CoA:hydroxycinnamyl alcohol transferase in *Zea mays* L. *Plant J.* 2014, 78 (5), 850-864).

Figure 3B:
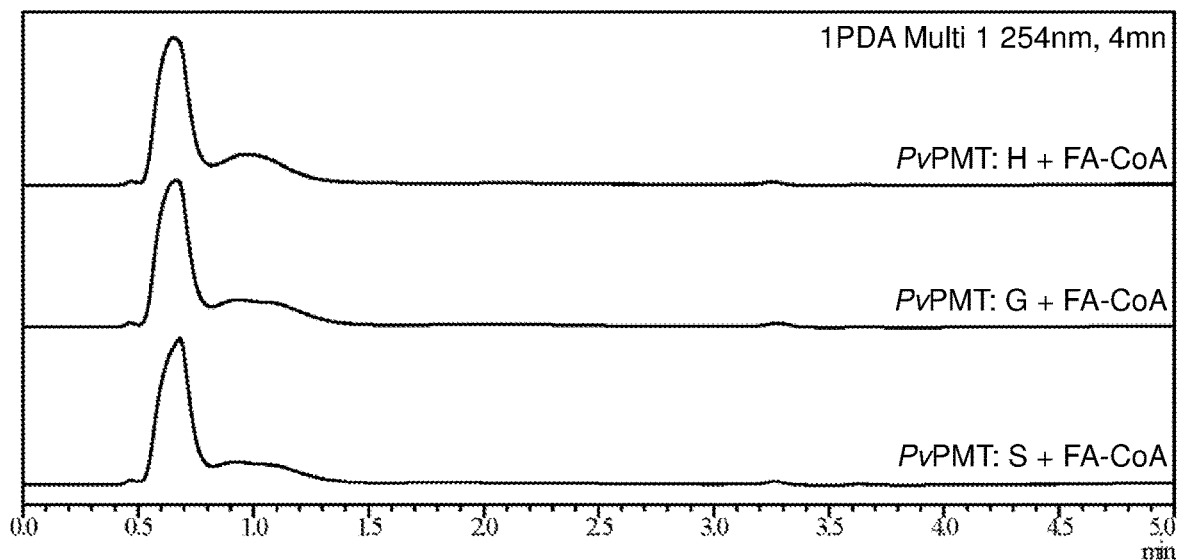
Figure 4B:
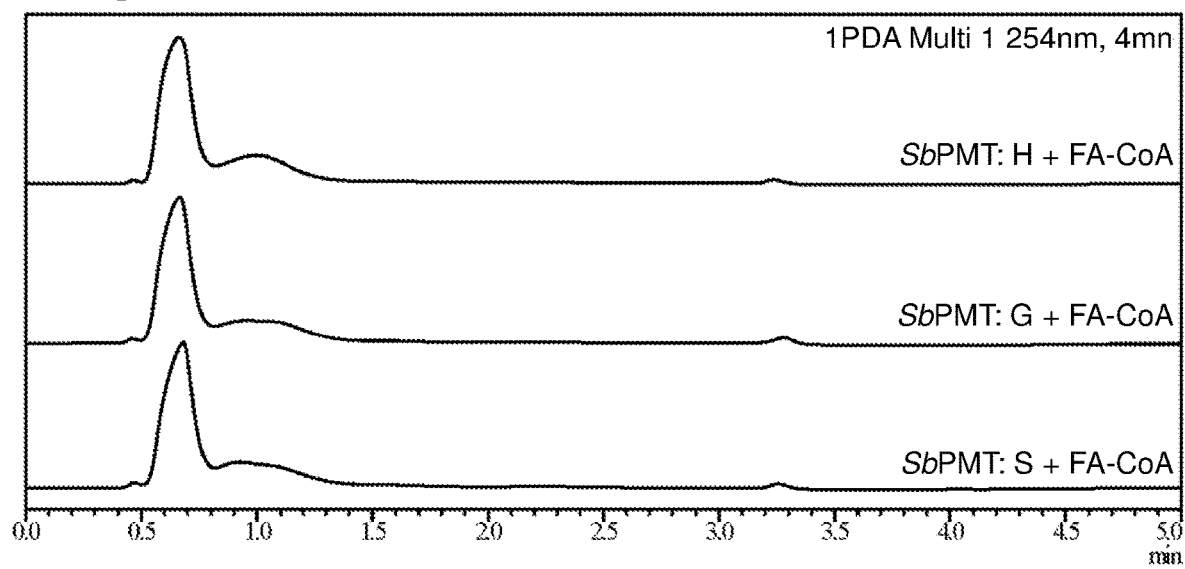

PvPMT and SbPMT have limited to no feruloyl-CoA monolignol transferase activity (Table 1 and FIGS. 3B and 4B). This finding is in contrast to that of OsPMT1 which has been shown to have some feruloyl-CoA:monolignol transferase (FMT) activity under the assay conditions (Withers, S.; Lu, F.; Kim, H.; Zhu, Y.; Ralph, J.; Wilkerson, C. G., Identification of a grass-specific enzyme that acylates monolignols with p-coumarate. *J. Biol. Chem.* 2012, 287 (11), 8347-8355).

TABLE 1

PMT enzymes similarity and activity.

| | | | | % Identity (Sequence Coverage) | | | | Activity with H, G, S | |
| --- | --- | --- | --- | --- | --- | --- | --- | --- | --- |
| | | | AA | vs. | vs. | vs. | vs. | | |
| Enzyme | Species | Accession # | length | OsPMT | ZmPMT | BdPMT1 | BdPMT2 | pCA-CoA | FA-CoA |
| OsPMT | *Oryza sativa* | LOC_Os01g18744 | 440 | 100% (440/440) | 64% (282/441) | 62% (280/452) | 45% (197/439) | + | + |
| ZmPMT | *Zea mays* | GRMZM2G028104_P01 | 436 | 64% (283/441) | 100% (436/436) | 70% (306/439) | 46% (196/426) | + | + |
| BdPMT1 | *Brachypodium distachyon* | Bradi2g36910.1 | 450 | 64% (271/421) | 70% (306/439) | 100% (450/450) | 43% (177/414) | + | |
| BdPMT2 | *Brachypodium distachyon* | Bradi1g36980.1 | 432 | 45% (197/439) | 46% (196/426) | 43% (177/414) | 100% (432/432) | + | |
| PvPMT | *Panicum virgatum* | Pavir.J00672.1 | 428 | 62% (274/439) | 78% (338/431) | 70% (311/444) | 48% (203/422) | + | − |
| SbPMT | *Sorghum bicolor* | Sb09g002910.1 | 437 | 64% (282/442) | 85% (374/438) | 70% (313/444) | 45% (194/427) | + | − |

H, p-hydroxycinnamyl alcohol (p-coumaryl alcohol);
G, coniferyl alcohol;
S, sinapyl alcohol;
pCA-CoA, p-coumaroyl-CoA;
FA-CoA, feruloyl-CoA.

Figure 9:
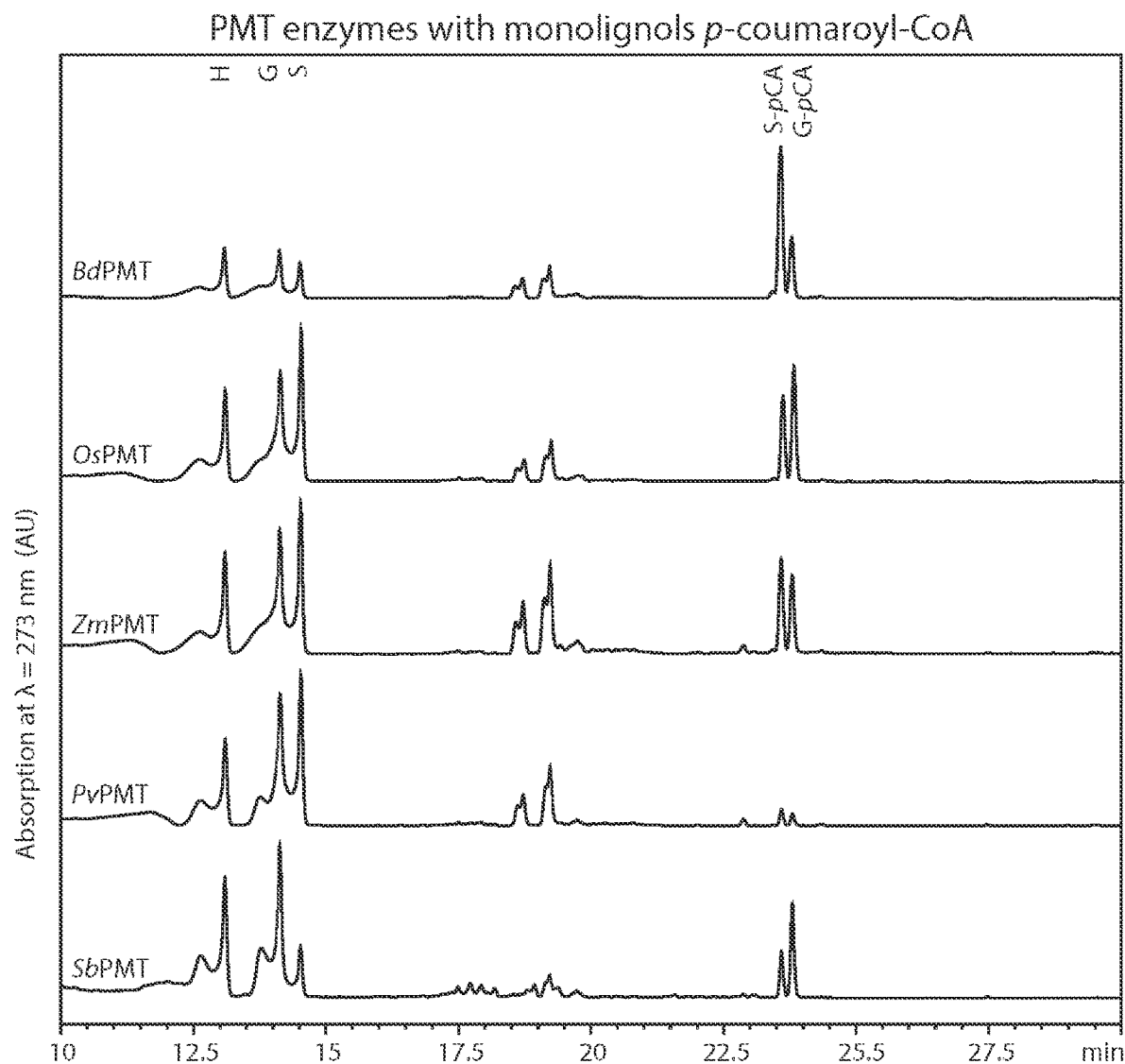
FIG. 9 shows LC-MS traces of chemical species present after incubating each of BdPMT, OsPMT, ZmPMT, PvPMT, and SbPMT with p-hydroxycinnamyl alcohol (H), coniferyl alcohol (G), sinapyl alcohol (S), and p-coumaroyl-CoA. Products include sinapyl coumarate (S-pCA) and coniferyl coumarate (G-pCA).
Figure 10:
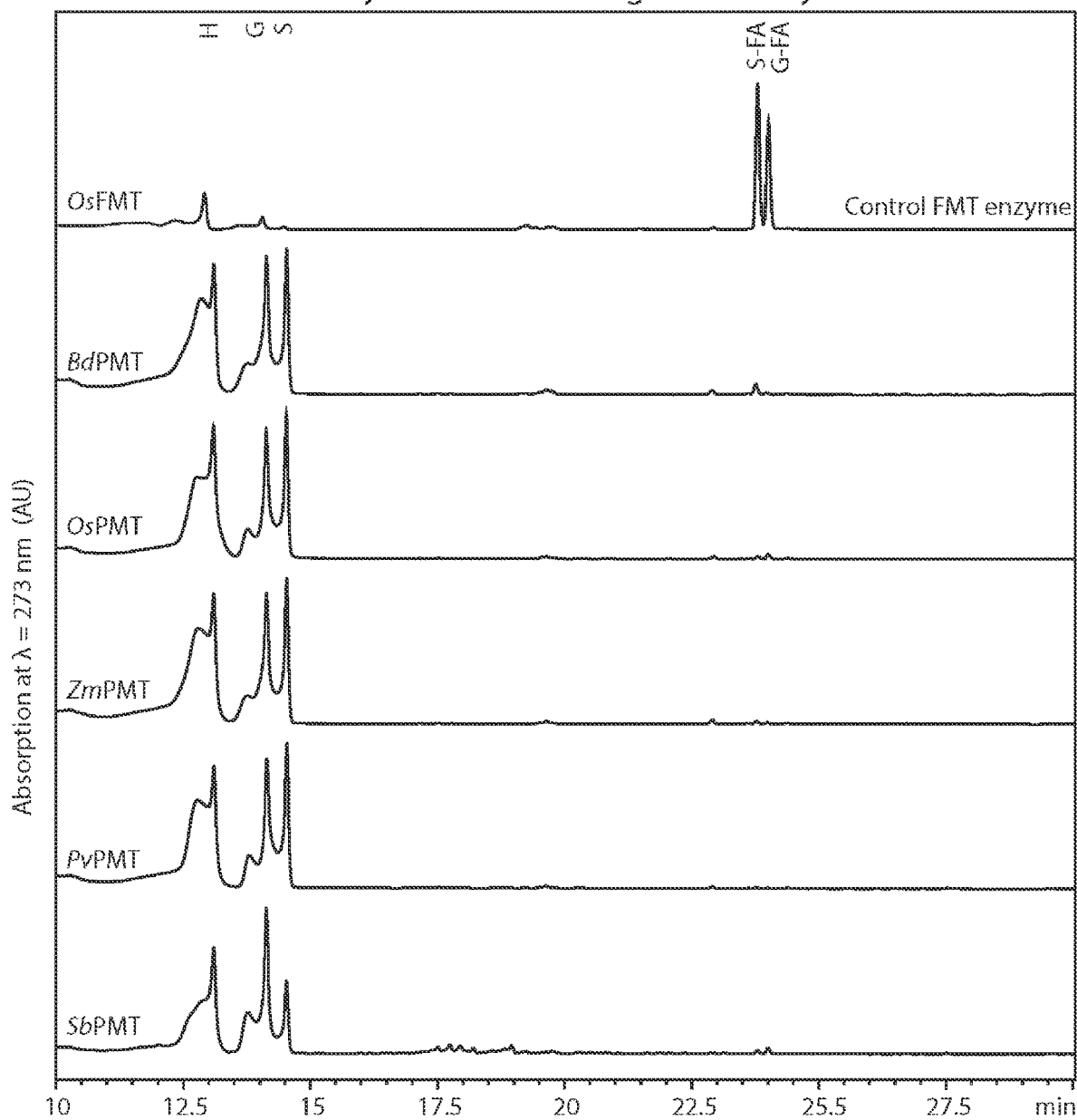
FIG. 10 shows LC-MS traces of chemical species present after incubating each of OsFMT, BdPMT, OsPMT, ZmPMT, PvPMT, and SbPMT with p-hydroxycinnamyl alcohol (H), coniferyl alcohol (G), sinapyl alcohol (S), and feruloyl-CoA. Products include sinapyl ferulate (S-FA) and coniferyl ferulate (G-FA).

To confirm the different activity profiles for the PMT enzymes with regard to their ability to use feruloyl-CoA and p-coumaroyl-CoA and, specifically, which monolignol substrates are preferred, we used the Joint Genome Institute platform to synthesize and clone the genes, and then expressed them in the wheat germ cell-free translation system in order to test the activity of the enzymes. To the mixture of enzymes produced from the cell-free system, which included putative PMT enzymes of interest, we added a mixture of all three lignin monomers (H, G, and S monolignols) and various CoA ester substrates, including p-coumaroyl-CoA and feruloyl-CoA. The two putative PMT enzymes (SbPMT and PvPMT from Sorghum and switchgrass, respectively) were found to produce monolignol p-coumarate conjugates when fed monolignols and p-coumaroyl-CoA (FIG. 9). SbPMT and PvPMT showed little to no activity when fed monolignols and feruloyl-CoA, contrary to OsFMT (Karlen, S. D., Zhang, C., Peck, M. L., Smith, R. A., Padmakshan, D., Helmich, K. E., Free, H. C. A., Lee, S., Smith, B. G., Lu, F., Sedbrook, J. C., Sibout, R., Grabber, J. H., Runge, T. M., Mysore, K. S., Harris, P. J., Bartley, L. E. and Ralph, J. (2016) Monolignol ferulate conjugates are naturally incorporated into plant lignins. Science Advances, 2, e1600393), which was used as a positive control for monolignol ferulate production (FIG. 10).

Example 2: Analysis of in Planta Expression of *Panicum virgatum* and *Sorghum bicolor* PMTs The data in Example 1 indicate that the SbPMT and PvPMT enzymes function as feruloyl-CoA monolignol transferases. The present example shows expression and activity of these enzymes in planta.

Methods

Gateway cloning technology (Invitrogen) was used to generate constructs to express the SbPMT, and PvPMT genes in planta. The gateway constructs generated were: ProUBQ10: SbPMT-GFP and ProUBQ10: PvPMT-GFP (pUBC:GFP; (Grefen, C., Donald, N., Hashimoto, K., Kudla, J., Schumacher, K., & Blatt, M. R. (2010) *The Plant Journal* 64, 355-365)). The SbPMT plant expression construct was introduced into *Agrobacterium tumefaciens* strain GV3101 and transformed into *Arabidopsis thaliana*, ecotype Col-0, using the floral dip method (Clough, S. J. & Bent, A. F. (1998) *Plant Journal* 16, 735-743) to generate transgenic plants.

Transgenic seeds were sterilized with chlorine gas for 4 h prior to plating on half-strength Murashige and Skoog media (Sigma-Aldrich) with 25 mg/L glufosinate-ammonium (Basta; Fisher) to select for transformants. Seedlings were grown under long-day conditions (16 h light, 8 h dark, 20° C.) for one week and then positive transformants were screened for the presence of GFP. Whole seedlings were placed on a glass slide in water and examined for the presence of GFP using an epifluorescent microscope and a GFP excitation/emission filter set (488/525). Seedlings that showed resistance to Basta and strong fluorescence under the GFP filters were planted in soil and grown under long-day conditions.

After 4-5 weeks, 2-3 small leaves were collected from each plant for genomic DNA extraction and genotyping PCR. Briefly, the leaves were ground in Shorty extraction buffer (200 mM Tris-HCl, 250 mM NaCl, 25 mM NaEDTA, 0.5% SDS) and the samples were then centrifuged for 3 min. The supernatant was collected and, after the addition of isopropanol (300 µL) to precipitate the DNA, centrifuged again. The DNA pellet was washed with 70% ethanol (500 µL), centrifuged again, and then the pellets were allowed to air dry. The DNA was re-suspended in 100 µL of TE buffer, pH 8.0. Genotyping PCR using MangoTaq polymerase (Bioline) was performed to confirm the presence of SbPMT in *Arabidopsis*. Primers were designed to amplify part of Actin2 (At3g18780) from *Arabidopsis* as a positive control for DNA quality. The primers used to amplify the genes are listed in Table 2. PCR cycling conditions were as follows: 94° C. 1 min, (94° C. 10 s, 48° C. 15 s, 72° C. 45 s)×32, 72° C. 5 min, then cooled to 4° C.

TABLE 2

Primer sequences used for amplification of control (Actin 2) and transgenic SbPMT in *Arabidopsis* genotyping study.

| Gene | Primers (5'-3') |
|---|---|
| Actin2-F | CCAGAAGGATGCATATGTTGGTGA (SEQ ID NO:6) |
| Actin2-R | GAGGAGCCTCGGTAAGAAGA (SEQ ID NO:7) |
| SbPMT-F | ATGGGCACAATCGATGATA (SEQ ID NO:8) |
| SbPMT-R | AGCTGAGCAGGGCTG (SEQ ID NO:9) |

HPLC analysis was performed on a Shimadzu LCMS8040 equipped with a Prominence LC20. The mobile phase was a binary gradient of acetonitrile and water, pumped at 0.7 mL/min through a Phemonenex Kinetex 5µ XB-C18, 100 Å, 250×4.6 mm column (P/N: 00G-4605-E0) equipped with a guard column. The LC program was initially held at 5% acetonitrile for 2 min, then ramped over 28 min to 100% acetonitrile, held there for 4 min and ramped back over 1 min to 5% acetonitrile and held for 15 min. The samples were injected with an autoinjector onto the XB-C18 column and the eluent then flowed through a PDA detector scanning from 250-400 nm and into the MS ionization source operating in DUIS (ESI/APCI) mode with 2.5 L/min nebulizing gas, 15 L/min drying gas, 250° C. DL temperature, and 400° C. heat block. The MS scanned the ions in negative-ion mode from 120-600 m/z. Elution times for the analytes are reported in Table 3.

TABLE 3

Retention times for the monolignols and monolignol conjugates.

| Compound | Retention time |
|---|---|
| p-coumaryl alcohol | 13.07 min |
| coniferyl alcohol | 14.11 min |
| sinapyl alcohol | 14.51 min |
| sinapyl p-coumarate | 23.59 min |
| coniferyl p-coumarate | 23.79 min |
| sinapyl ferulate | 23.73 min |
| coniferyl ferulate | 23.94 min |

Results

The in vitro data shown in Example 1 strongly indicates that the SbPMT and PvPMT enzymes functioning specifically as p-coumaroyl-CoA monolignol transferases. The present example shows the activity of these enzymes in planta. The SbPMT gene was cloned into the pUBC-GFP destination vector and transformed into *Arabidopsis thaliana*. The PvPMT gene can similarly be cloned into the pUBC-GFP vector, and the construct can similarly be transformed into *Arabidopsis*. *Arabidopsis* was used in this study because it is a useful model organism when studying novel monolignol conjugates. As noted in Smith et al. (Smith, R. A., Gonzales-Vigil, E., Karlen, S. D., Park, J.-Y., Lu, F., Wilkerson, C. G., Samuels, L., Mansfield, S. D., & Ralph, J. (2015) *Plant Physiology* 169, 2992-3001), *Arabidopsis* does not produce detectable levels of monolignol p-coumarates, thereby making the presence and production of monolignol p-coumarates through the putative PMT enzymes more apparent. The SbPMT gene was expressed under the control of the *Arabidopsis* Ubiquitin 10 promoter and fused to a green fluorescent protein (GFP) at the C-terminus. The ubiquitous promoter was because to achieve the highest expression level possible, with the assumption that it would lead to higher levels of the conjugates. The C-terminal GFP tag allows us to confirm that the PMT enzyme is being produced by the plant and also determine the intracellular location of the enzyme.

Seeds were plated on media containing Basta antibiotic to select for seedlings that contained the proUBQ10-SbPMT-GFP construct. Before planting, all seedlings were subjected to fluorescence microscopic analysis to confirm the presence of GFP (as a proxy for the presence of the PMT enzyme). Following the development of a healthy rosette (4 weeks after planting), 2-3 small leaves were dissected from each plant and used for genotyping analysis to confirm the presence of the PMT gene in the plants. Plants that did not express the PMT gene were marked as wild-type and are be used as control plants during the chemical analysis of lignin. The genotyping analysis confirmed the SbPMT gene has been successfully transformed into *Arabidopsis*. The SbPMT gene was able to be amplified from the genomic DNA of respective transgenic plants and was not present in wild-type plants. Together with the GFP screening, these data indicate that the transgene is present in the transgenic *Arabidopsis* and that the protein is being expressed.

Transgenic plants continue to grow under long-day conditions until senescence, at which point the plants are harvested for chemical analysis. Wild-type and transgenic plant samples are ground and solvent extracted to remove water-, ethanol-, and acetone-soluble compounds (basically isolating the plant cell wall). The ground, dried cell wall samples are then be subjected to derivatization followed by reductive cleavage (DFRC) lignin analysis (Karlen, S. D., Zhang, C., Peck, M. L., Smith, R. A., Padmakshan, D., Helmich, K. E., Free, H. C. A., Lee, S., Smith, B. G., Lu, F., et al. (2016) Science Advances 2, e1600393: 1600391-1600399; Lu, F. & Ralph, J. (1997) *Journal of Agricultural and Food Chemistry* 45, 2590-2592; Lu, F. & Ralph, J. (1999) *Journal of Agricultural and Food Chemistry* 47, 1988-1992). This assay has been shown to yield peaks that are diagnostic for not only the production of monolignol conjugates (monolignol ferulates and monolignol p-coumarates), but also their incorporation into the lignins of transgenic *Arabidopsis thaliana* (Smith, R. A., Gonzales-Vigil, E., Karlen, S. D., Park, J.-Y., Lu, F., Wilkerson, C. G., Samuels, L., Mansfield, S. D., & Ralph, J. (2015) *Plant Physiology* 169, 2992-3001; Smith, R. A., Scheutz, M., Karlen, S. D., Bird, D., Tokunaga, N., Sato, Y., Mansfield, S. D., Ralph, J., & Samuels, A. L. (2017) Plant Physiology 174, 1028-1036). DFRC analysis is expected to confirm that the SbPMT enzyme produced by the transgenic *Arabidopsis thaliana* plants have the expected PMT activity in planta and that monolignol p-coumarates will be produced.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to summarize some aspects of the invention according to the foregoing description given in the specification.

Statements of a First Set of Embodiments of the Invention

1. An isolated nucleic acid encoding a p-coumaroyl-CoA: monolignol transferase wherein the nucleic acid can selectively hybridize to a DNA with a SEQ ID NO:1 or SEQ ID NO:3 sequence.
2. The isolated nucleic acid of statement 1, wherein the nucleic acid selectively hybridizes to a DNA with a SEQ ID NO:1 or SEQ ID NO:3 sequence under stringent hybridization conditions.
3. The isolated nucleic acid of statement 2, wherein the stringent hybridization conditions comprise a wash in 0.1×SSC, 0.1% SDS at 65° C.
4. The isolated nucleic acid of any of statements 1-3, wherein the nucleic acid that selectively hybridizes to a DNA with a SEQ ID NO:1 or SEQ ID NO:3 sequence has at least about 70% sequence identity with SEQ ID NO:1 or SEQ ID NO:3.
5. The isolated nucleic acid of any of statements 1-4, wherein the nucleic acid encodes a p-coumaroyl-CoA: monolignol transferase that can catalyze the synthesis of monolignol coumarate(s) from monolignol(s) and coumaroyl-CoA.
6. The isolated nucleic acid of statement 5, wherein the monolignol is coniferyl alcohol, p-coumaryl alcohol, sinapyl alcohol or a combination thereof.
7. The isolated nucleic acid of any of statements 1-6, wherein the nucleic acid encodes a p-coumaroyl-CoA: monolignol transferase polypeptide with a SEQ ID NO:2 or SEQ ID NO:4 sequence.
8. The isolated nucleic acid of any of statements 1-7, wherein the nucleic acid encodes a p-coumaroyl-CoA: monolignol transferase that can catalyze the synthesis of monolignol coumarate(s) from a monolignol(s) and coumaroyl-CoA with at least about 50% of the activity of a p-coumaroyl-CoA:monolignol transferase with the SEQ ID NO:2 or SEQ ID NO:4.
9. A transgenic plant cell comprising the isolated nucleic acid of any of statements 1-8.
10. A transgenic plant comprising the plant cell of statement 9 or the isolated nucleic acid of any of statements 1-8.
11. An expression cassette comprising the p-coumaroyl-CoA:monolignol transferase nucleic acid of any of statements 1-8 operably linked to a promoter functional in a host cell.
12. The expression cassette of statement 11, which further comprises a selectable marker gene.
13. The expression cassette of statement 11 or 12, further comprising plasmid DNA.
14. The expression cassette of any of statements 11-13, wherein the expression cassette is within an expression vector.
15. The expression cassette of any of statements 11-14, wherein the promoter is a promoter functional during plant development or growth.
16. The expression cassette of any of statements 11-15, wherein the promoter is a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene or actin promoter from rice.
17. A plant cell comprising the expression cassette of any of statements 11-16.
18. The plant cell of statement 17, wherein the plant cell is a monocot cell.
19. The plant cell of statement 17, wherein the plant cell is a maize, grass or softwood cell.
20. The plant cell of statement 17, wherein the plant cell is a dicot cell.
21. The plant cell of statement 17, wherein the plant cell is a hardwood cell.
22. A plant comprising the expression cassette of any of statements 11-16.
23. The plant of statement 22, wherein the plant is a monocot.
24. The plant of statement 22, wherein the plant is a grass, maize or softwood.
25. The plant of statement 22, wherein the plant is a gymnosperm.
26. The plant of statement 22, wherein the plant is a dicot.
27. The plant of statement 22, wherein the dicot is a hardwood.
28. A method for incorporating monolignol coumarates into lignin of a plant, comprising:
a) stably transforming plant cells with the expression cassette of any of statements 11-16 to generate transformed plant cells;
b) regenerating the transformed plant cells into at least one transgenic plant, wherein p-coumaroyl-CoA: monolignol transferase is expressed in at least one transgenic plant in an amount sufficient to incorporate monolignol coumarates into the lignin of the transgenic plant.
29. The method of statement 28, wherein the transgenic plant is fertile.
30. The method of statement 28 or 29, further comprising recovering transgenic seeds from the transgenic plant, wherein the transgenic seeds comprise the nucleic acid encoding a p-coumaroyl-CoA:monolignol transferase.
31. The method of any of statements 28-30, wherein the plant is a monocot.
32. The method of any of statements 28-31, wherein the plant is a grass, maize or softwood plant.
33. The method of any of statements 28-32, wherein the plant is a gymnosperm.
34. The method of statement 28, wherein the plant is a dicot.
35. The method of statement 34, wherein the dicot plant is a hardwood.
36. The method of any of statements 28-35, wherein the lignin in the plant comprises at least 1% monolignol coumarate.
37. The method of any of statements 28-36, wherein the lignin in the plant comprises at least 5% monolignol coumarate.
38. The method of any of statements 28-37, wherein the lignin in the plant comprises at least 10% monolignol coumarate.
39. The method of any of statements 28-38, wherein the lignin in the plant comprises at least 20% monolignol coumarate.
40. The method of any of statements 28-39, wherein the lignin in the plant comprises at least 25% monolignol coumarate.
41. The method of any of statements 28-40, wherein the lignin in the plant comprises about 1-30% monolignol coumarate, or about 2-30% monolignol coumarate.
42. The method of any of statements 28-41, further comprising breeding a fertile transgenic plant to yield a progeny plant that has an increase in the percentage of monolignol coumarates in the lignin of the progeny plant relative to the corresponding untransformed plant.

43. The method of any of statements 28-42, further comprising breeding a fertile transgenic plant to yield a progeny plant that has an increase in the percentage of monolignol coumarates in the lignin of the progeny plant as a dominant trait while still maintaining functional agronomic characteristics relative to the corresponding untransformed plant.
44. The method of any of statements 28-43, wherein the transformed plant cell is transformed by a method selected from the group consisting of electroporation, microinjection, microprojectile bombardment, and liposomal encapsulation.
45. The method of any of statements 28-44, further comprising stably transforming the plant cell with at least one selectable marker gene.
46. A fertile transgenic plant having an increased percent of monolignol coumarates in the plant's lignin, the genome of which is stably transformed by the nucleic acid of any of statements 1-8, wherein the nucleic acid is operably linked to a promoter functional in a host cell, and wherein the p-coumaroyl-CoA:monolignol transferase nucleic acid is transmitted through a complete normal sexual cycle of the transgenic plant to the next generation.
47. The plant of statement 46, wherein the plant is a monocot.
48. The plant of statement 46, wherein the plant is a grass, maize or softwood.
49. The plant of statement 46, wherein the plant is a gymnosperm.
50. The plant of statement 46, wherein the plant is a dicot.
51. The plant of statement 46, wherein the percent of monolignol coumarates in the plant's lignin is increased relative to the corresponding untransformed plant.
52. The plant of any of statements 46-51, wherein the percent of monolignol coumarates in the plant's lignin is increased by at least 1% relative to the corresponding untransformed plant.
53. The plant of any of statements 46-52, wherein the percent of monolignol coumarates in the plant's lignin is increased by at least 2-5% relative to the corresponding untransformed plant.
54. The plant of any of statements 46-53, wherein the lignin in the plant comprises at least 1% monolignol coumarates.
55. The plant of any of statements 46-54, wherein the lignin in the plant comprises at least 5% monolignol coumarates.
56. The plant of any of statements 46-55, wherein the lignin in the plant comprises at least 10% monolignol coumarates.
57. The plant of any of statements 46-56, wherein the lignin in the plant comprises at least 20% monolignol coumarates.
58. The plant of any of statements 46-57, wherein the lignin in the plant comprises at least 25% monolignol coumarates.
59. The plant of any of statements 46-58, wherein the lignin in the plant comprises about 1-30% monolignol coumarates.
60. A lignin isolated from a transgenic plant comprising the isolated nucleic of any of statements 1-8.
61. A method of making a product from a transgenic plant comprising:

(a) providing or obtaining a transgenic plant that includes an isolated nucleic acid encoding a p-coumaroyl-CoA:monolignol transferase comprising the isolated nucleic of any of statements 1-8; and
(b) processing the transgenic plant's tissues under conditions sufficient to digest the lignin; and thereby generate the product from the transgenic plant, wherein the transgenic plant's tissues comprise lignin having an increased percent of monolignol coumarates relative to a corresponding untransformed plant.
62. The method of statement 61, wherein the conditions sufficient to digest the lignin comprise conditions sufficient to cleave ester bonds within monolignol coumarate-containing lignin.
63. The method of statement 61 or 62, wherein the conditions sufficient to digest the lignin comprise mildly alkaline conditions.
64. The method of any of statements 61-63, wherein the conditions sufficient to digest the lignin comprise contacting the transgenic plant's tissues with ammonia for a time and a temperature sufficient to cleave ester bonds within monolignol coumarate-containing lignin.
65. The method of any of statements 61-64, wherein the conditions sufficient to digest the lignin would not cleave substantially any of the ether and carbon-carbon bonds in lignin from a corresponding plant that does not contain the isolated nucleic acid encoding the p-coumaroyl-CoA:monolignol transferase.

Statements of a Second Set of Embodiments of the Invention

1A. A transgenic plant comprising a knockdown or knockout of the plant's endogenous p-coumaroyl-CoA:monolignol transferase gene.
2A. The transgenic plant of statement 1A, further comprising a feruloyl-CoA:monolignol transferase nucleic acid operably linked to a promoter functional in cells of the transgenic plant.
3A. The transgenic plant of statement 1A, wherein the endogenous p-coumaroyl-CoA:monolignol transferase gene can hybridize to a nucleic acid with a sequence selected from the group consisting of SEQ ID NO:1 and 3.
4A. The transgenic plant of statement 1A, wherein the endogenous p-coumaroyl-CoA:monolignol transferase gene has at least 50% sequence identity with a nucleic acid sequence selected from the group consisting of SEQ ID NO:1 and 3.
5A. The transgenic plant of statement 1A, wherein the knockdown or knockout is a mutation selected from the group consisting of a point mutation, a deletion, a missense mutation, insertion or a nonsense mutation in the endogenous p-coumaroyl-CoA:monolignol transferase gene.
6A. The transgenic plant of statement 1A, wherein the knockdown or knockout mutation comprises a point mutation, a deletion, a missense mutation, insertion or a nonsense mutation in the endogenous p-coumaroyl-CoA:monolignol transferase gene encoding a polypeptide with at least 60% sequence identity to an amino acid sequence selected from the group consisting of SEQ ID NO: 2 and 4.
7A. The transgenic plant of statement 1A, wherein expression of at least one inhibitory nucleic acid comprising a nucleic acid sequence with at least 90% sequence identity to either strand of a nucleic acid comprising a sequence selected from the group consisting of SEQ ID NO:1 and 3 comprises the knockdown or knockout.
8A. The transgenic plant of statement 1A, wherein the knockdown or knockout reduces acylation of monolignols with p-coumarate.
9A. The transgenic plant of statement 1A, wherein the knockdown or knockout reduces acylation of monolignols with p-coumarate, where the monolignols are selected from the group consisting of p-coumaryl alcohol, coniferyl alcohol and sinapyl alcohol.
10A. The transgenic plant of statement 1A, wherein the knockdown or knockout reduces acylation of monolignols with p-coumarate by at least by 30%.
11A. The transgenic plant of statement 2A, wherein the feruloyl-CoA:monolignol transferase nucleic acid encodes an amino acid sequence of any feruloyl-CoA:monolignol transferase sequence incorporated herein by reference.
12A. The transgenic plant of statement 2A, wherein the feruloyl-CoA:monolignol transferase nucleic acid is operably linked to a promoter selected from the group consisting of a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene, or anactin promoter from rice.
13A. The transgenic plant of statement 1A, wherein the plant is a grass species.
14A. The transgenic plant of statement 1A, wherein the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (Sorghum) and *Bachypodium distachyon* (purple false brome).
15A. The transgenic plant of statement 1A, wherein the plant is fertile.
16A. One or more seeds from the transgenic plant of statement 1A.
17A. An inhibitory nucleic acid comprising a DNA or RNA comprising a nucleic acid sequence with at least 90% sequence identity to either strand of a nucleic acid comprising a sequence selected from the group consisting of SEQ ID NO:1 and 3.
18A. An expression cassette comprising the inhibitory nucleic acid of statement 17A operably linked to a promoter functional in a host cell.
19A. An isolated cell comprising the inhibitory nucleic acid of statement 17A or the expression cassette of statement 18A.
20A. The isolated cell of statement 19A, which is a microorganism or a plant cell.
21A. The isolated cell of statement 19A, wherein the cell is a grass plant cell.
22A. The isolated cell of statement 19A, wherein the cell is a plant cell selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).
23A. A transgenic plant comprising the isolated cell of statement 19A.
24A. A method of incorporating monolignol ferulates into lignin of a plant comprising: a) obtaining one or more plant cells having a knockout or knockdown of the plant cells' endogenous p-coumaroyl-CoA:monolignol transferase gene; b) regenerating one or more of the plant cells into at least one transgenic plant.
25A. The method of statement 24A, further comprising stably transforming the one or more plant cells with an expression cassette comprising a feruloyl-CoA:monolignol transferase nucleic acid operably linked to a promoter to generate one or more transformed plant cells with the endogenous p-coumaroyl-CoA:monolignol transferase knockout or knockdown mutation, before regenerating the cells into at least one transgenic plant.
26A. A method of incorporating monolignol ferulates into lignin of a plant comprising: a) obtaining one or more plant cells stably transformed with a feruloyl-CoA:monolignol transferase nucleic acid operably linked to a promoter to generate at least one transformed plant cell; b) mutating the at least transformed plant cell to generate at least one transformed mutant plant cell with a knockout or knockdown mutation of the plant cell's endogenous p-coumaroyl-CoA:monolignol transferase gene; c) regenerating one or more of the transformed mutant plant cells into at least one transgenic plant.
27A. The method of statement 24A, wherein the endogenous p-coumaroyl-CoA:monolignol transferase gene can hybridize to a nucleic acid with a sequence selected from the group consisting of SEQ ID NO:1 and 3.
28A. The method of statement 24A, wherein the endogenous p-coumaroyl-CoA:monolignol transferase gene has at least 50% sequence identity, with a nucleic acid sequence selected from the group consisting of SEQ ID NO:1 and 3.
29A. The method of statement 24A, wherein the knockdown or knockout comprises a point mutation, a deletion, a missense mutation, an insertion or a nonsense mutation in the endogenous p-coumaroyl-CoA:monolignol transferase gene.
30A. The method of statement 24A, wherein the knockdown or knockout mutation comprises a point mutation, a deletion, a missense mutation, insertion or a nonsense mutation in the endogenous p-coumaroyl-CoA:monolignol transferase gene encoding a polypeptide with at least 60% sequence identity to an amino acid sequence selected from the group consisting of SEQ ID NO:2 and 4.
31A. The method of statement 24A, wherein expression of at least one inhibitory nucleic acid comprising a nucleic acid sequence with at least 90% sequence identity to either strand of a nucleic acid comprising a sequence selected from the group consisting of SEQ ID NO:1 and 3 comprises the knockdown or knockout.

32A. The method of statement 24A, wherein the knockdown or knockout reduces acylation of monolignols with p-coumarate.

33A. The method of statement 24A, wherein the knockdown or knockout reduces acylation of monolignols with p-coumarate, where the monolignols are selected from the group consisting of p-coumaryl alcohol, coniferyl alcohol and sinapyl alcohol.

34A. The method of statement 24A, wherein the knockdown or knockout reduces acylation of monolignols with p-coumarate by at least by 30%.

35A. The method of statement 24A, wherein the feruloyl-CoA:monolignol transferase nucleic acid encodes an amino acid sequence selected from the group consisting of any feruloyl-CoA:monolignol transferase sequence incorporated herein by reference, or an amino acid sequence with at least 60% sequence identity to an amino acid sequence selected from the group consisting of any feruloyl-CoA:monolignol transferase sequence incorporated herein by reference.

36A. The method of statement 25A, wherein the feruloyl-CoA:monolignol transferase nucleic acid is operably linked to a promoter selected from the group consisting of a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene, or anactin promoter from rice.

37A. The method of statement 24A, wherein the plant is a grass species.

38A. The method of statement 24A, wherein the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).

39A. The method of statement 24A, wherein the plant is fertile.

40A. The method of statement 24A, further comprising isolating seeds from the plant.

41A. A method of inhibiting expression and/or translation of p-coumaroyl-CoA:monolignol transferase RNA in a plant cell comprising: a) contacting or transforming plant cells with the expression cassette of statement 18A to generate transformed plant cells; b) regenerating the transformed plant cells into at least one transgenic plant, wherein an inhibitory nucleic acid adapted to inhibit the expression and/or translation of a p-coumaroyl-CoA:monolignol transferase mRNA is expressed in at least one transgenic plant in an amount sufficient to incorporate monolignol ferulates into the lignin of the transgenic plant.

42A. The method of statement 41A, wherein the plant cells are stably transformed with a feruloyl-CoA:monolignol transferase nucleic acid operably linked to a promoter.

Statements of a Third Set of Embodiments of the Invention

1B. An isolated nucleic acid encoding at least a portion of a p-coumaroyl-CoA:monolignol transferase, and/or an isolated nucleic acid complementary to at least a portion of a p-coumaroyl-CoA:monolignol transferase nucleic acid, wherein the isolated nucleic acid can selectively hybridize to a DNA or RNA with a sequence homologous or complementary to a sequence selected from the group consisting of SEQ ID NO: 1 and 3, and a combination thereof.

2B. The isolated nucleic acid of statement 1B, wherein the nucleic acid selectively hybridizes to a DNA or RNA comprising either strand of any of the SEQ ID NO: 1 and 3 sequences under physiological conditions within a live plant cell.

3B. The isolated nucleic acid of statement 1B, wherein the nucleic acid selectively hybridizes to a DNA or RNA comprising either strand of any of the SEQ ID NO: 1 and 3 sequences under stringent hybridization conditions.

4B. The isolated nucleic acid of statement 3B, wherein the stringent hybridization conditions comprise a wash in 0.1×SSC, 0.1% SDS at 65° C.

5B. The isolated nucleic acid of any of statements 1B-5B, wherein the nucleic acid that selectively hybridizes to a DNA or RNA has at least about 40%, 50%, 60%, 70%, 80%, 90% sequence identity with either strand of any of the SEQ ID NO: 1 and 3 sequences.

6B. The isolated nucleic acid of any of statements 1B-5B, wherein the nucleic acid encodes a p-coumaroyl-CoA:monolignol transferase that can catalyze the synthesis of monolignol p-coumarate(s) from monolignol(s) and p-coumaroyl-CoA.

7B. The isolated nucleic acid of statement 6B, wherein the monolignol is coniferyl alcohol, p-coumaryl alcohol, sinapyl alcohol or a combination thereof.

8B. The isolated nucleic acid of any of statements 1B-7B, wherein the nucleic acid encodes a polypeptide with at least 50%, 60%, 70%, 80%, or 90% sequence identity to a polypeptide comprising a SEQ ID NO:2 or SEQ ID NO:4 sequence.

9B. The isolated nucleic acid of any of statements 1B-8B, wherein the nucleic acid encodes p-coumaroyl-CoA:monolignol transferase that can catalyze the synthesis of monolignol p-coumarate(s) from a monolignol(s) and p-coumaroyl-CoA with at least about 50% of the activity of a p-coumaroyl-CoA:monolignol transferase with the SEQ ID NO:2 or SEQ ID NO:4.

10B. The isolated nucleic acid of any of statements 1B-9B, where the isolated nucleic acid is an inhibitory nucleic acid adapted to inhibit the expression and/or translation of a p-coumaroyl-CoA:monolignol transferase mRNA.

11B. The isolated nucleic acid of any of statements 1B-9B, where the isolated nucleic acid is mutating nucleic acid that binds to an endogenous p-coumaroyl-CoA:monolignol transferase gene in a cell of grass species.

12B. The isolated nucleic acid of statement 11B, wherein the mutating nucleic has two flanking segments and a central segment,
wherein the central segment has a point mutation, a deletion, a missense mutation, or a nonsense mutation relative to a nucleic acid selected from the group consisting of SEQ ID NO: 1 and SEQ ID NO:3; and
wherein the two flanking segments are separately homologous or complementary to a different region of a nucleic acid selected from the group consisting of SEQ ID NO: 1 and SEQ ID NO:3.

13B. A transgenic plant cell comprising the isolated nucleic acid of any of statements 1B-12B.

14B. A transgenic plant comprising the plant cell of statement 12B or the isolated nucleic acid of any of statements 1B-13B.

15B. An expression cassette comprising the p-coumaroyl-CoA:monolignol transferase nucleic acid of any of statements 1B-14B operably linked to a promoter functional in a host cell.

16B. The expression cassette of statement 15B, further comprising a feruloyl-CoA:monolignol transferase nucleic acid operably linked to a promoter functional in a host cell.

17B. The expression cassette of statement 15B or 16B, which further comprises a selectable marker gene.

18B. The expression cassette of any of statements 15B-17B, wherein the expression cassette is within an expression vector.

19B. The expression cassette of any of statements 15B-18B, wherein at least one of the promoters is a promoter functional during plant development or growth.

20B. The expression cassette of any of statements 15B-19B, wherein at least one of the promoters is a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene or actin promoter from rice.

21B. A plant cell comprising the expression cassette of any of statements 15B-20B.

22B. The plant cell of statement 21B, wherein the plant cell is a monocot cell, maize cell, grass cell or softwood cell.

23B. The plant cell of statement 21B or 22B, wherein the plant cell is a cell selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).

24B. The plant cell of statement 21B, wherein the plant cell is a dicot cell or a hardwood cell.

25B. A plant comprising the expression cassette of any of statements 15B-20B.

26B. The plant of statement 25B, wherein the plant is a monocot such as a grass species.

27B. The plant of statement 25B or 26B, wherein the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).

28B. The plant of statement 25B, wherein the plant is a dicot or a hardwood.

29B. A method for incorporating monolignol ferulates into lignin of a plant comprising:
a) obtaining one or more plant cells having a knockout or knockdown mutation of the plant cells' endogenous p-coumaroyl-CoA:monolignol transferase gene;
b) stably transforming the one or more plant cells with an expression cassette comprising a feruloyl-CoA:monolignol transferase nucleic acid to generate one or more transformed plant cells with the endogenous p-coumaroyl-CoA:monolignol transferase knockout or knockdown mutation;
c) regenerating one or more of the transformed plant cells into at least one transgenic plant.

30B. The method of statement 29B, wherein the knockout or knockdown mutation increases incorporation of monolignol ferulates into the lignin of at least one of the transgenic plants compared to a control plant that (a) does not have the knockout or knockdown mutation but (b) is stably transformed with the expression cassette comprising feruloyl-CoA:monolignol transferase nucleic acid.

31B. The method of statement 29B or 30B, wherein the knockout or knockdown mutation increases incorporation of monolignol ferulates into the lignin of a plant by at least by 1%, or by at least 2%, or by at least 3%, or by at least 5% relative to a control plant that (a) does not have the knockout or knockdown mutation but (b) is stably transformed with the expression cassette comprising feruloyl-CoA:monolignol transferase nucleic acid.

32B. The method of any of statements 29B-31B, wherein the endogenous p-coumaroyl-CoA:monolignol transferase gene can hybridize to a nucleic acid selected from the group consisting of SEQ ID NO:1 and 3; or the endogenous p-coumaroyl-CoA:monolignol transferase gene has at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, or at least 97% sequence identity with a nucleic acid sequence selected from the group consisting of SEQ ID NO:1 and 3.

33B. A method for incorporating monolignol ferulates into lignin of a plant that includes:
a) stably transforming one or more plant cells with a mutating nucleic acid adapted to hybridize to an endogenous p-coumaroyl-CoA:monolignol transferase gene within the plant cells and replace at least one nucleotide of the endogenous p-coumaroyl-CoA:monolignol transferase gene to generate at least one mutant plant cell with a p-coumaroyl-CoA:monolignol transferase gene knockdown or knockout mutation; or
b) stably transforming one or plant cells with an expression cassette for expression of an inhibitory nucleic acid adapted to hybridize to an endogenous p-coumaroyl-CoA:monolignol transferase nucleic transcript to generate at least one transformed plant cell;
c) regenerating the mutant plant cell or the transformed plant cell into at least one transgenic plant.
34B. The method of statement 33B, wherein the transgenic plant(s) comprises a recombinant feruloyl-CoA:monolignol transferase nucleic acid operably linked to a promoter that expresses the feruloyl-CoA:monolignol transferase protein in the transgenic plant.
35B. The method of statement 34B, wherein the transgenic plant has increased incorporation of monolignol ferulates into its lignin compared to a control plant, wherein the control plant (a) does not have the knockout or knockdown mutation, (b) does not have the expression cassette comprising an inhibitory nucleic acid, but (c) is stably transformed with the recombinant feruloyl-CoA:monolignol transferase nucleic acid operably linked to a promoter that expresses the feruloyl-CoA:monolignol transferase protein.
36B. The method of any of statements 33B-35B, wherein the knockout or knockdown mutation, or the expression cassette comprising an inhibitory nucleic acid, increases incorporation of monolignol ferulates into the lignin of a plant by at least by 1%, or by at least 2%, or by at least 3%, or by at least 5% relative to a control plant that (a) does not have the knockout or knockdown mutation (b) does not have the expression cassette comprising an inhibitory nucleic acid, but (c) is stably transformed with the recombinant feruloyl-CoA:monolignol transferase nucleic acid operably linked to a promoter that expresses the feruloyl-CoA:monolignol transferase protein.
37B. The method of any of statements 33B-36B, wherein the endogenous p-coumaroyl-CoA:monolignol transferase gene can hybridize to a nucleic acid selected from the group consisting of SEQ ID NO:1 and 3; or the endogenous p-coumaroyl-CoA:monolignol transferase gene has at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, or at least 97% sequence identity with a nucleic acid sequence selected from the group consisting of SEQ ID NO:1 and 3.
38B. The method of any of statements 33B-37B, wherein the mutating nucleic acid has two flanking segments and a central segment, wherein the central segment has a point mutation, a deletion, a missense mutation, or a nonsense mutation relative to a nucleic acid selected from the group consisting of SEQ ID NO:1 and SEQ ID NO:3; and wherein the two flanking segments can hybridize to different regions of one of the nucleic acids selected from the group consisting of SEQ ID NO:1 and SEQ ID NO:3.
39B. The method of any of statements 33B-37B, wherein the inhibitory nucleic acid can selectively hybridize to a nucleic acid with a sequence selected from the group consisting SEQ ID NO:1 and 3, and complementary sequences thereof 40B. The method of any of statements 33B-38B, wherein an inhibitory nucleic acid inhibits expression and/or translation of an endogenous p-coumaroyl-CoA:monolignol transferase mRNA expressed in at least one transgenic plant.
41B. The method of any of statements 29B-40B, wherein the transgenic plant is fertile.
42B. The method of any of statements 29B-41B, further comprising recovering transgenic seeds from the transgenic plant.
43B. The method of any of statements 29B-42B, wherein the plant is a monocot.
44B. The method of any of statements 29B-33B, wherein the plant is a grass, maize or softwood plant.
45B. The method of any of statements 29B-44B, the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).
46B. The method of any of statements 29B-42B, wherein the plant is a dicot, or hardwood.
47B. The method of any of statements 29B-46B, wherein the lignin in the plant comprises at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.
48B. The method of any of statements 29B-47B, wherein the lignin in the plant comprises about 1-30% monolignol ferulate, or about 2-30% monolignol ferulate.
49B. The method of any of statements 29B-48B, further comprising breeding a fertile transgenic plant to yield a progeny plant.
50B. The method of statement 49B, wherein the progeny plant comprises lignin with at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.
51B. The method of any of statements 29B-50B, further comprising breeding a fertile transgenic plant to yield a progeny plant that has an increase in the percentage of monolignol ferulates in the lignin of the progeny plant as a dominant trait while still maintaining functional agronomic characteristics relative to the corresponding untransformed plant.
52B. The method of any of statements 29B-51B, further comprising stably transforming the plant cell with at least one selectable marker gene.
53B. A fertile transgenic plant comprising a knockdown or knockout mutation in an endogenous p-coumaroyl-CoA:monolignol transferase gene, and a recombinant feruloyl-CoA:monolignol transferase nucleic acid operably linked to a promoter that expresses the feruloyl-CoA:monolignol transferase protein.
54B. The fertile transgenic plant of statement 53B, wherein the knockdown or knockout mutation and the feruloyl-CoA:monolignol transferase nucleic acid are transmitted through a complete normal sexual cycle of the transgenic plant to the next generation.
55B. A fertile transgenic plant stably transformed by the nucleic acid of any of statements 1B-11B, wherein the nucleic acid is operably linked to a promoter functional in a host cell, wherein the nucleic acid expresses an inhibitory nucleic acid and the nucleic acid is transmitted through a complete normal sexual cycle of the transgenic plant to the next generation.
56B. The fertile transgenic plant of statement 55B, further comprising a feruloyl-CoA:monolignol transferase nucleic acid is transmitted through a complete normal sexual cycle of the transgenic plant to the next generation.
57B. The fertile transgenic plant of any of statements 53B-56B, wherein the plant is a monocot, grass, maize, gymnosperm or softwood.
58B. The fertile transgenic plant of any of statements 53B-57B, the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (*Sorghum*) and *Bachypodium distachyon* (purple false brome).
59B. The fertile transgenic plant of any of statements 53B-56B, wherein the plant is a dicot.
60B. The fertile transgenic plant of any of statements 53B-59B, wherein the plant comprises lignin with at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.
61B. A lignin isolated from a transgenic plant comprising the isolated nucleic acid of any of statements 1B-12B, or the plant cell of statement 13B.
62B. A method of making a product from a transgenic plant comprising:
(a) providing or obtaining a transgenic plant that comprises an isolated nucleic acid encoding a feruloyl-CoA:monolignol transferase and (i) a knockdown or knockout mutation in an endogenous p-coumaroyl-CoA:monolignol transferase gene, or (ii) an expression cassette for expression of an inhibitory nucleic acid adapted to hybridize to an endogenous p-coumaroyl-CoA:monolignol transferase nucleic transcript; and
(b) processing the transgenic plant's tissues under conditions sufficient to digest to the lignin to thereby generate the product from the transgenic plant;
wherein the transgenic plant's tissues comprise lignin having an increased percent of monolignol ferulates relative to a corresponding untransformed plant.
63B. The method of statement 62B, wherein the conditions sufficient to digest to the lignin comprise conditions sufficient to cleave ester bonds within monolignol ferulate-containing lignin.
64B. The method of statement 62B or 63B, wherein the conditions sufficient to digest to the lignin comprise mildly alkaline conditions.
65B. The method of any of statements 62B-64B, wherein the conditions sufficient to digest to the lignin comprise contacting the transgenic plant's tissues with ammonia for a time and a temperature sufficient to cleave ester bonds within monolignol ferulate-containing lignin.
66B. The method of any of statements 62B-65B, wherein the conditions sufficient to digest to the lignin would substantially not cleave ether and carbon-carbon bonds in lignin from a corresponding plant that does not contain the isolated nucleic acid encoding the feruloyl-CoA:monolignol transferase.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are within the following claims.

We claim:

1. A transgenic plant comprising an isolated nucleic acid molecule, wherein the isolated nucleic acid molecule comprises a nucleotide sequence encoding a polypeptide having p-coumaroyl-CoA:monolignol transferase activity, wherein the polypeptide comprises an amino acid sequence having at least 95% amino acid sequence identity to the amino acid sequence as set forth in SEQ ID NO:2, wherein the nucleotide sequence is operably linked to a heterologous promoter functional or active in a plant cell, and wherein expression of the polypeptide in the transgenic plant increases percent of monolignol coumarates in the transgenic plant's lignin as compared to a control plant of the same species lacking the isolated nucleic acid molecule and grown under identical conditions.

2. The transgenic plant of claim 1, wherein the transgenic plant does not have an increased percent of monolignol ferulates in the transgenic plant's lignin as compared to the control plant.

3. The transgenic plant of claim 1, wherein genome of the transgenic plant is stably transformed with the isolated nucleic acid molecule.

4. The transgenic plant of claim 1, wherein the heterologous promoter is functional or active during plant growth or development.

5. The transgenic plant of claim 1, wherein the heterologous promoter is functional or active in a woody tissue of a plant.

6. The transgenic plant of claim 1, wherein the polypeptide has the amino acid sequence as set forth in SEQ ID NO:2.

7. A transgenic seed obtained from the transgenic plant of claim 1, wherein the transgenic seed comprises the isolated nucleic acid molecule.

8. The transgenic seed of claim 7, wherein the polypeptide has the amino acid sequence as set forth in SEQ ID NO:2.

9. A method for increasing a content of monolignol coumarates in lignin within a plant, comprising: (a) planting the transgenic seed of claim 7; and (b) cultivating a transgenic plant germinated from the transgenic seed, wherein expression of the polypeptide in the germinated transgenic plant increases the content of monolignol coumarates in the lignin within the germinated transgenic plant as compared to a control plant lacking the isolated nucleic acid molecule and grown under identical growth conditions.

10. A method of obtaining a plant having increased content of monolignol coumarates in lignin within the plant, comprising the steps:
   (i) stably transforming plant cells with an isolated nucleic acid molecule, wherein the isolated nucleic acid molecule comprises a nucleotide sequence encoding a polypeptide having p-coumaroyl-CoA:monolignol transferase activity, wherein the polypeptide comprises an amino acid sequence having at least 95% amino acid sequence identity to the amino acid sequence as set forth in SEQ ID NO:2, wherein the nucleotide sequence is operably linked to a heterologous promoter functional or active in a plant cell; and
   (ii) regenerating a transgenic plant with the stably transformed plant cells from step (i), wherein genome of the regenerated transgenic plant is stably transformed with the isolated nucleic acid molecule, and wherein the regenerated transgenic plant has increased percent of monolignol coumarates in the regenerated transgenic plant's lignin as compared to a control plant of the same species lacking the isolated nucleic acid molecule and grown under identical conditions.

11. The method of claim 10, wherein the polypeptide has the amino acid sequence as set forth in SEQ ID NO:2.

* * * * *

UNITED STATES PATENT AND TRADEMARK OFFICE
CERTIFICATE OF CORRECTION

PATENT NO. : 11,807,876 B2
APPLICATION NO. : 17/107108
DATED : November 7, 2023
INVENTOR(S) : John Ralph et al.

Page 1 of 1

It is certified that error appears in the above-identified patent and that said Letters Patent is hereby corrected as shown below:

In the Specification

Column 1, Line 8, between "DE-FC02-07ER64494" and "awarded," insert --and DE-SC0020349--.

Signed and Sealed this
Seventeenth Day of June, 2025

Coke Morgan Stewart
*Acting Director of the United States Patent and Trademark Office*

SEQUENCE LISTING

<160> NUMBER OF SEQ ID NOS: 9

<210> SEQ ID NO 1
<211> LENGTH: 1284
<212> TYPE: DNA
<213> ORGANISM: Panicum virgatum

<400> SEQUENCE: 1

```
atgggtacca tcgggttccc ggtgacgagg acgagcaggt cgctggtggc gccgtcgtcg      60
gcgacgccgc aggagacgct gcacctgtcg gtgatcgacc gcgtggcggg gctgcggcac     120
ctggtgcggt cgctgcacgt gttcgacggc cgccgcggcg aggcggcggt gaggacgccg     180
gcggagacgc tgcgggcggc gctggggaag gcgctggtgg actattaccc gctggcgggg     240
```

```
cggttcgtgg aggaggacgg ggaggtgcgg gtggcgtgca cggcgggggg cgcctggttc      300
gtggaggcgg cggcggcgtg caccctggag gaggtgaagc acctggacca ccccatggtc      360
atccccaagg aggacctgct gccggagccg gcgccggacg tcaaccccct cgacatgccg      420
ctcatgatgc aggtgacgga gttcgcgtgc ggcggcttcg tggtgggcct catctccgtg      480
cacaccatcg ccgacggcct gggcgccggg cagttcatca acgcggtggc ggactacgcg      540
cgtggcctcc cgaggccccg cgtgctcccc gtctgggcgc cgacgtcat cccggcgccg       600 tccaggatcg tgtccccgcc gccgcggttc gacctcctgg acctccgcta cttcaccgtg      660
gacctcagcc cggagcacat cgccaaggtc aagtccagct tcttcgaggc gacggggcag      720
cgctgctcgg cgttcgacgt gtgcgtcgcc aagacctggc agtcccgcgt ccgcgcgctc      780
cggctggacg cgacgacccc ggcgcggccc atccacgtgt gcttcttcgc caacacgcgg      840
cacctcctgc cgcagctggc gcccgggttc tacggcaact gcttctacac cgtgagggcg      900
acgcggccct gcggcgaggt ggcggcggcc ggcgtggtgg aggtggtgcg cgccatccgg      960
gacgccaagg cgcggctggg cgcggacttc gcgcggtggg cggcgggcgg gttcgagcgc     1020
gacccctacg agctcacctt cagctacgac tcgctcttcg tctccgactg gacgcggctg     1080
gggttcctgg aggcggacta cgggtggggc gcgccggcgc acgtcgtgcc cttctcctac     1140
caccccttca tggccgtcgc cgtcatcggc gcgccgccgg cgcccaagcc cggcgcgcgc     1200
gtcatgacca tgtgcgtcac ggagaagcac ctgcccgagt tccaggagca gatgaacgcc     1260
ttcgccgccg ggaaccacca gtga                                           1284

<210> SEQ ID NO 2
<211> LENGTH: 427
<212> TYPE: PRT
<213> ORGANISM: Panicum virgatum

<400> SEQUENCE: 2

Met Gly Thr Ile Gly Phe Pro Val Thr Arg Thr Ser Arg Ser Leu Val
1               5                   10                  15

Ala Pro Ser Ser Ala Thr Pro Gln Glu Thr Leu His Leu Ser Val Ile
            20                  25                  30

Asp Arg Val Ala Gly Leu Arg His Leu Val Arg Ser Leu His Val Phe
        35                  40                  45

Asp Gly Arg Arg Gly Glu Ala Ala Val Arg Thr Pro Ala Glu Thr Leu
    50                  55                  60

Arg Ala Ala Leu Gly Lys Ala Leu Val Asp Tyr Tyr Pro Leu Ala Gly
65                  70                  75                  80

Arg Phe Val Glu Glu Asp Gly Glu Val Arg Val Ala Cys Thr Ala Gly
                85                  90                  95

Gly Ala Trp Phe Val Glu Ala Ala Ala Cys Thr Leu Glu Glu Val
            100                 105                 110

Lys His Leu Asp His Pro Met Val Ile Pro Lys Glu Asp Leu Leu Pro
        115                 120                 125

Glu Pro Ala Pro Asp Val Asn Pro Leu Asp Met Pro Leu Met Met Gln
    130                 135                 140

Val Thr Glu Phe Ala Cys Gly Gly Phe Val Gly Leu Ile Ser Val
145                 150                 155                 160

His Thr Ile Ala Asp Gly Leu Gly Ala Gly Gln Phe Ile Asn Ala Val
                165                 170                 175

Ala Asp Tyr Ala Arg Gly Leu Pro Arg Pro Arg Val Leu Pro Val Trp
```

```
                180               185                190
Ala Arg Asp Val Ile Pro Ala Pro Ser Arg Ile Val Ser Pro Pro Pro
            195                 200                 205

Arg Phe Asp Leu Leu Asp Leu Arg Tyr Phe Thr Val Asp Leu Ser Pro
            210                 215                 220

Glu His Ile Ala Lys Val Lys Ser Ser Phe Glu Ala Thr Gly Gln
225                 230                 235                 240

Arg Cys Ser Ala Phe Asp Val Cys Val Ala Lys Thr Trp Gln Ser Arg
                245                 250                 255

Val Arg Ala Leu Arg Leu Asp Gly Asp Asp Pro Ala Arg Pro Ile His
                260                 265                 270

Val Cys Phe Phe Ala Asn Thr Arg His Leu Leu Pro Gln Leu Ala Pro
                275                 280                 285

Gly Phe Tyr Gly Asn Cys Phe Tyr Thr Val Arg Ala Thr Arg Pro Cys
                290                 295                 300

Gly Glu Val Ala Ala Ala Gly Val Val Glu Val Val Arg Ala Ile Arg
305                 310                 315                 320

Asp Ala Lys Ala Arg Leu Gly Ala Asp Phe Ala Arg Trp Ala Ala Gly
                325                 330                 335

Gly Phe Glu Arg Asp Pro Tyr Glu Leu Thr Phe Ser Tyr Asp Ser Leu
                340                 345                 350

Phe Val Ser Asp Trp Thr Arg Leu Gly Phe Leu Glu Ala Asp Tyr Gly
                355                 360                 365

Trp Gly Ala Pro Ala His Val Val Pro Phe Ser Tyr His Pro Phe Met
                370                 375                 380

Ala Val Ala Val Ile Gly Ala Pro Pro Ala Pro Lys Pro Gly Ala Arg
385                 390                 395                 400

Val Met Thr Met Cys Val Thr Glu Lys His Leu Pro Glu Phe Gln Glu
                405                 410                 415

Gln Met Asn Ala Phe Ala Ala Gly Asn His Gln
                420                 425

<210> SEQ ID NO 3
<211> LENGTH: 1311
<212> TYPE: DNA
<213> ORGANISM: Sorghum bicolor

<400> SEQUENCE: 3
atgggcacaa tcgatgatac cgccgggtta ttcccggtga cgaggacgaa caggtcgctg      60
gtgccgccgt cgtcggcgac gccgcaggag acgctgcgcc tgtcggtgat cgaccgcgtg     120
gcggggctgc gccacctggt gcggtcgctg cacgtgttcg ccggcggcga gaacaagaag     180
caggcggcgc cgccggcgaa gtccctgcgg gaggcgctgg gaaaggcgct ggtggactac     240
tacccgttcg cggggcggtt cgtggaggaa gacggggagg tccgggtggc gtgcaccggc     300
gagggcgcct ggttcgtgga ggccgccgcc cgtgctcccc tggaggaggt ccggcacctg     360
gaccacccca tgctcatccc caaggaggag ctgctgccgg agccggcgcc cggcgtcaac     420
ccgctcgaca tgccgctcat gatgcaggtg acggagttca cgtgcggcgg cttcgtggtg     480
ggtctaatct ccgtccacac catcgccgac ggtctaggcg ccgggcagtt catcaacgcg     540
gtggcggact acgcccgtgg cggcgccacc gccggcgccg tcaccagacc ccgcatcacc     600
ccgatctggg cgcgcgacgt gatcccggac ccgcccaaga tgccggcgcc gccgccgcgc     660
ctcgacctgc tggacctggt ctacttcacg acggacctga gcccggacca catcgccaag     720
```

```
gtcaagtcca gctacctcga gtccacgggg cagcgctgct cggcgttcga cgtgtgcgtg    780
gcgcgcacct ggcaggcccg cgtccgcgcg ctccgcctcc cggacgccgc cgcgcccgtc    840
cacgtctgct tcttcgccaa cacccgccac ctgctcccgg cgacggcggc ggcgccggcg    900
agtgggttct acggcaactg cttctacacc gtcaaggcga cgcggcccag cggcgaggtg    960
gcggcggccg acatcgtcga cgtcgtgcgc gccatccggg acgccaaggc gaggctcgcc   1020
gccgacttcg cgaggtgggc ggcgggcggg tttgatcggg accccctacga gctcaccttc   1080 acctacgact ccctcttcgt ctccgactgg acgaggctag ggttcctcga ggctgactat   1140
ggctggggca cgccgacgca cgtcgtgccg ttctcgtacc acccgttcat ggccgtcgcc   1200
gtcatcgggg cgccgccggc gcctaagccc ggcgcacgca tcatgaccat gtgcgtccag   1260
gagcagcacc tgcctgagtt ccaggagcag atgaaccagc cctgctcatg a             1311
```

<210> SEQ ID NO 4
<211> LENGTH: 436
<212> TYPE: PRT
<213> ORGANISM: Sorghum bicolor

<400> SEQUENCE: 4

```
Met Gly Thr Ile Asp Asp Thr Ala Gly Leu Phe Pro Val Thr Arg Thr
1               5                   10                  15

Asn Arg Ser Leu Val Pro Pro Ser Ser Ala Thr Pro Gln Glu Thr Leu
            20                  25                  30

Arg Leu Ser Val Ile Asp Arg Val Ala Gly Leu Arg His Leu Val Arg
        35                  40                  45

Ser Leu His Val Phe Ala Gly Gly Glu Asn Lys Lys Gln Ala Ala Pro
    50                  55                  60

Pro Ala Lys Ser Leu Arg Glu Ala Leu Gly Lys Ala Leu Val Asp Tyr
65                  70                  75                  80

Tyr Pro Phe Ala Gly Arg Phe Val Glu Glu Asp Gly Glu Val Arg Val
                85                  90                  95

Ala Cys Thr Gly Glu Gly Ala Trp Phe Val Glu Ala Ala Ala Ala Cys
            100                 105                 110

Ser Leu Glu Glu Val Arg His Leu Asp His Pro Met Leu Ile Pro Lys
        115                 120                 125

Glu Glu Leu Leu Pro Glu Pro Ala Pro Gly Val Asn Pro Leu Asp Met
    130                 135                 140

Pro Leu Met Met Gln Val Thr Glu Phe Thr Cys Gly Gly Phe Val Val
145                 150                 155                 160

Gly Leu Ile Ser Val His Thr Ile Ala Asp Gly Leu Gly Ala Gly Gln
                165                 170                 175

Phe Ile Asn Ala Val Ala Asp Tyr Ala Arg Gly Gly Thr Ala Gly
            180                 185                 190

Ala Val Thr Arg Pro Arg Ile Thr Pro Ile Trp Ala Arg Asp Val Ile
        195                 200                 205

Pro Asp Pro Pro Lys Met Pro Ala Pro Pro Arg Leu Asp Leu Leu
    210                 215                 220

Asp Leu Val Tyr Phe Thr Thr Asp Leu Ser Pro Asp His Ile Ala Lys
225                 230                 235                 240

Val Lys Ser Ser Tyr Leu Glu Ser Thr Gly Gln Arg Cys Ser Ala Phe
                245                 250                 255

Asp Val Cys Val Ala Arg Thr Trp Gln Ala Arg Val Arg Ala Leu Arg
            260                 265                 270
```

```
Leu Pro Asp Ala Ala Ala Pro Val His Val Cys Phe Phe Ala Asn Thr
        275                 280                 285

Arg His Leu Leu Pro Ala Thr Ala Ala Pro Ala Ser Gly Phe Tyr
    290                 295                 300

Gly Asn Cys Phe Tyr Thr Val Lys Ala Thr Arg Pro Ser Gly Glu Val
305                 310                 315                 320

Ala Ala Ala Asp Ile Val Asp Val Val Arg Ala Ile Arg Asp Ala Lys
                325                 330                 335

Ala Arg Leu Ala Ala Asp Phe Ala Arg Trp Ala Gly Gly Phe Asp
        340                 345                 350

Arg Asp Pro Tyr Glu Leu Thr Phe Thr Tyr Asp Ser Leu Phe Val Ser
    355                 360                 365

Asp Trp Thr Arg Leu Gly Phe Leu Glu Ala Asp Tyr Gly Trp Gly Thr
370                 375                 380

Pro Thr His Val Val Pro Phe Ser Tyr His Pro Phe Met Ala Val Ala
385                 390                 395                 400

Val Ile Gly Ala Pro Pro Ala Pro Lys Pro Gly Ala Arg Ile Met Thr
                405                 410                 415

Met Cys Val Gln Glu Gln His Leu Pro Glu Phe Gln Glu Gln Met Asn
                420                 425                 430

Gln Pro Cys Ser
        435
```

<210> SEQ ID NO 5
<211> LENGTH: 2951
<212> TYPE: DNA
<213> ORGANISM: Artificial Sequence
<220> FEATURE:
<223> OTHER INFORMATION: C4H Promoter

<400> SEQUENCE: 5

```
aagcttagag gagaaactga gaaaatcagc gtaatgagag acgagagcaa tgtgctaaga      60
gaagagattg ggaagagaga agagacgata aaggaaacgg aaaagcatat ggaggagctt     120
catatggagc aagtgaggct gagaagacgg tcgagtgagc ttacggaaga agtggaaagg     180
acgagagtgt ctgcatcgga aatggctgag cagaaaagag aagctataag acagctttgt     240
atgtctcttg accattacag agatgggtac gacaggcttt ggagagttgt tgccggccat     300
aagagtaaga gagtagtggt tttaacaact gaagtgtaa gaacaatgag tcaatgacta     360
cgtgcaggac attggacata ccgtgtgttc ttttggattg aaatgttgtt tcgaagggct     420
gttagttgat gttgaaaata ggttgaagtt gaataatgca tgttgatata gtaaatatca     480
atggtaatat tttctcattt cccaaaactc aaatgatatc atttaattat aaactaacgt     540
aaactgttga caatacactt atggttaaaa atttggagtc ttgttttagt atacgtatca     600
ccaccgcacg gtttcaaaac cacataattg taaatgttat tggaaaaaag aacccgcaat     660
acgtattgta ttttggtaaa catagctcta agcctctaat atataagctc tcaacaattc     720
tggctaatgg tcccaagtaa gaaaagccca tgtattgtaa ggtcatgatc tcaaaaacga     780
gggtgaggtg gaatactaac atgaggagaa agtaaggtga caaattttttg gggcaatagt     840
ggtggatatg gtggggaggt aggtagcatc atttctccaa gtcgctgtct ttcgtggtaa     900
tggtaggtgt gtctctcttt atattattta ttactactca ttgttaattt ctttttttct     960
acaatttgtt tcttactcca aaatacgtca caaatataat actaggcaaa taattattta    1020
attgtaagtc aatagagtgg ttgttgtaaa attgattttt gatattgaaa gagttcatgg    1080
```

| | |
|---|---|
| acggatgtgt atgcgccaaa tgctaagccc ttgtagtctt gtactgtgcc gcgcgtatat | 1140 |
| tttaaccacc actagttgtt tctcttttc aaaaacacac aaaaaataat ttgttttcgt | 1200 |
| aacggcgtca atctgacgg cgtctcaata cgttcaattt tttctttctt tcacatggtt | 1260 |
| tctcatagct ttgcattgac cataggtaaa gggataagga taaaggtttt ttctcttgtt | 1320 |
| tgttttatcc ttattattca aaatggataa aaaaacagtc ttattttgat ttctttgatt | 1380 |
| aaaaaagtca ttgaaattca tatttgattt tttgctaaat gtcaactcag agacacaaac | 1440 |
| gtaatgcact gtcgccaata ttcatggatc atgaccatga atatcactag aataattgaa | 1500 |
| aatcagtaaa atgcaaacaa agcatttttct aattaaaaca gtcttctaca ttcacttaat | 1560 |
| tggaatttcc tttatcaaac ccaaagtcca aaacaatcgg caatgttttg caaaatgttc | 1620 |
| aaaactattg gcgggttggt ctatccgaat tgaagatctt ttctccatat gatagaccaa | 1680 |
| cgaaattcgg catacgtgtt ttttttttg ttttgaaaac cctttaaaca accttaattc | 1740 |
| aaaatactaa tgtaacttta ttgaacgtgc atctaaaaat tttgaactttt gcttttgaga | 1800 |
| aataatcaat gtaccaataa agaagatgta gtacatacat tataattaaa tacaaaaaag | 1860 |
| gaatcaccat atagtacatg gtagacaatg aaaaacttta aaacatatac aatcaataat | 1920 |
| actctttgtg cataactttt tttgtcgtct cgagtttata tttgagtact tatacaaact | 1980 |
| attagattac aaactgtgct cagatacatt aagttaatct tatatacaag agcactcgag | 2040 |
| tgttgtcctt aagttaatct taagatatct tgaggtaaat agaaatagtt aactcgtttt | 2100 |
| tattttctttt tttttaccat gagcaaaaaa agatgaagta agttcaaaac gtgacgaatc | 2160 |
| tacatgttac tacttagtat gtgtcaatca ttaaatcggg aaaacttcat catttcagga | 2220 |
| gtactacaaa actcctaaga gtgagaacga ctacatagta catattttga taaaagactt | 2280 |
| gaaaacttgc taaaacgaat ttgcgaaaat ataatcatac aagtagaacc actgatttga | 2340 |
| tcgaattatt catagctttg taggatgaac ttaactaaat aatatctcac aaaagtattg | 2400 |
| acagtaaccct agtactatac tatctatgtt agaaatatgat tatgatataa tttatccccct | 2460 |
| cacttattca tatgattttt gaagcaacta ctttcgtttt tttaacatttt tctttttttgg | 2520 |
| tttttgttaa tgaacatatt tagtcgtttc ttaattccac tcaaatagaa aatacaaaga | 2580 |
| gaactttatt taatagatat gaacataatc tcacatcctc ctcctacctt caccaaacac | 2640 |
| ttttacatac actttgtggt cttttcttac ctaccaccat caacaacaac accaagcccc | 2700 |
| actcacacac acgcaatcac gttaaatcta acgccgttta ttatctcatc attcaccaac | 2760 |
| tcccacgtac ctaacgccgt ttacctttg ccgttggtcc tcatttctca aaccaaccaa | 2820 |
| acctctccct cttataaaat cctctctccc ttctttattt cttcctcagc agcttcttct | 2880 |
| gctttcaatt actctcgccg acgatttct caccggaaaa aaacaatatc attgcggata | 2940 |
| cacaaactat a | 2951 |

```
<210> SEQ ID NO 6
<211> LENGTH: 24
<212> TYPE: DNA
<213> ORGANISM: Artificial Sequence
<220> FEATURE:
<223> OTHER INFORMATION: Actin2-F Primer

<400> SEQUENCE: 6
```

| | |
|---|---|
| ccagaaggat gcatatgttg gtga | 24 |

```
<210> SEQ ID NO 7
<211> LENGTH: 20
```

```
<212> TYPE: DNA
<213> ORGANISM: Artificial Sequence
<220> FEATURE:
<223> OTHER INFORMATION: Actin2-R Primer

<400> SEQUENCE: 7
gaggagcctc ggtaagaaga                                                    20

<210> SEQ ID NO 8
<211> LENGTH: 19
<212> TYPE: DNA
<213> ORGANISM: Artificial Sequence
<220> FEATURE:
<223> OTHER INFORMATION: SbPMT-F Primer

<400> SEQUENCE: 8
atgggcacaa tcgatgata                                                     19

<210> SEQ ID NO 9
<211> LENGTH: 15
<212> TYPE: DNA
<213> ORGANISM: Artificial Sequence
<220> FEATURE:
<223> OTHER INFORMATION: SbPMT-R Primer

<400> SEQUENCE: 9
agctgagcag ggctg                                                         15
```